United States Patent
Kimura et al.

(10) Patent No.: US 11,713,311 B2
(45) Date of Patent: *Aug. 1, 2023

(54) HETEROCYCLIC COMPOUND

(71) Applicant: Takeda Pharmaceutical Company Limited, Osaka (JP)

(72) Inventors: Eiji Kimura, Kanagawa (JP); Masaki Ogino, Kanagawa (JP); Yasuhisa Kohara, Kanagawa (JP); Tomoko Ohashi, Kanagawa (JP); Tomohiro Kaku, Kanagawa (JP); Yuya Oguro, Kanagawa (JP); Shigemitsu Matsumoto, Kanagawa (JP); Takeshi Wakabayashi, Kanagawa (JP); Norihito Tokunaga, Kanagawa (JP); Taku Kamei, Kanagawa (JP); Mitsuhiro Ito, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/550,173

(22) Filed: Dec. 14, 2021

(65) Prior Publication Data

US 2022/0388995 A1  Dec. 8, 2022

Related U.S. Application Data

(63) Continuation of application No. 16/634,402, filed as application No. PCT/JP2018/028035 on Jul. 26, 2018, now Pat. No. 11,230,541.

(30) Foreign Application Priority Data

Jul. 28, 2017  (JP) .................. 2017-146744

(51) Int. Cl.
| | |
|---|---|
| *C07D 409/12* | (2006.01) |
| *C07D 401/12* | (2006.01) |
| *A61P 25/28* | (2006.01) |
| *A61P 25/24* | (2006.01) |
| *A61P 25/06* | (2006.01) |
| *A61K 9/20* | (2006.01) |
| *A61K 9/48* | (2006.01) |
| *C07D 231/56* | (2006.01) |
| *C07D 235/06* | (2006.01) |
| *C07D 249/18* | (2006.01) |

(52) U.S. Cl.
CPC .......... *C07D 409/12* (2013.01); *A61K 9/2013* (2013.01); *A61K 9/2018* (2013.01); *A61K 9/2054* (2013.01); *A61K 9/2059* (2013.01); *A61K 9/2095* (2013.01); *A61K 9/4825* (2013.01); *A61K 9/4858* (2013.01); *A61K 9/4866* (2013.01); *A61P 25/06* (2018.01); *A61P 25/24* (2018.01); *A61P 25/28* (2018.01); *C07D 231/56* (2013.01); *C07D 235/06* (2013.01); *C07D 249/18* (2013.01); *C07D 401/12* (2013.01)

(58) Field of Classification Search
CPC .. C07D 401/12; C07D 249/18; C07D 235/06; C07D 231/56; C07D 409/12
See application file for complete search history.

(56) References Cited

U.S. PATENT DOCUMENTS

| | | |
|---|---|---|
| 6,387,938 B1 | 5/2002 | Mizuguchi et al. |
| 10,202,376 B2 | 2/2019 | Kimura et al. |
| 10,807,987 B2 | 10/2020 | Oguro et al. |
| 2004/0204409 A1 | 10/2004 | Ando et al. |
| 2005/0137187 A1 | 6/2005 | Souers et al. |
| 2009/0048303 A1 | 2/2009 | Borza et al. |
| 2017/0362223 A1 | 12/2017 | Kimura et al. |

FOREIGN PATENT DOCUMENTS

| | | |
|---|---|---|
| WO | WO 98/01429 A1 | 1/1998 |
| WO | WO 00/21920 A1 | 4/2000 |
| WO | WO 01/30330 A2 | 5/2001 |
| WO | WO 01/32174 A1 | 5/2001 |
| WO | WO 03/035641 A1 | 5/2003 |
| WO | WO 2011/109441 A1 | 9/2011 |
| WO | WO 2012/123471 A1 | 9/2012 |
| WO | WO 2014/134388 A1 | 9/2014 |
| WO | WO 2014/172044 A1 | 10/2014 |
| WO | WO 2016/104434 A1 | 6/2016 |

OTHER PUBLICATIONS

Borza et al., "Benzimidazole-2-carboxamides as novel NR2B selective NMDA receptor antagonists," *Bioorganic & Medicinal Chemistry Letters*, 2006, 16:4638-4640.

Davies et al., A novel series of benzimidazole NR2B-selective NMDA receptor antagonists, *Bioorg. Med. Chem. Lett*, 2012, 22:2620-2623.

Extended European Search Report dated Oct. 19, 2020, for Corresponding European Patent Application No. 18838990.2 (11 pages).

(Continued)

*Primary Examiner* — Shawquia Jackson
(74) *Attorney, Agent, or Firm* — Finnegan, Henderson, Farabow, Garrett & Dunner LLP

(57) ABSTRACT

Provided is a heterocyclic compound that can have an antagonistic action on an NMDA receptor containing the NR2B subunit, and is expected to be useful as a prophylactic or therapeutic agent for major depression, bipolar disorder, migraine, pain, peripheral symptoms of dementia and the like. A compound represented by the formula (I):

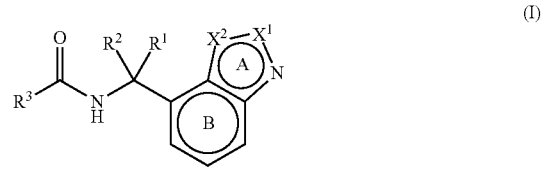

wherein each symbol is as described in the DESCRIPTION, or a salt thereof.

8 Claims, No Drawings

(56) References Cited

OTHER PUBLICATIONS

Jin et al., "Developmental Expression, Subcellular Localization, and Tyrosine Phosphorylation of NR2A and NR2B in the Rat Brain," *Mol. Cells,* 1997, 7(1):64-71.
Monyer et al., "Developmental and Regional Expression in the Rat Brain and Functional Properties of Four NMDA Receptors," *Neuron,* Mar. 1994, 12:529-540.
Thompson et al., Accession No. 2018:2481709, Document No. 170:112996, entered STN, Dec. 13, 2018 (3 pages).
U.S. Appl. No. 17/201,878, filed Mar. 15, 2021, by Oguro et al.
Watanabe et al., "Distinct Distributions of Five N-Methyl-D-Aspartate Receptor Channel Subunit mRNAs in the Forebrain," *The Journal of Comparative Neurology,* 1993, 338:377-390.

HETEROCYCLIC COMPOUND

This application is a continuation of U.S. application Ser. No. 16/634,402, filed Jan. 27, 2020, which is a national stage filing under 35 U.S.C. § 371 of International Application No. PCT/JP2018/028035, filed Jul. 26, 2018, which claims the benefit of priority of Japanese Patent Application No. 2017-146744, filed Jul. 28, 2017, the contents of each of which are incorporated by reference herein in their entireties.

TECHNICAL FIELD

The present invention relates to a heterocyclic compound that can have an antagonistic action on an N-methyl-D-aspartic acid (NMDA) receptor containing the NR2B subunit, and that is expected to be useful as a prophylactic or therapeutic agent for major depression, bipolar disorder, migraine, pain, peripheral symptoms of dementia and the like.

BACKGROUND OF THE INVENTION

The major excitatory neurotransmitter in the central nervous system such as the brain, spinal cord and the like is glutamic acid, and its signal transduction is mediated by N-methyl-D-aspartic acid (NMDA) receptor, gamma-amino-3-hydroxy-5-methyloxazole-4-propionic acid (AMPA)/kainic acid (KA) receptor and metabotropic glutamate receptor. Of these, NMDA receptor is highly permeable to cations including calcium ion and mediate excitatory neurotransmission by depolarizing nerve cells. In addition, calcium flowing into the cell via NMDA receptor functions as a secondary messenger, and causes plastic changes in the nerve function through actions such as changes in the intracellular phosphorylation signal, regulation of transcription and translation of the gene, and the like. Thus, NMDA receptor plays an important role in the functional regulation of central nervous system.

The NMDA receptor is a receptor composed of a tetramer in which 2 to 3 subunits from among NR1, NR2A, NR2B, NR2C, NR2D, NR3A, NR3B subunits are associated, and, to have the function of a receptor responsible for excitatory neurotransmission, the presence of the NR1 subunit is essential. Since the NR1 subunit is contained in all NMDA receptors having the function, it is widely distributed in the central nervous system; however, the distribution and the timing of expression of the NR2 subunit are different for each subunit. For example, NR2A and NR2C subunits are detected only immediately before birth, whereas NR2B and NR2D subunits are observed from an early stage in embryonic development. For example, while the NR2A subunit is widely distributed in the brain, the NR2B subunit is locally expressed in the forebrain and the NR2C subunit is locally expressed in the cerebellum (non-patent document 1).

An NMDA receptor containing the NR2B subunit, which is the target in the present invention, is highly expressed in the cerebral cortex (particularly the second or third layer), hippocampus, amygdala, ventral nucleus of thalamus, and olfactory bulb in the brain of adult rodents. The NMDA receptor is confined to the dorsal horn of the spinal cord (particularly the second layer) in the spinal cord (non-patent document 2). Moreover, in a single cell, the NMDA receptor containing the NR2B subunit is most highly expressed in postsynaptic density and the expression is also found in the extrasynaptic region (non-patent document 3). This suggests that an NMDA receptor containing the NR2B subunit functions widely in the brain and is effective for the prophylaxis or treatment of central diseases.

Patent document 1 discloses the following compounds having a nicotinamide phosphoribosyl transferase (Nampt) inhibitory action and useful for the prophylaxis or treatment of cancer, inflammation and the like.

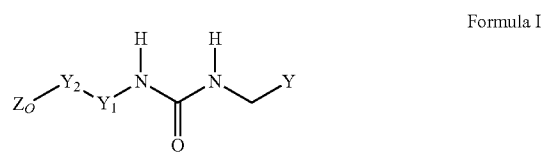

Formula I

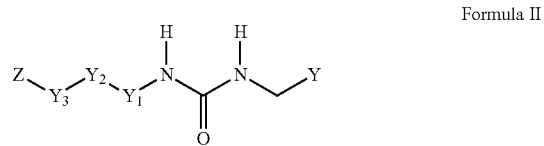

Formula II

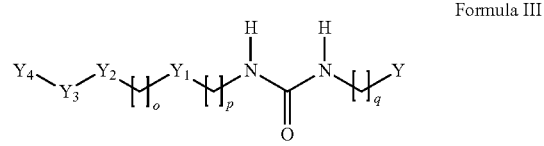

Formula III

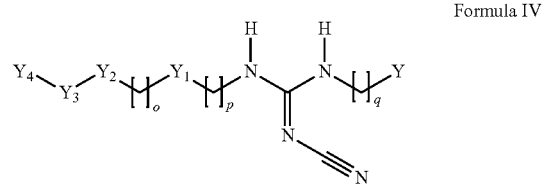

Formula IV wherein each symbol is as defined in the document.

Patent document 2 discloses the following compound having a zeste homologue enhancer (EZH) inhibitory action and useful for the prophylaxis or treatment of cancer (also including central nervous system cancer) and the like.

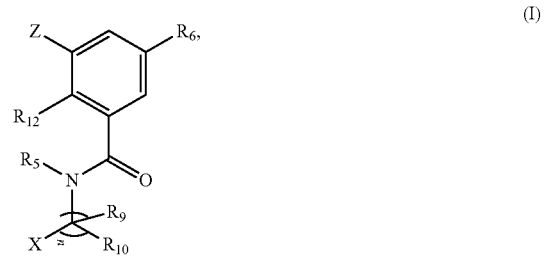

(I)

wherein each symbol is as defined in the document.

Patent document 3 discloses the following compound having a LFA-1 antagonistic action, and a dual LFA-1/MAC-1 antagonistic action and useful for the prophylaxis or treatment of inflammatory diseases (asthma, COPD etc.) and the like.

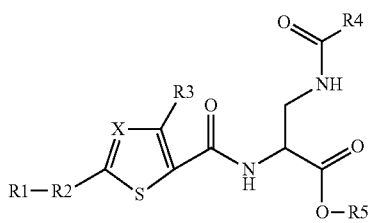

wherein each symbol is as defined in the document.

Patent document 4 discloses the following compound having a melanin coagulation hormone antagonistic action and useful for the prophylaxis or treatment of eating disorder, body weight increase, obesity, memory, depression, psychiatric diseases and the like.

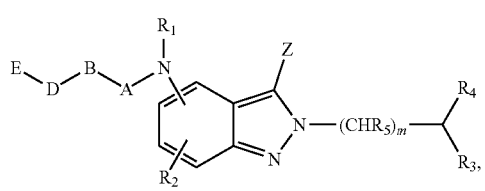

wherein each symbol is as defined in the document.

Patent document 5 discloses the following compound having an eosinophils suppressive action and useful for the prophylaxis or treatment of bronchial asthma, allergic diseases and the like.

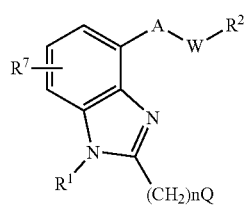

wherein each symbol is as defined in the document.

Patent document 6 discloses the following compound having an intracellular adhesion molecule (ICAM) shutting off activity and useful for the prophylaxis or treatment of inflammatory diseases (rheumatoid arthritis, multiple sclerosis, Crohn's disease, ulcerative colitis etc.) and the like.

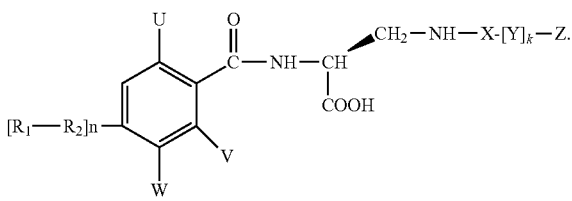

wherein each symbol is as defined in the document.

Patent document 7 discloses the following compound having a antagonistic action on N-methyl-D-aspartic acid (NMDA) receptors including NR2B subunit and useful for the prophylaxis or treatment of major depression, bipolar disorder, migraine, pain, peripheral symptoms of dementia and the like.

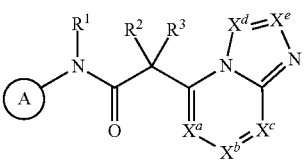

wherein each symbol is as defined in the document.

DOCUMENT LIST

Patent Documents patent document 1: WO 2011/109441A1
patent document 2: WO 2014/172044
patent document 3: WO 2012/123471
patent document 4: US2005/0137187A1
patent document 5: WO 98/01429
patent document 6: WO 00/21920
patent document 7: WO 2016/104434

Non-Patent Document non-patent document 1: Neuron, vol. 12, pages 529-540, 1994
non-patent document 2: The Journal of Comparative Neurology (J. Comp. Neurol.), vol. 338, pages 377-390, 1993
non-patent document 3: Molecules and Cells (Mol. Cells), vol. 7, pages 64-71, 1997

SUMMARY OF THE INVENTION

Problems to be Solved by the Invention

The present invention aims to provide a heterocyclic compound that can have an antagonistic action on NMDA receptor containing the NR2B subunit, and that is expected to be useful as a prophylactic or therapeutic agent for major depression, bipolar disorder, migraine, pain, peripheral symptoms of dementia and the like, and a medicament containing the same.

Means of Solving the Problems

The present inventors have conducted intensive studies in an attempt to solve the above-mentioned problems, and found that a compound represented by the following formula (I) can have a superior antagonistic action on an NMDA receptor containing the NR2B subunit, which resulted in the completion of the present invention.

That is, the present invention provides the following.

[1] A compound represented by the formula (I):

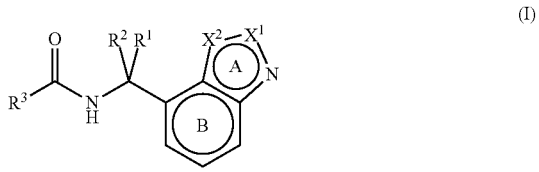

wherein
X$^1$ and X$^2$ are each a carbon atom or a nitrogen atom;
at least one of X$^1$ and X$^2$ is a nitrogen atom;
ring A is an imidazole ring, a pyrazole ring or a triazole ring, each of which is optionally further substituted;
ring B is an optionally further substituted benzene ring;
R$^1$ and R$^2$ are each independently a hydrogen atom or a C$_{1-6}$ alkyl group optionally substituted by fluorine atom(s);
R$^3$ is

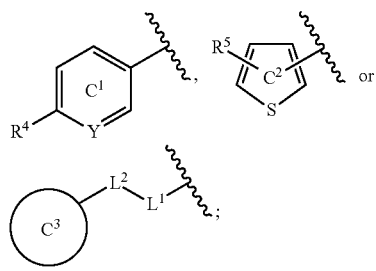

R$^4$ and R$^5$ are each a substituent selected from substituent group X;
Y is N or CR$^6$;
R$^6$ is a hydrogen atom or a substituent;
ring C$^1$ is a benzene ring or a pyridine ring, each of which is optionally further substituted;
ring C$^2$ is a thiophene ring optionally further substituted by a substituent selected from substituent group X;
L$^1$ is an optionally substituted methylene group, O or NH;
L$^2$ is a bond or an optionally substituted methylene group; and
ring C$^3$ is a benzene ring, a pyridine ring or a thiophene ring, each of which is optionally further substituted [substituent group X]
(1) an optionally substituted hydrocarbon group
(2) an optionally substituted heterocyclic group
(3) an optionally substituted C$_{1-6}$ alkoxy group
(4) an optionally substituted C$_{3-10}$ cycloalkyloxy group
(5) a halogen atom
(6) a cyano group
(7) an optionally substituted amino group
(8) an optionally substituted C$_{6-14}$ aryloxy group
(9) an optionally substituted C$_{1-6}$ alkylthio group] or a salt thereof (excluding N-[4-[[[(1H-benzimidazol-7-ylmethyl)amino]carbonyl]amino]phenyl]-[1,1'-biphenyl]-2-sulfonamide and 2-[4-(benzyloxy)phenyl]-N-[[2-[2-(pyrrolidin-1-yl)ethyl]-2H-indazol-4-yl]methyl]acetamide) (sometimes to be abbreviated as "compound (I)" in the present specification).
[2] The compound of [1], wherein ring A is an imidazole ring (that is, X$^1$ is a carbon atom, and X$^2$ is a nitrogen atom), a pyrazole ring (that is, X$^1$ is a nitrogen atom, and X$^2$ is a carbon atom) or a triazole ring (that is, X$^1$ and X$^2$ are both nitrogen atoms), each of which is optionally further substituted by 1 or 2 substituents selected from a C$_{1-6}$ alkyl group and a halogen atom;
ring B is a benzene ring optionally further substituted by 1 to 3 substituents selected from
(1) a halogen atom,
(2) a C$_{1-6}$ alkyl group optionally substituted by 1 to 3 substituents selected from a halogen atom and a C$_{1-6}$ alkoxy group,
(3) a C$_{1-6}$ alkoxy group and
(4) a C$_{3-6}$ cycloalkyl group;

R$^1$ and R$^2$ are both hydrogen atoms;
R$^3$ is

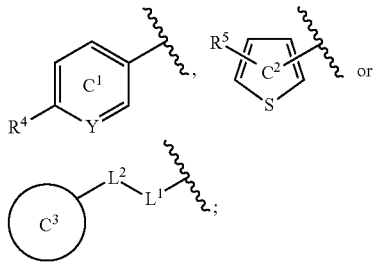

R$^4$ is
(1) a C$_{1-6}$ alkyl group optionally substituted by 1 to 3 halogen atoms,
(2) a C$_{1-6}$ alkoxy group optionally substituted by 1 to 3 halogen atoms or
(3) a halogen atom;
R$^5$ is
(1) a C$_{1-6}$ alkyl group optionally substituted by 1 to 3 halogen atoms,
(2) a C$_{3-6}$ cycloalkyl group,
(3) a C$_{1-6}$ alkoxy group or
(4) a halogen atom;
ring C$^1$ is a benzene ring (that is, Y is CR$^6$) or a pyridine ring (that is, Y is N), each of which is optionally further substituted by 1 to 3 substituents selected from
(1) a halogen atom,
(2) a C$_{1-6}$ alkyl group optionally substituted by 1 to 3 halogen atoms and
(3) a C$_{1-6}$ alkoxy group;
R$^6$ is
(1) a hydrogen atom,
(2) a halogen atom, or
(3) a C$_{1-6}$ alkyl group;
ring C$^2$ is a thiophene ring optionally further substituted by 1 or 2 halogen atoms;
L$^1$ is a methylene group or NH;
L$^2$ is a bond; and
ring C$^3$ is a thiophene ring or a benzene ring, each of which is optionally further substituted by 1 to 5 substituents selected from
(1) a halogen atom,
(2) a C$_{1-6}$ alkyl group optionally substituted by 1 to 3 halogen atoms, and
(3) a C$_{1-6}$ alkoxy group optionally substituted by 1 to 3 halogen atoms,
or a salt thereof.
[3] The compound of [1], wherein ring A is an imidazole ring (that is, X$^1$ is a carbon atom, and X$^2$ is a nitrogen atom) optionally further substituted by 1 or 2 substituents selected from a C$_{1-6}$ alkyl group;
ring B is a benzene ring optionally further substituted by 1 to 3 substituents selected from a C$_{1-6}$ alkyl group and a C$_{1-6}$ alkoxy group;
R$^1$ and R$^2$ are both hydrogen atoms;
R$^3$ is

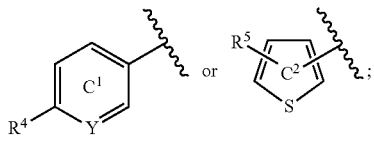

R[4] is
(1) a $C_{1-6}$ alkyl group optionally substituted by 1 to 3 halogen atoms or
(2) a $C_{1-6}$ alkoxy group optionally substituted by 1 to 3 halogen atoms;
R[5] is a $C_{1-6}$ alkyl group optionally substituted by 1 to 3 halogen atoms;
ring $C^1$ is a benzene ring (that is, Y is $CR^6$) or a pyridine ring (that is, Y is N), each of which is optionally further substituted by 1 to 3 halogen atoms;
R[6] is
(1) a hydrogen atom, or
(2) a halogen atom; and
ring $C^2$ is a thiophene ring not further substituted, or a salt thereof.
[4] The compound of [1], wherein the ring A is an imidazole ring (that is, $X^1$ is a carbon atom, and $X^2$ is a nitrogen atom) optionally further substituted by 1 or 2 substituents selected from a $C_{1-6}$ alkyl group;
ring B is a benzene ring optionally further substituted by 1 to 3 substituents selected from a $C_{1-6}$ alkyl group and a $C_{1-6}$ alkoxy group;
$R^1$ and $R^2$ are both hydrogen atoms;
$R^3$ is

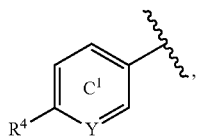

$R^4$ is a $C_{1-6}$ alkoxy group optionally substituted by 1 to 3 halogen atoms;
ring $C^1$ is a benzene ring (that is, Y is $CR^6$) or a pyridine ring (that is, Y is N), each of which is optionally further substituted by 1 to 3 halogen atoms; and
R[6] is
(1) a hydrogen atom or
(2) a halogen atom,
or a salt thereof.
[5] 3,5-Difluoro-4-methoxy-N-((6-methoxy-1-methyl-1H-benzimidazol-7-yl)methyl)benzamide or a salt thereof.
[6] 6-(Difluoromethoxy)-N-((1,6-dimethyl-1H-benzimidazol-7-yl)methyl)-5-fluoronicotinamide or a salt thereof.
[7] N-((1,6-dimethyl-1H-benzimidazol-7-yl)methyl)-4-(trifluoromethoxy)benzamide or a salt thereof.
[8] A medicament comprising the compound of [1] to [7] or a salt thereof.
[9] The medicament of [8], wherein the medicament is an antagonist of an NMDA receptor containing an NR2B subunit.
[10] The medicament of [8], wherein the medicament is a prophylactic or therapeutic agent for major depression, bipolar disorder, migraine, pain, or peripheral symptoms of dementia.
[11] The compound of [1] to [7] or a salt thereof for use in the prophylaxis or treatment of major depression, bipolar disorder, migraine, pain, or peripheral symptoms of dementia.
[12] A method for antagonizing an NMDA receptor containing an NR2B subunit in a mammal, comprising administering an effective amount of the compound of [1] to [7] or a salt thereof to the mammal.
[13] A method for preventing or treating major depression, bipolar disorder, migraine, pain, or peripheral symptoms of dementia in a mammal, comprising administering an effective amount of the compound of [1] to [7] or a salt thereof to the mammal.
[14] Use of the compound of [1] to [7] or a salt thereof for the production of a prophylactic or therapeutic agent for major depression, bipolar disorder, migraine, pain, or peripheral symptoms of dementia.

Effect of the Invention

The present invention provides a heterocyclic compound that can have an antagonistic action on an NMDA receptor containing the NR2B subunit and that is expected to be useful as a prophylactic or therapeutic agent for major depression, bipolar disorder, migraine, pain, peripheral symptoms of dementia and the like, and a medicament containing the same.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),

(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, R-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{310}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{1-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_6$14 arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-25 carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in the formula (I) is explained below.

$X^1$ and $X^2$ are each a carbon atom or a nitrogen atom; at least one of $X^1$ and $X^2$ is a nitrogen atom; ring A is an imidazole ring (that is, $X^1$ is a carbon atom, and $X^2$ is a nitrogen atom), a pyrazole ring (that is, $X^1$ is a nitrogen atom, and $X^2$ is a carbon atom) or a triazole ring (that is, $X^1$ and $X^2$ are both nitrogen atoms), each of which is optionally further substituted.

The "imidazole ring, pyrazole ring or triazole ring" of the "imidazole ring, pyrazole ring or triazole ring, each of which is optionally further substituted" for ring A optionally has 1 or 2 (preferably 1) substituents at substitutable position(s). Examples of the substituent include an optionally substituted $C_{1-6}$ alkyl group (e.g., methyl, ethyl), a halogen atom (e.g., bromine atom) and the like. When a plurality of substituents are present, each substituent may be the same or different.

Ring A is preferably an imidazole ring (that is, $X^1$ is a carbon atom, and $X^2$ is a nitrogen atom), a pyrazole ring (that is, $X^1$ is a nitrogen atom, and $X^2$ is a carbon atom) or a triazole ring (that is, $X^1$ and $X^2$ are both nitrogen atoms), each of which is optionally further substituted by 1 or 2 (preferably 1) substituents selected from an optionally substituted $C_{1-6}$ alkyl group (e.g., methyl, ethyl) and a halogen atom (e.g., bromine atom), more preferably, an imidazole ring (that is, $X^1$ is a carbon atom, and $X^2$ is a nitrogen atom), a pyrazole ring (that is, $X^1$ is a nitrogen atom, and $X^2$ is a carbon atom) or a triazole ring (that is, $X^1$ and $X^2$ are both nitrogen atoms), each of which is optionally further substituted by 1 or 2 (preferably 1) substituents selected from a $C_{1-6}$ alkyl group (e.g., methyl, ethyl) and a halogen atom (e.g., bromine atom), further preferably, an imidazole ring (that is, $X^1$ is a carbon atom, and $X^2$ is a nitrogen atom) optionally further substituted by 1 or 2 (preferably 1) substituents selected from a $C_{1-6}$ alkyl group (e.g., methyl).

Ring B is an optionally further substituted benzene ring.

The "benzene ring" of the "optionally further substituted benzene ring" for ring B optionally has 1 to 3 (preferably 1 or 2) substituents at substitutable position(s). Examples of such substituent include a halogen atom (e.g., fluorine atom, iodine atom), an optionally substituted $C_{1-6}$ alkyl group (e.g., methyl, ethyl), an optionally substituted $C_{1-6}$ alkoxy group (e.g., methoxy, ethoxy), an optionally substituted $C_{3-6}$ cycloalkyl group (e.g., cyclopropyl) and the like. When a plurality of substituents are present, each substituent may be the same or different.

Ring B is preferably a benzene ring optionally further substituted by 1 to 3 (preferably 1 or 2) substituents selected from (1) a halogen atom (e.g., fluorine atom, iodine atom), (2) an optionally substituted $C_{1-6}$ alkyl group (e.g., methyl, ethyl), (3) an optionally substituted $C_{1-6}$ alkoxy group (e.g., methoxy, ethoxy) and (4) an optionally substituted $C_{3-6}$ cycloalkyl group (e.g., cyclopropyl), more preferably, a benzene ring optionally further substituted by 1 to 3 (preferably 1 or 2) substituents selected from (1) a halogen atom (e.g., fluorine atom, iodine atom), (2) a $C_{1-6}$ alkyl group (e.g., methyl, ethyl) optionally substituted by 1 to 3 (preferably 1 or 2) substituents selected from a halogen atom (e.g., fluorine atom) and a $C_{1-6}$ alkoxy group (e.g., methoxy), (3) a $C_{1-6}$ alkoxy group (e.g., methoxy, ethoxy) and (4) a $C_{3-6}$ cycloalkyl group (e.g., cyclopropyl), further preferably, a benzene ring optionally further substituted by 1 to 3 (preferably 1 or 2) substituents selected from a $C_{1-6}$ alkyl group (e.g., methyl, ethyl) and a $C_{1-6}$ alkoxy group (e.g., methoxy), further more preferably, a benzene ring optionally further substituted by 1 to 3 (preferably 1 or 2) substituents selected from a $C_{1-6}$ alkyl group (e.g., methyl) and a C-s alkoxy group (e.g., methoxy).

$R^1$ and $R^2$ are each independently a hydrogen atom or a $C_{1-6}$ alkyl group optionally substituted by fluorine atom(s).

$R^1$ and $R^2$ are both preferably hydrogen atoms.

$R^3$ is

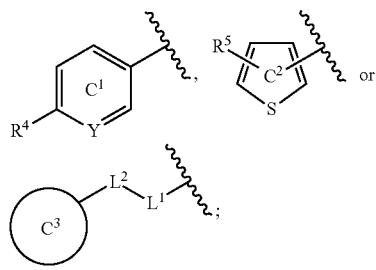

$R^4$ and $R^5$ are each a substituent selected from substituent group X; Y is N or $CR^6$; $R^6$ is a hydrogen atom or a substituent; ring $C^1$ is a benzene ring (that is, Y is $CR^6$) or a pyridine ring (that is, Y is N), each of which is optionally further substituted; ring $C^2$ is a thiophene ring optionally further substituted by a substituent selected from substituent group X; $L^1$ is an optionally substituted methylene group, O or NH; $L^2$ is a bond or an optionally substituted methylene group; ring $C^3$ is a benzene ring, a pyridine ring or a thiophene ring, each of which is optionally further substituted.

$R^3$ is preferably

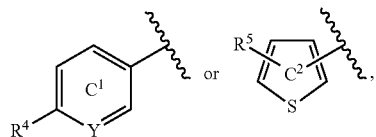

more preferably

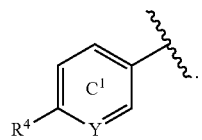

The [substituent group X] includes
(1) an optionally substituted hydrocarbon group,
(2) an optionally substituted heterocyclic group,
(3) an optionally substituted $C_{1-6}$ alkoxy group,
(4) an optionally substituted $C_{3-10}$ cycloalkyloxy group,
(5) a halogen atom,
(6) a cyano group,
(7) an optionally substituted amino group,
(8) an optionally substituted $C_{6-14}$ aryloxy group, and
(9) an optionally substituted $C_{1-6}$ alkylthio group.

The "optionally substituted $C_{1-6}$ alkoxy group" for the substituent group X is, for example, a $C_{1-6}$ alkoxy group optionally substituted by 1 to 3 substituents selected from the aforementioned substituent group A.

The "optionally substituted $C_{3-10}$ cycloalkyloxy group" for the substituent group X is, for example, a $C_{3-10}$ cycloalkyloxy group optionally substituted by 1 to 3 substituents selected from the aforementioned substituent group A.

The "optionally substituted $C_{6-14}$ aryloxy group" for the substituent group X is, for example, a $C_{6-14}$ aryloxy group optionally substituted by 1 to 3 substituents selected from the aforementioned substituent group A.

The "optionally substituted $C_{1-6}$ alkylthio group" for the substituent group X is, for example, a $C_{1-6}$ alkylthio group optionally substituted by 1 to 3 substituents selected from the aforementioned substituent group A.

The "optionally substituted hydrocarbon group" of the "substituent selected from substituent group X" represented by $R^4$ is, for example, an optionally substituted $C_{1-6}$ alkyl group (e.g., methyl) or the like.

$R^4$ is preferably (1) an optionally substituted $C_{1-6}$ alkyl group (e.g., methyl, ethyl), (2) an optionally substituted $C_{1-6}$ alkoxy group (e.g., methoxy, ethoxy) or (3) a halogen atom (e.g., fluorine atom, chlorine atom), more preferably, (1) a $C_{1-6}$ alkyl group (e.g., methyl, ethyl) optionally substituted by 1 to 3 halogen atoms (e.g., fluorine atom), (2) a $C_{1-6}$ alkoxy group (e.g., methoxy, ethoxy) optionally substituted by 1 to 3 halogen atoms (e.g., fluorine atom) or (3) a halogen atom (e.g., fluorine atom, chlorine atom), further preferably, (1) a $C_{1-6}$ alkyl group (e.g., methyl) optionally substituted by 1 to 3 halogen atoms (e.g., fluorine atom) or (2) a $C_{1-6}$ alkoxy group (e.g., methoxy) optionally substituted by 1 to 3 halogen atoms (e.g., fluorine atom), further more preferably, a $C_{1-6}$ alkoxy group (e.g., methoxy) optionally substituted by 1 to 3 halogen atoms (e.g., fluorine atom).

The "optionally substituted hydrocarbon group" of the "substituent selected from substituent group X" represented by $R^5$ is, for example, an optionally substituted $C_{1-6}$ alkyl group (e.g., methyl, ethyl), an optionally substituted $C_{3-6}$ cycloalkyl group (e.g., cyclopropyl) or the like.

$R^5$ is preferably (1) an optionally substituted $C_{1-6}$ alkyl group (e.g., methyl, ethyl), (2) an optionally substituted $C_{3-6}$ cycloalkyl group (e.g., cyclopropyl), (3) an optionally substituted $C_{1-6}$ alkoxy group (e.g., methoxy) or (4) a halogen atom (e.g., chlorine atom), more preferably, (1) a $C_{1-6}$ alkyl group (e.g., methyl, ethyl) optionally substituted by 1 to 3 halogen atoms (e.g., fluorine atom), (2) a $C_{3-6}$ cycloalkyl group (e.g., cyclopropyl), (3) a $C_{1-6}$ alkoxy group (e.g., methoxy) or (4) a halogen atom (e.g., chlorine atom), further preferably, a $C_{1-6}$ alkyl group (e.g., methyl) optionally substituted by 1 to 3 halogen atoms (e.g., fluorine atom).

The "substituent" represented by $R^6$ is, for example, a substituent selected from the aforementioned substituent group A.

$R^6$ is preferably (1) a hydrogen atom, (2) a halogen atom (e.g., fluorine atom, chlorine atom) or (3) an optionally substituted $C_{1-6}$ alkyl group (e.g., methyl), more preferably, (1) a hydrogen atom, (2) a halogen atom (e.g., fluorine atom, chlorine atom) or (3) a $C_{1-6}$ alkyl group (e.g., methyl), further preferably, (1) a hydrogen atom or (2) a halogen atom (e.g., fluorine atom).

The "benzene ring or a pyridine ring" of the "benzene ring or pyridine ring, each of which is optionally further substituted" represented by ring $C^1$ is optionally further substituted by 1 to 3 (preferably 1 or 2) substituents other than $R^4$ and $R^6$ at substitutable position(s). Examples of such substituent include a halogen atom (e.g., fluorine atom, chlorine atom), an optionally substituted $C_{1-6}$ alkyl group (e.g., methyl), an optionally substituted $C_{1-6}$ alkoxy group (e.g., methoxy) and the like. When a plurality of substituents are present, each substituent may be the same or different.

Ring $C^1$ is preferably a benzene ring or a pyridine ring, each of which is optionally further substituted by 1 to 3 (preferably 1 or 2) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy), more preferably, a benzene ring or a pyridine ring, each of which is optionally further substituted by 1 to 3 (preferably 1 or 2) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy), further preferably, a benzene ring (that is, Y is $CR^6$) or a pyridine ring (that is, Y is N), each of which is optionally further substituted by 1 to 3 halogen atoms (e.g., fluorine atom).

The "thiophene ring" of the "thiophene ring optionally further substituted by a substituent selected from substituent group X" represented by ring $C^2$ is optionally further substituted by 1 or 2 (preferably 1) "substituents selected from substituent group X" other than $R^5$ at substitutable position(s). As the "substituent selected from substituent group X", a halogen atom (e.g., chlorine atom) is preferable. When a plurality of substituents are present, each substituent may be the same or different.

Ring $C^2$ is preferably a thiophene ring optionally further substituted by 1 or 2 (preferably 1) halogen atoms (e.g., chlorine atom), more preferably, a thiophene ring not further substituted.

The "optionally substituted methylene group" represented by $L^1$ or $L^2$ is, for example, a methylene group optionally substituted by 1 or 2 substituents selected from the aforementioned substituent group A.

$L^1$ is preferably an optionally substituted methylene group or NH, more preferably, a methylene group or NH.

$L^2$ is preferably a bond.

The "benzene ring, pyridine ring or thiophene ring" of the "benzene ring, pyridine ring or thiophene ring, each of which is optionally further substituted" represented by ring $C^3$ optionally has 1 to 5 (preferably 1 to 3) substituents at substitutable position(s). Examples of such substituent include a halogen atom (e.g., fluorine atom, chlorine atom), an optionally substituted $C_{1-6}$ alkyl group (e.g., methyl), an optionally substituted $C_{1-6}$ alkoxy group (e.g., methoxy) and the like. When a plurality of substituents are present, each substituent may be the same or different.

Ring $C^3$ is preferably a thiophene ring or a benzene ring, each of which is optionally further substituted by 1 to 5 (preferably 1 to 3) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy), more preferably, a thiophene ring or a benzene ring, each of which is optionally further substituted by 1 to 5 (preferably 1 to 3) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy) optionally substituted by 1 to 3 halogen atoms (e.g., fluorine atom), further preferably, (A) a thiophene ring or (B) a benzene ring optionally further substituted by 1 to 5 (preferably 1 to 3) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy) optionally substituted by 1 to 3 halogen atoms (e.g., fluorine atom).

Preferable examples of compound (I) include the following compounds.

[Compound A]

Compound (I), wherein ring A is an imidazole ring (that is, $X^1$ is a carbon atom, and $X^2$ is a nitrogen atom), a pyrazole ring (that is, $X^1$ is a nitrogen atom, and $X^2$ is a carbon atom) or a triazole ring (that is, $X^1$ and $X^2$ are both nitrogen atoms), each of which is optionally further substituted by 1 or 2 (preferably 1) substituents selected from an optionally substituted $C_{1-6}$ alkyl group (e.g., methyl, ethyl);

ring B is a benzene ring optionally further substituted by 1 to 3 (preferably 1 or 2) substituents selected from (1) a halogen atom (e.g., fluorine atom, iodine atom), (2) an optionally substituted $C_{1-6}$ alkyl group (e.g., methyl, ethyl), (3) an optionally substituted $C_{1-6}$ alkoxy group (e.g., methoxy, ethoxy) and (4) an optionally substituted $C_{3-6}$ cycloalkyl group (e.g., cyclopropyl);

$R^1$ and $R^2$ are both hydrogen atoms;

$R^3$ is

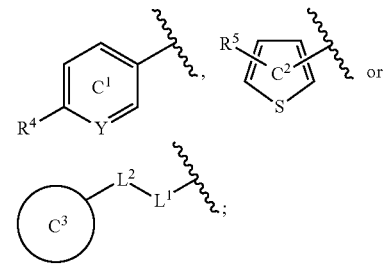

$R^4$ is (1) an optionally substituted $C_{1-6}$ alkyl group (e.g., methyl), (2) an optionally substituted $C_{1-6}$ alkoxy group (e.g., methoxy, ethoxy) or (3) a halogen atom (e.g., fluorine atom, chlorine atom);

$R^5$ is (1) an optionally substituted $C_{1-6}$ alkyl group (e.g., methyl, ethyl), (2) an optionally substituted $C_{3-6}$ cycloalkyl group (e.g., cyclopropyl), (3) an optionally substituted $C_{1-6}$ alkoxy group (e.g., methoxy) or (4) a halogen atom (e.g., chlorine atom);

ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy);

$R^6$ is (1) a hydrogen atom, (2) a halogen atom (e.g., fluorine atom, chlorine atom) or (3) an optionally substituted $C_{1-6}$ alkyl group (e.g., methyl);

ring $C^2$ is a thiophene ring optionally further substituted by 1 or 2 (preferably 1) halogen atoms (e.g., chlorine atom);

$L^1$ is an optionally substituted methylene group or NH;

$L^2$ is a bond; and ring $C^3$ is a thiophene ring or a benzene ring, each of which is optionally further substituted by 1 to 5 (preferably 1 to 3) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy).

[Compound B]

Compound (I), wherein ring A is an imidazole ring (that is, $X^1$ is a carbon atom, and $X^2$ is a nitrogen atom), a pyrazole ring (that is, $X^1$ is a nitrogen atom, and $X^2$ is a carbon atom) or a triazole ring (that is, $X^1$ and $X^2$ are both nitrogen atoms), each of which is optionally further substituted by 1 or 2 (preferably 1) substituents selected from a $C_{1-6}$ alkyl group (e.g., methyl, ethyl);

ring B is a benzene ring optionally further substituted by 1 to 3 (preferably 1 or 2) substituents selected from (1) a halogen atom (e.g., fluorine atom, iodine atom), (2) a $C_{1-6}$ alkyl group (e.g., methyl, ethyl) optionally substituted by 1 to 3 halogen atoms (e.g., fluorine atom), (3) a $C_{1-6}$ alkoxy group (e.g., methoxy, ethoxy) and (4) a $C_{3-6}$ cycloalkyl group (e.g., cyclopropyl);

$R^1$ and $R^2$ are both hydrogen atoms;

$R^3$ is

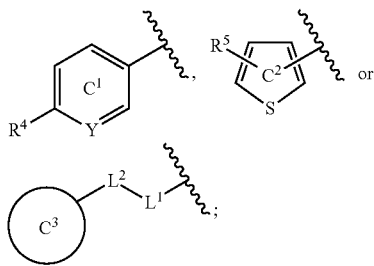

$R^4$ is (1) a $C_{1-6}$ alkyl group (e.g., methyl) optionally substituted by 1 to 3 halogen atoms (e.g., fluorine atom), (2) a $C_{1-6}$ alkoxy group (e.g., methoxy, ethoxy) optionally substituted by 1 to 3 halogen atoms (e.g., fluorine atom) or (3) a halogen atom (e.g., fluorine atom, chlorine atom);

$R^5$ is (1) a $C_{1-6}$ alkyl group (e.g., methyl, ethyl) optionally substituted by 1 to 3 halogen atoms (e.g., fluorine atom), (2) a $C_{3-6}$ cycloalkyl group (e.g., cyclopropyl), (3) a $C_{1-6}$ alkoxy group (e.g., methoxy) or (4) a halogen atom (e.g., chlorine atom);

ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy);

$R^6$ is (1) a hydrogen atom, (2) a halogen atom (e.g., fluorine atom, chlorine atom) or (3) a $C_{1-6}$ alkyl group (e.g., methyl);

ring $C^2$ is a thiophene ring optionally further substituted by 1 or 2 (preferably 1) halogen atoms (e.g., chlorine atom);

$L^1$ is a methylene group or NH;

$L^2$ is a bond; and ring $C^3$ is a thiophene ring or a benzene ring, each of which is optionally further substituted by 1 to 5 (preferably 1 to 3) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy) optionally substituted by 1 to 3 halogen atoms (e.g., fluorine atom).

[Compound C]

Compound (I), wherein ring A is an imidazole ring (that is, $X^1$ is a carbon atom, and $X^2$ is a nitrogen atom) optionally further substituted by 1 or 2 (preferably 1) substituents selected from a $C_{1-6}$ alkyl group (e.g., methyl);

ring B is a benzene ring optionally further substituted by 1 to 3 (preferably 1 or 2) substituents selected from a $C_{1-6}$ alkyl group (e.g., methyl, ethyl) and a $C_{1-6}$ alkoxy group (e.g., methoxy);

$R^1$ and $R^2$ are both hydrogen atoms;

$R^3$ is

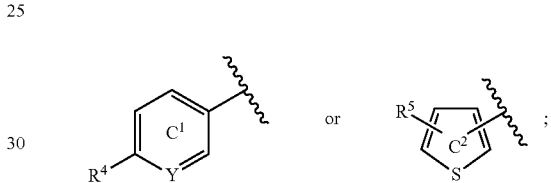

$R^4$ is (1) a $C_{1-6}$ alkyl group (e.g., methyl) optionally substituted by 1 to 3 halogen atoms (e.g., fluorine atom) or (2) a $C_{1-6}$ alkoxy group (e.g., methoxy) optionally substituted by 1 to 3 halogen atoms (e.g., fluorine atom);

$R^5$ is a $C_{1-6}$ alkyl group (e.g., methyl) optionally substituted by 1 to 3 halogen atoms (e.g., fluorine atom);

ring $C^1$ is a benzene ring (that is, Y is $CR^6$) or a pyridine ring (that is, Y is N), each of which is optionally further substituted by 1 to 3 halogen atoms (e.g., fluorine atom);

$R^6$ is (1) a hydrogen atom or (2) a halogen atom (e.g., fluorine atom); and ring $C^2$ is a thiophene ring not further substituted.

[Compound A-1]

The above-mentioned [Compound A], wherein $R^3$ is

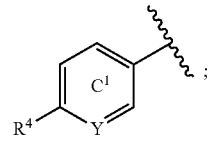

$R^4$ is (1) an optionally substituted $C_{1-6}$ alkyl group (e.g., methyl), (2) an optionally substituted $C_{1-6}$ alkoxy group (e.g., methoxy, ethoxy) or (3) a halogen atom (e.g., fluorine atom, chlorine atom); and ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy).

[Compound B-1]
The above-mentioned [Compound B], wherein $R^3$ is

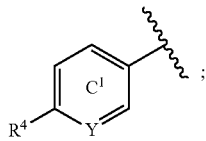

$R^4$ is (1) a $C_{1-6}$ alkyl group (e.g., methyl) optionally substituted by 1 to 3 halogen atoms (e.g., fluorine atom), (2) a $C_{1-6}$ alkoxy group (e.g., methoxy, ethoxy) optionally substituted by 1 to 3 halogen atoms (e.g., fluorine atom) or (3) a halogen atom (e.g., fluorine atom, chlorine atom); and ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy).

[Compound C-1]
The above-mentioned [Compound C], wherein $R^3$ is

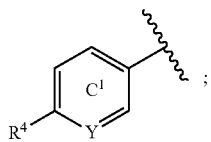

$R^4$ is (1) a $C_{1-6}$ alkyl group (e.g., methyl) optionally substituted by 1 to 3 halogen atoms (e.g., fluorine atom) or (2) a $C_{1-6}$ alkoxy group (e.g., methoxy) optionally substituted by 1 to 3 halogen atoms (e.g., fluorine atom); and ring $C^1$ is a benzene ring (that is, Y is $CR^6$) or a pyridine ring (that is, Y is N), each of which is optionally further substituted by 1 to 3 halogen atoms (e.g., fluorine atom).

[Compound A-2]
Compound (I), wherein ring A is an imidazole ring (that is, $X^1$ is a carbon atom, and $X^2$ is a nitrogen atom) or a pyrazole ring (that is, $X^1$ is a nitrogen atom, and $X^2$ is a carbon atom), each of which is optionally further substituted by 1 or 2 (preferably 1) substituents selected from a optionally substituted $C_{1-6}$ alkyl group (e.g., methyl);

ring B is a benzene ring optionally further substituted by 1 to 3 (preferably 1 or 2) substituents selected from (1) an optionally substituted $C_{1-6}$ alkyl group (e.g., methyl, ethyl), (2) an optionally substituted $C_{1-6}$ alkoxy group (e.g., methoxy, ethoxy) and (3) an optionally substituted $C_{3-6}$ cycloalkyl group (e.g., cyclopropyl);

$R^1$ and $R^2$ are both hydrogen atoms;

$R^3$ is

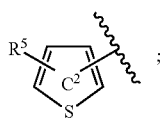

$R^5$ is (1) an optionally substituted $C_{1-6}$ alkyl group (e.g., methyl, ethyl), (2) an optionally substituted $C_{3-6}$ cycloalkyl group (e.g., cyclopropyl), (3) an optionally substituted $C_{1-6}$ alkoxy group (e.g., methoxy) or (4) a halogen atom (e.g., chlorine atom); and ring $C^2$ is a thiophene ring optionally further substituted by 1 or 2 (preferably 1) halogen atoms (e.g., chlorine atom).

[Compound B-2]
Compound (I), wherein ring A is an imidazole ring (that is, $X^1$ is a carbon atom, and $X^2$ is a nitrogen atom) or a pyrazole ring (that is, $X^1$ is a nitrogen atom, and $X^2$ is a carbon atom), each of which is optionally further substituted by 1 or 2 (preferably 1) substituents selected from a $C_{1-6}$ alkyl group (e.g., methyl);

ring B is a benzene ring optionally further substituted by 1 to 3 (preferably 1 or 2) substituents selected from (1) a $C_{1-6}$ alkyl group (e.g., methyl, ethyl), (2) a $C_{1-6}$ alkoxy group (e.g., methoxy, ethoxy) and (3) a $C_{3-6}$ cycloalkyl group (e.g., cyclopropyl);

$R^1$ and $R^2$ are both hydrogen atoms;

$R^3$ is

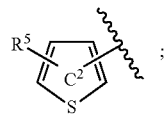

$R^5$ is (1) a $C_{1-6}$ alkyl group (e.g., methyl, ethyl) optionally substituted by 1 to 3 halogen atoms (e.g., fluorine atom), (2) a $C_{3-6}$ cycloalkyl group (e.g., cyclopropyl), (3) a $C_{1-6}$ alkoxy group (e.g., methoxy) or (4) a halogen atom (e.g., chlorine atom); and ring $C^2$ is a thiophene ring optionally further substituted by 1 or 2 (preferably 1) halogen atoms (e.g., chlorine atom).

[Compound C-2]
Compound (I), wherein ring A is an imidazole ring (that is, $X^1$ is a carbon atom, and $X^2$ is a nitrogen atom) optionally further substituted by 1 or 2 (preferably 1) substituents selected from a $C_{1-6}$ alkyl group (e.g., methyl);

ring B is a benzene ring optionally further substituted by 1 to 3 (preferably 1 or 2) substituents selected from a $C_{1-6}$ alkoxy group (e.g., methoxy);

$R^1$ and $R^2$ are both hydrogen atoms;

$R^3$ is

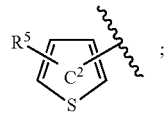

$R^5$ is a $C_{1-6}$ alkyl group (e.g., methyl) optionally substituted by 1 to 3 halogen atoms (e.g., fluorine atom); and ring $C^2$ is a thiophene ring not further substituted.

[Compound A-3]
Compound (I), wherein ring A is an imidazole ring (that is, $X^1$ is a carbon atom, and $X^2$ is a nitrogen atom) or a pyrazole ring (that is, $X^1$ is a nitrogen atom, and $X^2$ is a carbon atom), each of which is optionally further substituted by 1 or 2 (preferably 1) substituents selected from an optionally substituted $C_{1-6}$ alkyl group (e.g., methyl);

ring B is a benzene ring optionally further substituted by 1 to 3 (preferably 1 or 2) substituents selected from (1) an optionally substituted $C_{1-6}$ alkoxy group (e.g., methoxy) and (2) an optionally substituted $C_{3-6}$ cycloalkyl group (e.g., cyclopropyl);

$R^1$ and $R^2$ are both hydrogen atoms;
$R^3$ is

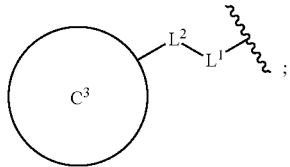

$L^1$ is an optionally substituted methylene group or NH;
$L^2$ is a bond; and
ring $C^3$ is a thiophene ring or a benzene ring, each of which is optionally further substituted by 1 to 5 (preferably 1 to 3) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy).

[Compound B-3]

Compound (I), wherein ring A is an imidazole ring (that is, $X^1$ is a carbon atom, and $X^2$ is a nitrogen atom) or a pyrazole ring (that is, $X^1$ is a nitrogen atom, and $X^2$ is a carbon atom), each of which is optionally further substituted by 1 or 2 (preferably 1) substituents selected from a $C_{1-6}$ alkyl group (e.g., methyl);

ring B is a benzene ring optionally further substituted by 1 to 3 (preferably 1 or 2) substituents selected from (1) a $C_{1-6}$ alkoxy group (e.g., methoxy) and (2) a $C_{3-6}$ cycloalkyl group (e.g., cyclopropyl);

$R^1$ and $R^2$ are both hydrogen atoms;
$R^3$ is

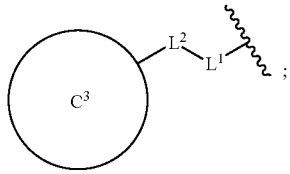

$L^1$ is a methylene group or NH;
$L^2$ is a bond; and
ring $C^3$ is a thiophene ring or a benzene ring, each of which is optionally further substituted by 1 to 5 (preferably 1 to 3) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy) optionally substituted by 1 to 3 halogen atoms (e.g., fluorine atom).

[Compound A-a]

Compound (I), wherein ring A is an imidazole ring (that is, $X^1$ is a carbon atom, and $X^2$ is a nitrogen atom), a pyrazole ring (that is, $X^1$ is a nitrogen atom, and $X^2$ is a carbon atom) or triazole ring (that is, $X^1$ and $X^2$ are both nitrogen atoms), each of which is optionally further substituted by 1 or 2 (preferably 1) substituents selected from an optionally substituted $C_{1-6}$ alkyl group (e.g., methyl, ethyl) and a halogen atom (e.g., bromine atom);

ring B is a benzene ring optionally further substituted by 1 to 3 (preferably 1 or 2) substituents selected from (1) a halogen atom (e.g., fluorine atom, iodine atom), (2) an optionally substituted $C_{1-6}$ alkyl group (e.g., methyl, ethyl), (3) an optionally substituted $C_{1-6}$ alkoxy group (e.g., methoxy, ethoxy) and (4) an optionally substituted $C_{3-6}$ cycloalkyl group (e.g., cyclopropyl);

$R^1$ and $R^2$ are both hydrogen atoms;
$R^3$ is

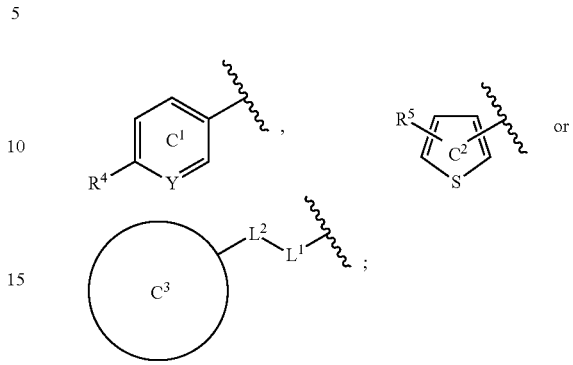

$R^4$ is (1) an optionally substituted $C_{1-6}$ alkyl group (e.g., methyl, ethyl), (2) an optionally substituted $C_{1-6}$ alkoxy group (e.g., methoxy, ethoxy) or (3) a halogen atom (e.g., fluorine atom, chlorine atom);

$R^5$ is (1) an optionally substituted $C_{1-6}$ alkyl group (e.g., methyl, ethyl), (2) an optionally substituted $C_{3-6}$ cycloalkyl group (e.g., cyclopropyl), (3) an optionally substituted $C_{1-6}$ alkoxy group (e.g., methoxy) or (4) a halogen atom (e.g., chlorine atom);

ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy);

$R^6$ is (1) a hydrogen atom, (2) a halogen atom (e.g., fluorine atom, chlorine atom) or (3) an optionally substituted $C_{1-6}$ alkyl group (e.g., methyl);

ring $C^2$ is a thiophene ring optionally further substituted by 1 or 2 (preferably 1) halogen atoms (e.g., chlorine atom);

$L^1$ is an optionally substituted methylene group or NH;
$L^2$ is a bond; and
ring $C^3$ is a thiophene ring or a benzene ring, each of which is optionally further substituted by 1 to 5 (preferably 1 to 3) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy).

[Compound B-a]

Compound (I), wherein ring A is an imidazole ring (that is, $X^1$ is a carbon atom, and $X^2$ is a nitrogen atom), a pyrazole ring (that is, $X^1$ is a nitrogen atom, and $X^2$ is a carbon atom) or a triazole ring (that is, $X^1$ and $X^2$ are both nitrogen atoms), each of which is optionally further substituted by 1 or 2 (preferably 1) substituents selected from a $C_{1-6}$ alkyl group (e.g., methyl, ethyl) and a halogen atom (e.g., bromine atom);

ring B is a benzene ring optionally further substituted by 1 to 3 (preferably 1 or 2) substituents selected from (1) a halogen atom (e.g., fluorine atom, iodine atom), (2) a $C_{1-6}$ alkyl group (e.g., methyl, ethyl) optionally substituted by 1 to 3 (preferably 1 or 2) substituents selected from a halogen atom (e.g., fluorine atom) and a $C_{1-6}$ alkoxy group (e.g., methoxy), (3) a $C_{1-6}$ alkoxy group (e.g., methoxy, ethoxy) and (4) a $C_{3-6}$ cycloalkyl group (e.g., cyclopropyl);

$R^1$ and $R^2$ are both hydrogen atoms;
$R^3$ is

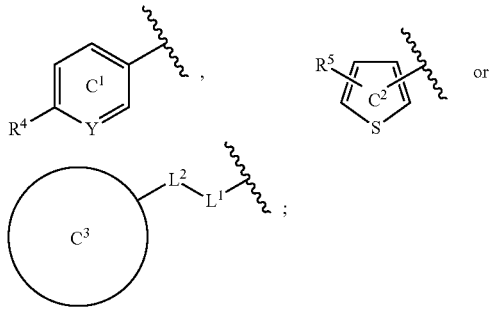, 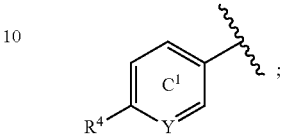 or

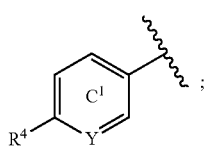;

$R^4$ is (1) a $C_{1-6}$ alkyl group (e.g., methyl, ethyl) optionally substituted by 1 to 3 halogen atoms (e.g., fluorine atom), (2) a $C_{1-6}$ alkoxy group (e.g., methoxy, ethoxy) optionally substituted by 1 to 3 halogen atoms (e.g., fluorine atom) or (3) a halogen atom (e.g., fluorine atom, chlorine atom);

$R^5$ is (1) a $C_{1-6}$ alkyl group (e.g., methyl, ethyl) optionally substituted by 1 to 3 halogen atoms (e.g., fluorine atom), (2) a $C_{3-6}$ cycloalkyl group (e.g., cyclopropyl), (3) a $C_{1-6}$ alkoxy group (e.g., methoxy) or (4) a halogen atom (e.g., chlorine atom);

ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy);

$R^6$ is (1) a hydrogen atom, (2) a halogen atom (e.g., fluorine atom, chlorine atom) or (3) a $C_{1-6}$ alkyl group (e.g., methyl);

ring $C^2$ is a thiophene ring optionally further substituted by 1 or 2 (preferably 1) halogen atoms (e.g., chlorine atom);

$L^1$ is a methylene group or NH;

$L^2$ is a bond; and ring $C^3$ is a thiophene ring or a benzene ring, each of which is optionally further substituted by 1 to 5 (preferably 1 to 3) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy) optionally substituted by 1 to 3 halogen atoms (e.g., fluorine atom).

[Compound A-a-1]

The above-mentioned [Compound A-a], wherein $R^3$ is

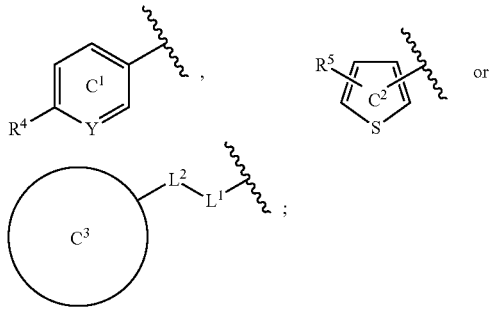;

$R^4$ is (1) an optionally substituted $C_{1-6}$ alkyl group (e.g., methyl, ethyl), (2) an optionally substituted $C_{1-6}$ alkoxy group (e.g., methoxy, ethoxy) or (3) a halogen atom (e.g., fluorine atom, chlorine atom); and ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) an optionally substituted $C_{1-6}$ alkyl group (e.g., methyl) and (3) an optionally substituted $C_{1-6}$ alkoxy group (e.g., methoxy).

[Compound B-a-1]

The above-mentioned [Compound B-a], wherein $R^3$ is

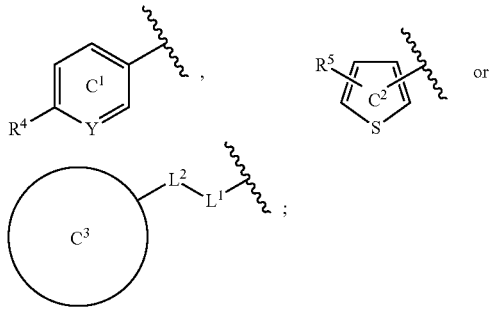;

$R^4$ is (1) a $C_{1-6}$ alkyl group (e.g., methyl, ethyl) optionally substituted by 1 to 3 halogen atoms (e.g., fluorine atom), (2) a $C_{1-6}$ alkoxy group (e.g., methoxy, ethoxy) optionally substituted by 1 to 3 halogen atoms (e.g., fluorine atom) or (3) a halogen atom (e.g., fluorine atom, chlorine atom); and ring $C^1$ is a benzene ring (that is, Y is $CR^6$) or a pyridine ring (that is, Y is N), each of which is optionally further substituted by 1 to 3 (preferably 1 or 2) substituents selected from (1) a halogen atom (e.g., fluorine atom, chlorine atom), (2) a $C_{1-6}$ alkyl group (e.g., methyl) optionally substituted by 1 to 3 halogen atoms (e.g., fluorine atom) and (3) a $C_{1-6}$ alkoxy group (e.g., methoxy).

[Compound B-2-a]

compound (I), wherein ring A is an imidazole ring (that is, $X^1$ is a carbon atom, and $X^2$ is a nitrogen atom) or a pyrazole ring (that is, $X^1$ is a nitrogen atom, and $X^2$ is a carbon atom), each of which is optionally further substituted by 1 or 2 (preferably 1) substituents selected from a $C_{1-6}$ alkyl group (e.g., methyl);

ring B is a benzene ring optionally further substituted by 1 to 3 (preferably 1 or 2) substituents selected from (1) a $C_{1-6}$ alkyl group (e.g., methyl, ethyl) optionally substituted by 1 to 3 (preferably 1 or 2) substituents selected from a $C_{1-6}$ alkoxy group (e.g., methoxy), (2) a $C_{1-6}$ alkoxy group (e.g., methoxy, ethoxy) and (3) a $C_{3-6}$ cycloalkyl group (e.g., cyclopropyl);

$R^1$ and $R^2$ are both hydrogen atoms;

$R^3$ is

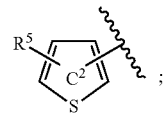;

$R^5$ is (1) a $C_{1-6}$ alkyl group (e.g., methyl, ethyl) optionally substituted by 1 to 3 halogen atoms (e.g., fluorine atom), (2) a $C_{3-6}$ cycloalkyl group (e.g., cyclopropyl), (3) a $C_{1-6}$ alkoxy group (e.g., methoxy) or (4) a halogen atom (e.g., chlorine atom); and ring $C^2$ is a thiophene ring optionally further substituted by 1 or 2 (preferably 1) halogen atoms (e.g., chlorine atom).

[Compound D]

Compound (I), wherein ring A is an imidazole ring (that is, $X^1$ is a carbon atom, and $X^2$ is a nitrogen atom) optionally further substituted by 1 or 2 (preferably 1) substituents selected from a $C_{1-6}$ alkyl group (e.g., methyl);

ring B is a benzene ring optionally further substituted by 1 to 3 (preferably 1 or 2) substituents selected from a $C_{1-6}$ alkyl group (e.g., methyl) and a $C_{1-6}$ alkoxy group (e.g., methoxy);

$R^1$ and $R^2$ are both hydrogen atoms;
$R^3$ is

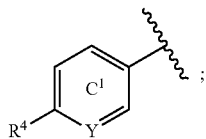 ;

$R^4$ is a $C_{1-6}$ alkoxy group (e.g., methoxy) optionally substituted by 1 to 3 halogen atoms (e.g., fluorine atom);

ring $C^1$ is a benzene ring (that is, Y is $CR^6$) or a pyridine ring (that is, Y is N), each of which is optionally further substituted by 1 to 3 halogen atoms (e.g., fluorine atom); and $R^6$ is (1) a hydrogen atom or (2) a halogen atom (e.g., fluorine atom).

[Compound E]

3,5-Difluoro-4-methoxy-N-((6-methoxy-1-methyl-1H-benzimidazol-7-yl)methyl)benzamide or a salt thereof.

6-(Difluoromethoxy)-N-((1,6-dimethyl-1H-benzimidazol-7-yl)methyl)-5-fluoronicotinamide or a salt thereof.

N-((1,6-dimethyl-1H-benzimidazol-7-yl)methyl)-4-(trifluoromethoxy)benzamide or a salt thereof.

Specific examples of compound (I) include the compounds of the below-mentioned Examples 1-284, and the compounds of Examples 8, 134 and 152 are especially preferable.

As a salt of a compound represented by the formula (I), a pharmacologically acceptable salt is preferable, and examples of such salt include a salt with inorganic base, a salt with organic base, a salt with inorganic acid, a salt with organic acid, and a salt with basic or acidic amino acid.

Preferable examples of the salt with inorganic base include alkali metal salts such as sodium salt, potassium salt and the like, alkaline earth metal salts such as calcium salt, magnesium salt and the like, aluminum salt, and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, and N,N-dibenzylethylenediamine.

Preferable examples of the salt with inorganic acid include salts with hydrogen chloride, hydrogen bromide, nitric acid, sulfuric acid, and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with basic amino acid include salts with arginine, lysine, and ornithine.

Preferable examples of the salt with acidic amino acid include salts with aspartic acid, and glutamic acid.

Compound (I) may be used as a prodrug.

The prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, or t-butylation); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like). Any of these compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, a prodrug may form a salt, and as such salt, those exemplified as a salt of the compound represented by the aforementioned formula (I) can be mentioned.

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and can be useful in the fields of medical diagnosis and the like.

Furthermore, compound (I) may be a hydrate or a non-hydrate, or a non-solvate, or a solvate.

Compound (I) also encompasses a deuterium conversion form wherein $^1$H is converted to $^2$H(D).

Furthermore, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, and stability). The cocrystal and cocrystal salt can be produced by cocrystallization method known per se.

Compound (I) or a prodrug thereof (hereinafter sometimes to be simply abbreviated as the compound of the present invention) can be used as it is or in the form of a pharmaceutical composition (hereinafter sometimes to be abbreviated as the "medicament of the present invention") by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These can be incorporated as excipient, lubricant, binder and disintegrant for solid preparations; or solvent, solubilizing agent, suspending agent, isotonicity agent, buffer and soothing agent for liquid preparations; and the like. Where necessary, preparation additives such as preservative, antioxidant, colorant, sweetening agent and the like can be used.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the aforementioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the medicament of the present invention include oral preparations such as tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film), and parenteral preparations such as injection (e.g., subcutaneous injection, intravenous injection, intramuscular injection, intraperitoneal injection, drip infusion), external preparations such as transdermal absorption type preparation, ointment, lotion, adhesive preparation, suppository (e.g., rectal suppository, vaginal suppository), pellet, nasal preparation, pulmonary preparation (inhalant), eye drop, and the like. The compound of the present invention and the medicament of present invention can be administered orally or parenterally (e.g., intravenous, intraarterial, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be a release control preparation (e.g., sustained-release microcapsule) such as an immediate-release preparation, a sustained-release preparation and the like.

The medicament of the present invention can be produced according to a method conventionally used in the field of pharmaceutical formulation, for example, the method described in the Japanese Pharmacopoeia, and the like.

While the content of the compound of the present invention in the medicament of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, precipitated calcium carbonate, gelatin, gum arabic, pullulan, and carnauba wax may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, and red ferric oxide may also be used during coating.

The compound of the present invention has an antagonistic action on an NMDA receptor containing the NR2B subunit. As used herein, the antagonistic action on an NMDA receptor containing the NR2B subunit is confirmed by, for example, a suppressive effect on the receptor activation (e.g., glutamic acid-induced intracellular calcium ion ($Ca^{2+}$) influx).

The NMDA receptor containing the NR2B subunit is a receptor composed of four subunits in total including one NR2B subunit, and further, three subunits of 2 or 3 kinds selected from NR1, NR2A, NR2B, NR2C, NR2D, NR3A and NR3B.

The NMDA receptor containing the NR2B subunit is preferably a receptor composed of four subunits including a heterodimer of NR1 and NR2B, and a heterodimer of NR1 and one subunit selected from NR2A, NR2B, NR2C and NR2D.

The NMDA receptor containing the NR2B subunit is more preferably a receptor composed of four subunits including 2 sets of heterodimers of NR1 and NR2B.

Since the compound of the present invention is expected to show low toxicity (e.g., acute toxicity, chronic toxicity, genetic toxicity, reproductive toxicity, pulmonary toxicity, carcinogenicity) and less side effects, it can be used as a prophylactic or therapeutic agent, or diagnostic agent for various diseases in mammals.

The compound of the present invention is also expected to show a low genetic toxicity risk.

The compound of the present invention can be used as a prophylactic or therapeutic agent for central and peripheral diseases. For example, the compound of the present invention can be useful as an agent for the prophylaxis or treatment of various diseases such as (1) psychiatric diseases [e.g., depression, major depression, minor depressive disorder, bipolar depression, dysthymic disorder, emotional disorder (seasonal affective disorder and the like), recurrent depression, postpartum depression, stress disorder, major depressive disorder concomitant with psychosis (including delusive disorders and schizophrenia), manic or mixed mood episode, hypomanic mood episode, depression episode with atypical features, depression episode with melancholic features, depressive episodes with tonic features, depression episode after stroke, delirium, peripheral symptoms of dementia (mental symptoms or behavior abnormalities), anxiety, generalized anxiety disorder, anxiety syndrome, mood disorder, cyclothymic disorder, premenstrual dysphoric disorder, panic disorder, phobia, social phobia, social anxiety disorder, obsessive disorder, post-traumatic stress syndrome, post-traumatic stress disorder, delusions or depression-type schizoaffective disorder, delusive personality disorder, Tourette syndrome, autism, fragile X syndrome, Rett syndrome, adjustment disorder, bipolar disorder (including type I bipolar disorder and type II bipolar disorder), neurosis, schizophrenia (e.g., positive symptom, negative symptom, memory disorders, delusional schizophrenia, disorganized schizophrenia, tension type schizophrenia, undifferentiated schizophrenia, remnant type schizophrenia), schizophreniform disorder, chronic fatigue syndrome, anxiety neurosis, compulsive neurosis, panic disorder, epilepsy, anxiety, anxious mental state, emotional abnormality, cyclothymia, nervous erethism, faint, addiction, low sex drive, attention deficit hyperactivity disorder (ADHD), refractory major depression, treatment-resistant depression, psychotic disturbance (e.g., short-term psychotic disorder, shared psychotic disorder), psychosis induced by alcohol, amphetamine, cannabis, cocaine, hallucinogen, obesity, inhalation medicine, opioids or phencyclidine, delusional disorder, Noonan syndrome, Angelman syndrome, Prader-Willi syndrome, Beckwith-Wiedemann syndrome, Silver-Russell syndrome, tuberous sclerosis, Williams syndrome, Kallmann syndrome, Rubinstein-Taybi syndrome], movement disorder, mental retardation, paranoid tendency, (2) neurodegenerative diseases [e.g., Alzheimer's disease, Alzheimer-type senile dementia, Parkinson's disease, Huntington's disease, multi-infarct dementia, frontotemporal dementia, frontotemporal dementia Parkinson's Type, alcoholic dementia or other drug related dementia, dementia associated with intracranial tumor or brain trauma, Dementia associated with Huntington's disease or Parkinson's disease, neurodegeneration accompanying brain trauma, neurodegeneration accompanying stroke, neurodegeneration accompanying cerebral infarction, neurodegeneration associated with hypoglycemia, neurodegeneration accompanying epileptic seizures, neurodegeneration accompanying neurotoxicosis, multiple system atrophy, spinal cord injury, Aids-related dementia, progressive supranuclear palsy, Pick's syndrome, Niemann-Pick syndrome, corticobasal degeneration, Down's syndrome, vascular dementia, post-encephalitic parkinsonism, dementia with Lewy bodies, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis, neuromyopathy], (3) amnestic disorder, mild cognitive impairment, learning disability (e.g., reading disturbance, arithmetic disorder, dysgraphia), age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) pain [e.g., psychogenic pain (somatoform disorder, pain disorder, somatization disorder, hypochondriasis, conversion disorder, chronic pain accompanied by depression), inflammatory pain, peripheral neuropathic pain, central neuropathic pain, neuropathic pain, acute pain, intractable pain, cancerous continuous pain, cancerous breakthrough pain, cancer pain, continuous pain, physical pain, breakthrough pain, chronic pain, tenderness, generalized pain, dull pain, dermatological pain, radiation pain, pain, postoperative thoracotomy pain syndrome], (7) deafness [e.g., kanamycin deafness, streptomycin deafness, toxic deafness, senile deafness, idiopathic bilateral sensorineural hearing loss, sudden deafness, acquired deaf mutism, genetic deafness, organic deafness, high-tone sensorineural hearing loss, occupational hearing loss, occupational hearing loss, low-tone sensorineural hearing loss], (8) traumatic brain injury, and disorder or complication associated therewith, post concussive syndrome, shaken baby syndrome, cerebral apoplexy, age-related macular degeneration, oculopalatal tremor, convulsions, phantom limb pain, radiation somnolence syndrome, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug abuse, drug dependence, drug withdrawal, migraine, stress headache, catatonic headache, diabetic neuropathy, obesity, diabetes, muscular convulsions, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, diarrhea, constipation, postoperative ileus, and the like.

Particularly, the compound of the present invention can be useful for the prophylaxis or treatment of major depression, bipolar disorder, migraine, pain or peripheral symptoms of dementia.

Both major depression and bipolar disorder are classified as mood disorder, and are diseases showing depression state or depression state and manic state for a long term. In recent years, it has been found that continuous intravenous administration of ketamine, an NMDA receptor antagonist, improves depression symptom accompanying major depression and bipolar disorder rapidly and in a sustained manner (Therapeutic Advances in Psychopharmacology (Ther. Adv. Psychopharmacol.), vol. 4, pp. 75-99, 2014). It has also been reported that continuous intravenous administration of CP-101, 606, which are antagonists of NMDA receptor containing the NR2B subunit significantly improves treatment resistant-depression symptom (Journal of Clinical Psychopharmacology (J. Clin. Psychopharmacol.), vol. 28, pp. 631-637, 2008). Therefore, the compound of the present invention is promising as a prophylactic or therapeutic drug for treatment resistant-depression disease.

Migraine is a chronic and paroxysmal primary headache. While the onset mechanism is unknown, it is considered to be developed along with abnormalities of central nervous system process, abnormalities of trigeminal nerve blood vessel system and the like. In pathophysiology study of migraine, particularly aura thereof, a cortical spreading depression phenomenon is attracting attention. It has been reported that CP-101, 606 and Ro25-6981, which are antagonists of NMDA receptor containing the NR2B subunit, suppress the number of occurrence and the depth of cortical spreading depression in an experimental cortical spreading depression test using rodents (the Journal of Pharmacology and Experimental Therapeutics (J. Pharmacol. Exp. Ther.), vol. 321, pp. 564-572, 2007). Therefore, the compound of the present invention is promising as a prophylactic or therapeutic drug for migraine.

Pain is classified into acute pain whose pain lasts for a comparatively short period of time, and chronic pain accompanying retention or recurrence for 3 months or longer, retention for not less than one month after recovery of acute tissue injury, or an unhealed lesion. An NMDA receptor containing the NR2B subunit is highly expressed in posterior horn of spinal cord which plays an important role in the acceptance of pain, and functional control thereof is suggested to enable pain control. In fact, a genetic modification operation that causes functional decline of NR2B subunit has been reported to elevate the pain sense threshold (European Journal of Neuroscience (Eur. J. Neurosci.), vol. 32, pp. 798-810, 2010). Also, it has been reported that the pain sense threshold increases due to Ifenprodil as an antagonist of an NMDA receptor containing the NR2B subunit (Pain, vol. 153, pp. 1022-1029, 2012). Therefore, the compound of the present invention is promising as a prophylactic or therapeutic drug for pain.

Dementia refers to chronic, general, and generally irreversible decline of cognition. While the degradation of quality of life of patients due to the cognitive decline is remarkable, peripheral symptoms of dementia (psychological symptom or abnormal behavior) is also considered to be a factor markedly influencing the degradation of quality of life of patients and caregiver thereof. An effective therapeutic intervention method for peripheral symptoms of dementia has not been established; however, it has been reported that administration of memantine, which is an NMDA receptor antagonist, partially improves peripheral symptoms of dementia (Annals of Pharmacotherapy (Ann. Pharmacother.), vol. 42, pp. 32-38, 2007). While NMDA receptor containing the NR2B subunit is widely distributed in the brain except cerebellum, peripheral symptoms of dementia has been reported to be related to white matter abnormality of brain region except cerebellum (Journal of the Neurological Sciences (J. Neurol. Sci.), vol. 337, pp. 162-166, 2014). Therefore, the compound of the present invention is promising as a prophylactic or therapeutic drug for peripheral symptoms of dementia.

While the dose of the compound of the present invention can vary depending on the subject of administration, administration route, target disease, symptom and the like, for example, when the compound of the present invention is administered orally or parenterally to an adult patient, its dose can be, for example, generally about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other active ingredients (hereinafter to be abbreviated as concomitant drug).

Examples of the concomitant drug include the following. Acetylcholine esterase inhibitor (e.g., donepezil, rivastigmine, galanthamine, zanapezil), antidementia agent (e.g., memantine), inhibitor of β amyloid protein production, secretion, accumulation, aggregation and/or deposition, P secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), other therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation/regeneration promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying antirheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil(citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, $5\text{-}HT_{1A}$ agonist (buspirone hydrochloride, tandospirone citrate, osemozotan hydrocloride etc.), $5\text{-}HT_{2A}$ antagonist, $5\text{-}HT_{2A}$ inverse agonist, $5\text{-}HT_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), antiobesity drug, therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent, antibody medicament, nucleic acid or nucleic acid derivative, aptamer drug and the like.

Two or more kinds of the above-mentioned concomitant drugs may be used in combination at an appropriate ratio.

When the compound of the present invention is applied to each of the above-mentioned diseases, it can also be used in combination with biologics (e.g., antibody medicament, nucleic acid or nucleic acid derivative, aptamer medicament, vaccine preparation), or can be used in combination with a gene therapy method and the like, or can also be used in combination with a treatment in psychiatric field without using drugs.

Examples of the antibody medicament and vaccine preparation include vaccine preparation against angiotensin II, vaccine preparation against CETP, CETP antibody, antibody against TNFα antibody and other cytokines, amyloid P vaccine preparation, vaccine for type 1 diabetes (e.g., DIA-PEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to a enzyme or protein involved in blood lipid metabolism (e.g., a gene relating to metabolism, excretion and absorption of cholesterol or triglyceride or HDL-cholesterol or blood phospholipid), a treatment method using a gene relating to a enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of the administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of the concomitant drug in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of additives such as a carrier and the like in the combination agent of the present invention differs depending on the form of a preparation, and usually from about 1 to 99.99 wt %, preferably from about 10 to 90 wt %, based on the whole preparation.

When the compound of the present invention and a concomitant drug are separately formulated into preparations, the contents thereof are similar to the above.

The production method of the compound of the present invention is explained in the following.

The starting materials and reagents used in each step in the following production method, and the obtained compounds each may form a salt. Examples of the salt include those similar to the aforementioned salts of the compound represented by the formula (I) and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature −300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic hetero ring such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5, 6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride or a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a halogenated alkyl form from alcohol by reacting with triphenylphosphine- and carbon tetrachloride or carbon tetrabromide, and the like may be used. Alternatively, a method of synthesizing a halogenated alkyl form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of tert-butyl ester is performed, formic acid, triethylsilane and the like are sometimes added to reductively trap the by-produced tert-butyl cation.

When a dehydrating reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Compound (I) can be produced from compound (1) by the following Production step A.

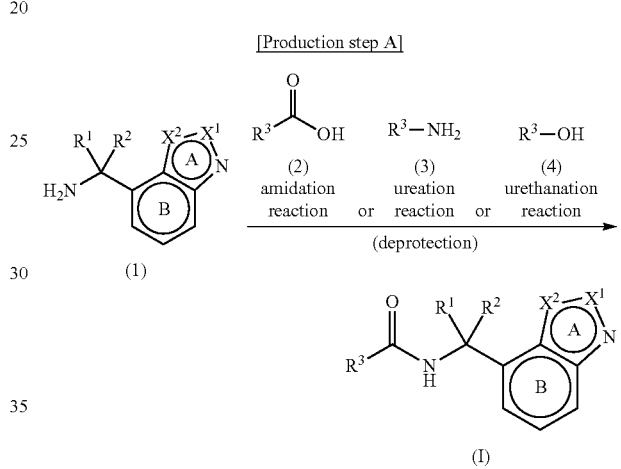

wherein ring A, ring B, $X^1$, $X^2$, $R^1$, $R^2$ and $R^3$ are as defined above.

Compound (I) can be produced by an amidation reaction of compound (1) and compound (2). As the amidation reagent, 1-ethyl-3-(3-dimethylaminopropyl)carbodiimide, 0-(7-aza benzotriazol-1-yl)-N,N,N',N'-tetramethyluronium hexafluorophosphate and the like can be mentioned. Also, compound (I) can be produced by a ureation reaction of compound (1) and compound (3). As the ureation reagent, 1,1'-carbonylbis-1H-imidazole, triphosgene and the like can be mentioned. Furthermore, compound (I) can be produced by a urethanation reaction of compound (1) and compound (4). As the urethanation reagent, 1,1'-carbonylbis-1H-imidazole, triphosgene and the like can be mentioned.

Compound (1) can be produced from compound (5) according to the following Production step B.

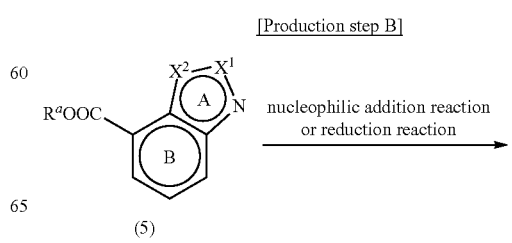

-continued

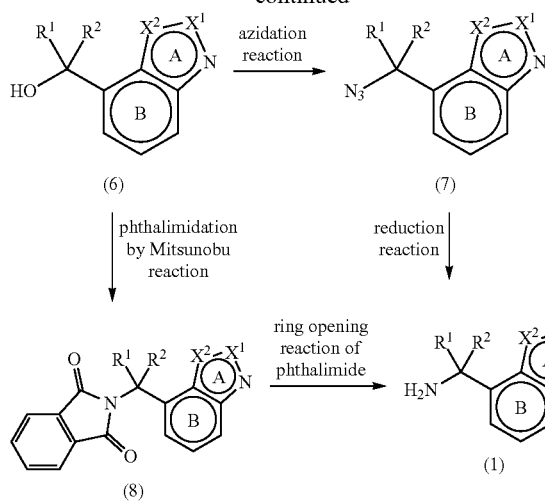

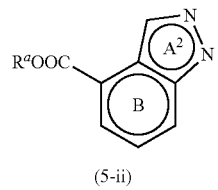

(5-ii)

wherein $R^a$ is a $C_{1-6}$ alkyl group, ring A2 is a pyrazole ring having a substituent, and ring B is as defined above.

As the "pyrazole ring having a substituent" represented by ring $A^2$, those exemplified as the "optionally substituted pyrazole ring" for ring A (excluding unsubstituted pyrazole ring) can be mentioned.

Compound (5-i) can be produced by a cyclization reaction of compound (9). As the reagent to be used for the cyclization reaction, sodium nitrite and the like can be mentioned. Compound (5-ii) can be produced by an alkylation reaction or a protecting group introduction reaction of compound (5-i). As the alkylation reagent, alkyl halide and the like can be mentioned. As the protecting group, a 2-tetrahydropyranyl group, a tert-butoxycarbonyl group and the like can be mentioned, As the reagent to be used, 3,4-dihydro-2H-pyran, di-tert-butyl dicarbonate and the like can be mentioned.

Among compounds (5), the following compound (5-iii) and compound (5-iv) can be produced from compound (10) according to the following Production step D.

wherein $R^a$ is a $C_{1-6}$ alkyl group, and ring A, ring B, $X^1$, $X^2$, $R^1$ and $R^2$ are as defined above.

Compound (6) can be produced by a nucleophilic addition reaction of compound (5). As the reagent to be used, organic lithiums, Grignard reagent and the like can be mentioned. Compound (6) wherein $R^1$, $R^2$=H can be produced by a reduction reaction of compound (5). As the reagent to be used, lithium aluminum hydride and the like can be mentioned. Compound (7) can be produced by an azidation reaction of compound (6). As the azidation reagent, diphenylphosphoryl azide and the like can be mentioned. Compound (1) can be produced by a reduction reaction of compound (7). As the reagent to be used, triphenylphosphine and the like can be mentioned. Compound (8) can be produced by a Mitsunobu reaction of compound (6) and phthalimide. As the reagent to be used for the Mitsunobu reaction, diethyl azodicarboxylate, triphenylphosphine and the like can be mentioned. Compound (1) can also be produced by a ring opening reaction of phthalimide of compound (8). As the reagent to be used, hydrazine monohydrate and the like can be mentioned.

Among compounds (5), the following compound (5-i) and compound (5-ii) can be produced from compound (9) according to the following Production step C.

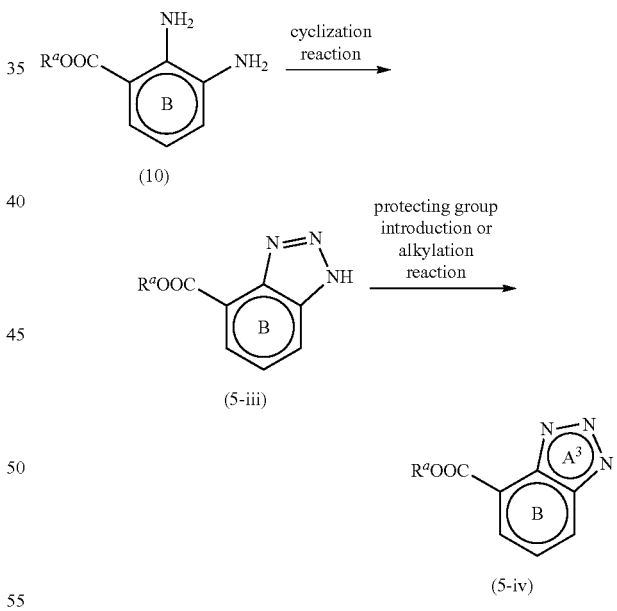

[Production step D]

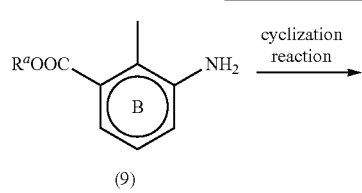

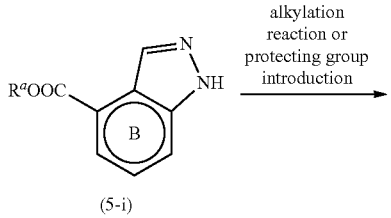

wherein $R^a$ is a $C_{1-6}$ alkyl group, ring A3 is a triazole ring having a substituent, and ring B is as defined above.

As the "triazole ring having a substituent" represented by ring $A^3$, those exemplified as the "optionally substituted triazole ring" for ring A (excluding unsubstituted triazole ring) can be mentioned.

Compound (5-iii) can be produced by a cyclization reaction of compound (10). As the reagent to be used for the cyclization reaction, sodium nitrite and the like can be mentioned. Compound (5-iv) can be produced by an alkylation reaction or a protecting group introduction reaction of compound (5-iii). As the alkylation reagent, alkyl halide and the like can be mentioned. As the protecting group, 2-tetrahydropyranyl group, tert-butoxycarbonyl group and the like can be mentioned. As the reagent to be used, 3,4-dihydro-2H-pyran, di-tert-butyl dicarbonate and the like can be mentioned.

Among compounds (5), the following compound (5-v) can be produced from compound (11) according to the following Production step E.

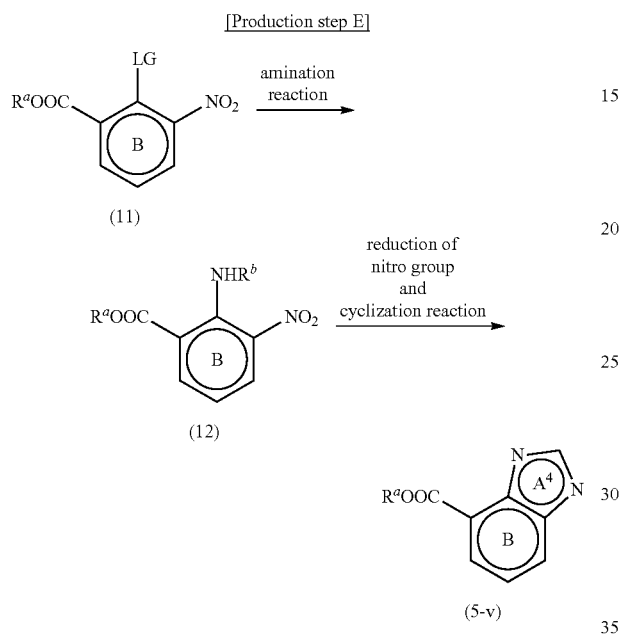

wherein $R^a$ is a $C_{1-6}$ alkyl group, $NHR^b$ is an optionally substituted amino group, ring $A^4$ is an optionally substituted imidazole ring, ring B is as defined above, and LG is a "leaving group".

Examples of the "leaving group" for LG include a halogen atom (e.g., fluorine atom, chlorine atom, bromine atom, iodine atom etc.), an optionally halogenated $C_{1-6}$ alkylsulfonyloxy group (e.g., methanesulfonyloxy, ethanesulfonyloxy, trifluoromethanesulfonyloxy), and an optionally substituted $C_{6-14}$ arylsulfonyloxy group [e.g., $C_{6-14}$ arylsulfonyloxy group optionally having 1 to 3 substituents selected from $C_{1-6}$ alkyl group (e.g., methyl), $C_{1-6}$ alkoxy group (e.g., methoxy) and nitro group; specific examples include benzenesulfonyloxy, m-nitrobenzenesulfonyloxy, p-toluenesulfonyloxy, naphthylsulfonyloxy].

As the "optionally substituted imidazole ring" represented by ring $A^4$, those exemplified as the "optionally substituted imidazole ring" for ring A can be mentioned.

Compound (12) can be produced by an amination reaction of compound (11). As the amination reagent, alkylamine and the like can be mentioned. Compound (5-v) can be produced by reduction of a nitro group and a subsequent cyclization reaction of compound (12). As the reagent to be used for the reduction of the nitro group, zinc, iron and the like can be mentioned. As the reagent to be used for the cyclization reaction, formic acid, acetic acid and the like can be mentioned.

In the thus-obtained compound (I), an intramolecular functional group can also be converted to an object functional group by combining chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production method can be isolated and purified by a known means, such as solvent extraction, pH change of solution, phase transfer, crystallization, recrystallization, chromatography and the like.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se.

Compound (I) may be a crystal.

A crystal of compound (I) (hereinafter sometimes to be abbreviated as the crystal of the present invention) can be produced by crystallization, by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy), and is expected to be useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Unless particularly indicated, the elution in column chromatography in the Examples was performed under observation by TLC (Thin Layer Chromatography). For TLC observation, 60F$_{254}$ manufactured by Merck was used as a TLC plate, and the solvent used as an elution solvent for column chromatography was used as developing solvent. For detection, moreover, a UV detector was adopted. In silica gel column chromatography, the indication of NH means use of aminopropylsilane-bonded silica gel, Diol means use of 3-(2,3-dihydroxypropoxy)propylsilane-bonded silica gel. In preparative HPLC (high performance liquid chromatography), the indication of C18 means use of octadecyl-bonded silica gel. The ratio shown for elution solvents is, unless otherwise specified, a volume mixing ratio.

$^1$H NMR was measured by Fourier-transform NMR. For the analysis of $^1$H NMR, ACD/SpecManager (trade name) software and the like were used. Very mild peaks for protons of a hydroxy group, an amino group and the like are sometimes not described.

MS was measured by LC/MS. As ionization method, ESI method, or APCI method was used. The data indicates those found. Generally, molecular ion peaks are observed; however, they may be observed as a fragment ion. In the case of a salt, generally, a molecular ion peak or a fragment ion peak of a free form is observed.

The unit of sample concentration (c) in optical rotation ($[\alpha]_D$) is g/100 mL.

The elemental analytical value (Anal.) shows Calculated value (Calcd) and Found value (Found).

The peak in the powder X-ray diffraction in the Examples means a peak measured by Ultima IV (Rigaku Corporation, Japan) at room temperature using Cu Kα radiation as a radiation source. The measurement conditions were as follows.

Electric pressure/Electric current: 40 kV/50 mA
Scan speed: 6 degree/min
Scan range of 2 Theta: 2-35 degree The crystallinity by powder X-ray diffraction in the Examples was calculated by the Hermans method.

In the following Examples, the following abbreviations are used.
mp: melting point
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
DPPA: diphenylphosphoryl azide
TFA: trifluoroacetic acid
DMAP: N,N-dimethyl-4-aminopyridine
DMA: N,N-dimethylacetamide
DMF: N,N-dimethylformamide
HOBt: 1H-benzotriazol-1-ol
HOBt·$H_2O$: 1H-benzotriazol-1-ol monohydrate
THF: tetrahydrofuran
WSC·HCl: N-(3-(dimethylamino)propyl)-N'-ethylcarbodiimide hydrochloride
DBU: 2,3,4,6,7,8,9,10-octahydropyrimido[1,2-a]azepine Example 1

N-((2,5-dimethyl-2H-indazol-4-yl)methyl)-4-(trifluoromethoxy)benzamide

A) methyl 3-amino-6-bromo-2-methylbenzoate

To a mixture of methyl 3-amino-2-methylbenzoate (10 g), acetic acid (100 mL) and methanol (200 mL) was added bromine (10 g) at 0° C. To the mixture was added 1 M aqueous sodium thiosulfate solution at 0° C., and the reaction mixture was concentrated. The obtained residue was partitioned with an ethyl acetate-saturated aqueous sodium hydrogen carbonate solution, and the organic layer was washed with saturated brine, dried over anhydrous magnesium sulfate and concentrated under reduced pressure. The residue was purified by silica gel column chromatography (ethyl acetate/hexane) to give the title compound (7.3 g).

$^1$H NMR (300 MHz, $CDCl_3$) δ 2.09 (3H, s), 3.70 (2H, brs), 3.94 (3H, s), 6.59 (1H, d, J=8.6 Hz), 7.19 (1H, d, J=8.6 Hz).

B) methyl 5-bromo-1H-indazole-4-carboxylate

To a mixture of methyl 3-amino-6-bromo-2-methylbenzoate (7.2 g) and acetic acid (150 mL) was added a solution of sodium nitrite (2.2 g) in water (15 mL) at room temperature, and the mixture was stirred at room temperature for 3 hr and concentrated. The obtained residue was partitioned with an ethyl acetate-saturated aqueous sodium hydrogen carbonate solution, and the organic layer was washed with water, dried over anhydrous magnesium sulfate and concentrated under reduced pressure. The obtained solid was crystallized from ethyl acetate/hexane to give the title compound (4.9 g).

$^1$H NMR (300 MHz, DMSO-$d_6$) δ 3.98 (3H, s), 7.58-7.66 (1H, m), 7.67-7.73 (1H, m), 8.18 (1H, d, J=0.9 Hz), 13.56 (1H, brs).

C) methyl 5-bromo-2-methyl-2H-indazole-4-carboxylate

To a mixture of methyl 5-bromo-1H-indazole-4-carboxylate (2.0 g) and ethyl acetate (50 mL) was added trimethyloxonium tetrafluoroborate (1.5 g) at room temperature, and the mixture was stirred at room temperature for 3 hr. To the mixture was added saturated aqueous sodium hydrogen carbonate solution, and the mixture was extracted with ethyl acetate. The organic layer was separated, washed with saturated brine, dried over anhydrous magnesium sulfate and concentrated under reduced pressure. The obtained solid was crystallized from ethyl acetate/hexane to give the title compound (1.6 g).

$^1$H NMR (300 MHz, DMSO-$d_6$) δ 3.95 (3H, s), 4.20 (3H, s), 7.49 (1H, d, J=9.1 Hz), 7.75 (1H, dd, J=9.1, 0.9 Hz), 8.52 (1H, s).

D) methyl 2,5-dimethyl-2H-indazole-4-carboxylate

A mixture of methyl 5-bromo-2-methyl-2H-indazole-4-carboxylate (1.4 g), trimethylboroxine (2.0 g), [1,1'-bis(diphenylphosphino)ferrocene]dichloropalladium(II) (0.38 g), tripotassium phosphate.7 hydrate (2.2 g) and 1,2-dimethoxyethane (20 mL) was refluxed under an argon gas atmosphere for 5 hr. To the reaction mixture was added water, and the mixture was extracted with ethyl acetate. The extract was washed with water, dried over anhydrous magnesium sulfate, and concentrated under reduced pressure. The residue was purified by silica gel column chromatography (hexane/ethyl acetate) to give the title compound (1.0 g).

MS: $[M+H]^+$ 205.0.

E) (2,5-dimethyl-2H-indazol-4-yl)methanol

To a mixture of lithium aluminum hydride (0.37 g) and THF (15 mL) was added a solution of methyl 2,5-dimethyl-2H-indazole-4-carboxylate (1.0 g) in THF (5 mL) at 0° C., and the mixture was stirred under a nitrogen atmosphere at 0° C. for 2 hr. To the mixture was added ice water, and the mixture was extracted with ethyl acetate. Insoluble material was filtered off and the filtrate was washed with saturated brine, dried over anhydrous magnesium sulfate, and concentrated under reduced pressure to give the title compound (0.61 g).

MS: $[M+H]^+$ 177.1.

F) 4-(azidomethyl)-2,5-dimethyl-2H-indazole

To a mixture of (2,5-dimethyl-2H-indazol-4-yl)methanol (0.60 g), DBU (0.78 g) and DMF (15 mL) was added DPPA (1.4 g) at 0° C., and the mixture was stirred at room temperature for 3 hr. To the mixture was added water, and the mixture was extracted with ethyl acetate. The organic layer was separated, washed with water, dried over anhydrous magnesium sulfate, and concentrated under reduced pressure to give the title compound (0.68 g).
MS: [M+H]+ 202.1.

G) 1-(2,5-dimethyl-2H-indazol-4-yl)methanamine hydrochloride

A mixture of 4-(azidomethyl)-2,5-dimethyl-2H-indazole (680 mg), 10% palladium-carbon (720 mg) and methanol (10 mL) was stirred at normal pressure under a hydrogen atmosphere at room temperature for 3 hr. The catalyst was filtered off, and the filtrate was concentrated under reduced pressure. To a mixture of the residue and ethyl acetate (5 mL) was added 4.0 M hydrogen chloride ethyl acetate solution (2.5 mL). The precipitated solid was collected by filtration and washed with ethyl acetate to give the title compound (710 mg).
$^1$H NMR (300 MHz, DMSO-$d_6$) δ 2.43 (3H, s), 4.17 (3H, s), 4.20-4.26 (2H, m), 7.14 (1H, d, J=8.8 Hz), 7.54 (1H, d, J=9.2 Hz), 8.30-8.40 (2H, m), 8.51 (1H, s).

H) N-((2,5-dimethyl-2H-indazol-4-yl)methyl)-4-(trifluoromethoxy)benzamide

To a mixture of 4-(trifluoromethoxy)benzoic acid (100 mg) and DMF (5 mL) were added HOBt·H$_2$O (89 mg), WSC·HCl (110 mg), 1-(2,5-dimethyl-2H-indazol-4-yl)methanamine hydrochloride (110 mg) and triethylamine (150 mg) at room temperature, and the mixture was stirred overnight. The mixture was neutralized with a saturated aqueous sodium hydrogen carbonate solution and the precipitated solid was collected by filtration to give the title compound (65 mg).
$^1$H NMR (300 MHz, DMSO-$d_6$) δ 2.43 (3H, s), 4.12 (3H, s), 4.69 (2H, d, J=5.4 Hz), 7.07 (1H, d, J=8.9 Hz), 7.39-7.47 (3H, m), 7.98 (2H, d, J=7.8 Hz), 8.32 (1H, s), 8.93 (1H, t, J=4.9 Hz).

Example 2

N-((5-methyl-1H-indazol-4-yl)methyl)-4-(trifluoromethoxy)benzamide

A) 1-tert-butyl 4-methyl 5-bromo-1H-indazole-1,4-dicarboxylate

To a mixture of methyl 5-bromo-1H-indazole-4-carboxylate (1.9 g), triethylamine (0.88 g), DMAP (0.089 g) and THF (20 mL) was added di-tert-butyl dicarbonate (1.7 g) at room temperature, and the mixture was stirred at room temperature for 3 hr. To the mixture was added water, and the mixture was extracted with ethyl acetate. The organic layer was separated, washed with water, dried over anhydrous magnesium sulfate and concentrated under reduced pressure. The residue was purified by silica gel column chromatography (ethyl acetate/hexane) to give the title compound (2.5 g).
$^1$H NMR (300 MHz, CDCl$_3$) δ 1.73 (9H, s), 4.06 (3H, s), 7.77 (1H, d, J=8.9 Hz), 8.20 (1H, d, J=9.0 Hz), 8.35 (1H, d, J=0.8 Hz).

B) 1-tert-butyl 4-methyl 5-methyl-1H-indazole-1,4-dicarboxylate

A mixture of 1-tert-butyl 4-methyl 5-bromo-1H-indazole-1,4-dicarboxylate (1.0 g), trimethylboroxine (1.1 g), [1,1'-bis(diphenylphosphino)ferrocene]dichloropalladium(II) (0.21 g), tripotassium phosphate.7 hydrate (1.2 g) and 1,2-dimethoxyethane (15 mL) was refluxed under an argon gas atmosphere for 5 hr. To the reaction mixture was added water, and the mixture was extracted with ethyl acetate. The extract was washed with water, dried over anhydrous magnesium sulfate, and concentrated under reduced pressure. The residue was purified by silica gel column chromatography (hexane/ethyl acetate) to give the title compound (0.66 g).
MS: [M+H−Boc]+ 1911

C) (5-methyl-1H-indazol-4-yl)methanol

To a mixture of lithium aluminum hydride (130 mg) and THF (5 mL) was added a solution of 1-tert-butyl 4-methyl 5-methyl-1H-indazole-1,4-dicarboxylate (650 mg) in THF (dry) (5 mL) at 0° C., and the mixture was stirred under a nitrogen atmosphere at 0° C. overnight. To the mixture was added ice water, insoluble material was filtered off, and the filtrate was extracted with ethyl acetate, washed with saturated brine, and dried over anhydrous magnesium sulfate. The residue was purified by silica gel column chromatography (ethyl acetate/hexane) to give the title compound (130 mg).
MS: [M+H]+ 163.1.

D) 4-(azidomethyl)-5-methyl-1H-indazole

To a mixture of (5-methyl-1H-indazol-4-yl)methanol (120 mg), DBU (170 mg) and DMF (3 mL) was added DPPA (310 mg) at 0° C. and the mixture was stirred at room temperature overnight. To the mixture was added water, and the mixture was extracted with ethyl acetate. The organic layer was separated, washed with water, dried over anhydrous magnesium sulfate, and concentrated under reduced pressure. The residue was purified by silica gel column chromatography (ethyl acetate/hexane) to give the title compound (60 mg).
MS: [M+H]+ 188.1.

E) N-((5-methyl-1H-indazol-4-yl)methyl)-4-(trifluoromethoxy)benzamide

A mixture of 4-(azidomethyl)-5-methyl-TH-indazole (60 mg), 10% palladium-carbon (34 mg) and methanol (2 mL) was stirred at normal pressure under a hydrogen atmosphere at room temperature for 3 hr. The catalyst was filtered off, and the filtrate was concentrated under reduced pressure to give 1-(5-methyl-1H-indazol-4-yl)methanamine (50 mg). The obtained 1-(5-methyl-1H-indazol-4-yl)methanamine (47 mg) was added to a mixture of 4-(trifluoromethoxy)benzoic acid (60 mg), HOBt·H$_2$O (54 mg), WSC·HCl (67 mg) and DMF (5 mL) at room temperature, and the mixture was stirred overnight. To the mixture was added saturated aqueous sodium hydrogen carbonate solution, and the mixture was extracted with ethyl acetate. The organic layer was separated, washed with water, dried over anhydrous magnesium sulfate and concentrated under reduced pressure. The residue was purified by silica gel column chromatography (ethyl acetate/hexane) to give the title compound (35 mg).
$^1$H NMR (300 MHz, DMSO-$d_6$) δ 2.46 (3H, s), 4.77 (2H, d, J=5.5 Hz), 7.17 (1H, d, J=8.5 Hz), 7.35 (1H, d, J=8.5 Hz), 7.44 (2H, d, J=8.0 Hz), 7.98 (2H, d, J=7.8 Hz), 8.17 (1H, s), 9.04 (1H, t, J=5.4 Hz), 12.92 (1H, s).

Example 3

N-((5-methyl-1H-benzimidazol-4-yl)methyl)-4-(trifluoromethoxy)benzamide

A) 2-acetamido-6-methylbenzoic acid

To a mixture of 2-amino-6-methylbenzoic acid (10 g), sodium hydroxide (3.3 g) and water (200 mL) was added acetic anhydride (8.4 g) at room temperature, and the mixture was stirred at room temperature overnight. The mixture was neutralized with 1N hydrochloric acid at 0° C., and the precipitated solid was collected by filtration, and washed with water to give the title compound (11 g).

$^1$H NMR (300 MHz, DMSO-$d_6$) δ 2.00 (3H, s), 2.33 (3H, s), 7.05 (1H, d, J=7.5 Hz), 7.29 (1H, t, J=7.7 Hz), 7.40 (1H, d, J=8.1 Hz), 9.60 (1H, brs), 13.13 (1H, brs).

B) methyl 2-acetamido-6-methylbenzoate

To a mixture of 2-acetamido-6-methylbenzoic acid (11 g), potassium carbonate (9.4 g) and DMF (150 mL) was added iodomethane (9.7 g) at room temperature, and the mixture was stirred at room temperature overnight. To the mixture was added water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (9.6 g).

$^1$H NMR (300 MHz, DMSO-$d_6$) δ 1.98 (3H, s), 2.29 (3H, s), 3.77 (3H, s), 7.07 (1H, d, J=7.2 Hz), 7.24-7.30 (1H, m), 7.29-7.38 (1H, m), 9.62 (1H, brs).

C) methyl 6-acetamido-3-bromo-2-methylbenzoate

To a mixture of methyl 2-acetamido-6-methylbenzoate (7.0 g) and acetic acid (75 mL) was added bromine (11 g) at room temperature, and the mixture was stirred at room temperature overnight. The reaction mixture was concentrated, the obtained residue was partitioned with an ethyl acetate-saturated aqueous sodium hydrogen carbonate solution, and the organic layer was washed with saturated brine, dried over anhydrous magnesium sulfate and concentrated under reduced pressure to give the title compound (6.8 g).

$^1$H NMR (300 MHz, DMSO-$d_6$) δ 1.99 (3H, s), 2.31 (3H, s), 3.81 (3H, s), 7.26 (1H, d, J=8.7 Hz), 7.68 (1H, d, J=8.7 Hz), 9.63 (1H, brs).

D) methyl 2-acetamido-5-bromo-6-methyl-3-nitrobenzoate

To a mixture of methyl 6-acetamido-3-bromo-2-methylbenzoate (5.0 g) and TFA (50 mL) was added nitric acid (2.2 g) at 0° C., and the mixture was stirred at room temperature overnight. To the mixture was added water, and the mixture was extracted with ethyl acetate. The organic layer was separated, washed with saturated aqueous sodium hydrogen carbonate solution, dried over anhydrous magnesium sulfate and concentrated under reduced pressure. The residue was purified by silica gel column chromatography (ethyl acetate/hexane) to give the title compound (3.1 g).

$^1$H NMR (300 MHz, DMSO-$d_6$) δ 1.97 (3H, s), 2.37 (3H, s), 3.88 (3H, s), 8.32 (1H, s), 10.15 (1H, s).

E) methyl 2-amino-5-bromo-6-methyl-3-nitrobenzoate

A mixture of methyl 2-acetamido-5-bromo-6-methyl-3-nitrobenzoate (3.0 g), 12 N hydrochloric acid (15 mL) and ethanol (100 mL) was refluxed overnight. The mixture was neutralized with a saturated aqueous sodium hydrogen carbonate solution at 0° C., and the precipitated solid was collected by filtration, and washed with water to give the title compound (2.4 g).

$^1$H NMR (300 MHz, DMSO-$d_6$) δ 2.28 (3H, s), 3.91 (3H, s), 7.32 (2H, s), 8.27 (1H, s).

F) methyl 2,3-diamino-6-methylbenzoate

A mixture of methyl 2-amino-5-bromo-6-methyl-3-nitrobenzoate (500 mg), triethylamine (260 mg), 10% palladium-carbon (180 mg) and methanol (10 mL) was stirred at normal pressure under a hydrogen atmosphere at room temperature for 2 hr. The catalyst was filtered off, and the filtrate was concentrated under reduced pressure. The obtained residue was partitioned with ethyl acetate-water, and the organic layer was washed with water, dried over anhydrous magnesium sulfate, and concentrated under reduced pressure to give the title compound (300 mg).

$^1$H NMR (300 MHz, CDCl$_3$) δ 2.37 (3H, s), 3.22 (2H, brs), 3.90 (3H, s), 4.96 (2H, brs), 6.47 (1H, d, J=7.7 Hz), 6.70 (1H, d, J=7.8 Hz).

G) methyl 5-methyl-1H-benzimidazole-4-carboxylate

A mixture of methyl 2,3-diamino-6-methylbenzoate (1.7 g) and formic acid (18 mL) was stirred at 80° C. overnight. The reaction mixture was concentrated, the obtained residue was partitioned with an ethyl acetate-saturated aqueous sodium hydrogen carbonate solution, and the organic layer was washed with saturated brine, dried over anhydrous magnesium sulfate and concentrated under reduced pressure. The residue was purified by silica gel column chromatography (ethyl acetate/methanol) to give the title compound (690 mg).

MS: [M+H]$^+$ 191.0.

H) (5-methyl-1H-benzimidazol-4-yl)methanol

To a mixture of lithium aluminum hydride (110 mg) and THF (3.8 mL) was added a solution of methyl 5-methyl-1H-benzimidazole-4-carboxylate (0.29 g) in THF (3.8 mL) at 0° C., and the mixture was stirred under a nitrogen atmosphere at room temperature for 3 hr. To the mixture was added ice water, insoluble material was filtered off, and the filtrate was extracted with ethyl acetate. The organic layer was washed with saturated brine, and dried over anhydrous magnesium sulfate. The residue was purified by silica gel column chromatography (ethyl acetate/hexane) to give the title compound (130 mg).

MS: [M+H]$^+$ 163.1.

I) 4-(azidomethyl)-5-methyl-1H-benzimidazole

To a mixture of (5-methyl-1H-benzimidazol-4-yl)methanol (0.15 g), DBU (0.21 g) and DMF (3 mL) was added DPPA (0.38 g) at 0° C., and the mixture was stirred at room temperature for 2 hr. To the mixture was added water, and the mixture was extracted with ethyl acetate. The organic layer was washed with water, dried over anhydrous magnesium sulfate, and concentrated under reduced pressure. The residue was purified by silica gel column chromatography (ethyl acetate/methanol) to give the title compound (30 mg).

MS: [M+H]$^+$ 188.1.

J) 1-(5-methyl-1H-benzimidazol-4-yl)methanamine

A mixture of 4-(azidomethyl)-5-methyl-1H-benzimidazole (30 mg), 10% palladium-carbon (17 mg) and methanol (1.6 mL) was stirred at normal pressure under a hydrogen atmosphere at room temperature for 2 hr. The catalyst was filtered off, and the filtrate was concentrated under reduced pressure to give the title compound (25 mg).

$^1$H NMR (300 MHz, CDCl$_3$) δ 2.37 (3H, s), 4.86 (2H, s), 6.80-7.76 (2H, m), 7.96 (1H, s).

K) N-((5-methyl-1H-benzimidazol-4-yl)methyl)-4-(trifluoromethoxy)benzamide

To a mixture of 4-(trifluoromethoxy)benzoic acid (100 mg) and DMF (5 mL) were added HOBt·H$_2$O (89 mg), WSC·HCl (110 mg) and 1-(5-methyl-1H-benzimidazol-4-yl)methanamine (78 mg) at room temperature, and the mixture was stirred overnight. To the mixture was added a saturated aqueous sodium hydrogen carbonate solution, and the mixture was extracted with ethyl acetate. The organic layer was separated, washed with water, dried over anhydrous magnesium sulfate and concentrated under reduced pressure. The residue was purified by silica gel column chromatography (ethyl acetate/hexane) to give the title compound (67 mg).

$^1$H NMR (300 MHz, DMSO-d$_6$) δ 2.42 (3H, s), 4.81 (2H, brs), 7.04 (1H, d, J=8.1 Hz), 7.37-7.50 (3H, m), 7.99 (2H, d, J=7.8 Hz), 8.18 (1H, s), 9.05 (1H, brs), 12.33 (1H, brs).

Example 4

N-((5-iodo-1H-indazol-4-yl)methyl)-4-(trifluoromethoxy)benzamide

A) methyl 3-amino-6-iodo-2-methylbenzoate

To a mixture of methyl 3-amino-2-methylbenzoate (14 g) and DMF (250 mL) was added N-iodosuccinimide (20 g) at 0° C., and the mixture was stirred at room temperature for 4 hr. The reaction mixture was concentrated, the obtained residue was partitioned with an ethyl acetate-saturated aqueous sodium hydrogen carbonate solution, and the organic layer was washed with water and saturated brine, dried over anhydrous magnesium sulfate and concentrated under reduced pressure. The residue was purified by silica gel column chromatography (ethyl acetate/hexane) to give the title compound (22 g).

MS: [M+H]$^+$ 291.9.

B) methyl 5-iodo-1-(tetrahydro-2H-pyran-2-yl)-1H-indazole-4-carboxylate

To a mixture of methyl 3-amino-6-iodo-2-methylbenzoate (22 g) and acetic acid (200 mL) was added an aqueous solution (60 mL) of sodium nitrite (7.8 g) at room temperature, and the mixture was stirred at room temperature for 7 hr. The reaction mixture was concentrated, the obtained residue was partitioned with an ethyl acetate-saturated aqueous sodium hydrogen carbonate solution, and the organic layer was washed with water and saturated brine, dried over anhydrous magnesium sulfate and concentrated under reduced pressure. To a mixture of the obtained residue and THF (50 mL) were added p-toluenesulfonic acid.monohydrate (3.6 g) and 3,4-dihydro-2H-pyran (12 g) at room temperature, and the mixture was stirred at 50° C. overnight. The mixture was neutralized with a saturated aqueous sodium hydrogen carbonate solution at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (17 g).

$^1$H NMR (300 MHz, DMSO-d$_6$) δ 1.40-2.44 (6H, m), 3.65-3.93 (2H, m), 3.98 (3H, s), 5.91 (1H, dd, J=9.7, 2.5 Hz), 7.73 (1H, dd, J=8.7, 0.8 Hz), 7.93 (1H, d, J=8.7 Hz), 8.18 (1H, s).

C) 5-iodo-1-(tetrahydro-2H-pyran-2-yl)-1H-indazole-4-carboxylic acid

To a mixture of methyl 5-iodo-1-(tetrahydro-2H-pyran-2-yl)-1H-indazole-4-carboxylate (3.8 g) and methanol (10 mL) was added 2 M aqueous sodium hydroxide solution (10 mL) at room temperature, and the mixture was stirred at room temperature overnight. The mixture was neutralized with 1 N hydrochloric acid at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (2.0 g).

$^1$H NMR (300 MHz, DMSO-d$_6$) δ 1.31-2.46 (6H, m), 3.64-3.96 (2H, m), 5.77-5.98 (1H, m), 7.68 (1H, dd, J=8.7, 0.8 Hz), 7.89 (1H, d, J=8.7 Hz), 8.14 (1H, s).

D) (5-iodo-1-(tetrahydro-2H-pyran-2-yl)-1H-indazol-4-yl)methanol

To a mixture of 5-iodo-1-(tetrahydro-2H-pyran-2-yl)-1H-indazole-4-carboxylic acid (2.6 g) and THF (20 mL) were added oxalyl chloride (1.1 g) and DMF (30 uL) at room temperature. The mixture was stirred at room temperature for 10 min and concentrated. To a mixture of the obtained residue, THF (20 mL) and DMF (3 mL) was added sodium borohydride (0.53 g) at room temperature, and the mixture was stirred at room temperature for 4 hr. To the mixture was added a saturated aqueous sodium hydrogen carbonate solution at 0° C., and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (760 mg).

$^1$H NMR (300 MHz, DMSO-d$_6$) δ 1.47-1.62 (2H, m) 1.64-1.86 (1H, m) 1.88-2.10 (2H, m) 2.37-2.47 (1H, m) 3.63-3.79 (1H, m) 3.82-3.91 (1H, m) 4.81 (2H, d, J=5.7 Hz) 5.52 (1H, t, J=5.5 Hz) 5.83 (1H, dd, J=9.7, 2.5 Hz) 7.45 (1H, d, J=8.7 Hz) 7.72 (1H, d, J=9.1 Hz) 8.33 (1H, s).

E) 2-((5-iodo-1-(tetrahydro-2H-pyran-2-yl)-1H-indazol-4-yl)methyl)-1H-isoindole-1,3(2H)-dione To a mixture of (5-iodo-1-(tetrahydro-2H-pyran-2-yl)-1H-indazol-4-yl)methanol (200 mg) and THF (4 mL) were added 1,1'-(azodicarbonyl)dipiperidine (170 mg), tributylphosphine (150 mg) and 1H-isoindole-1,3(2H)-dione (90 mg) at room temperature, and the mixture was stirred at room temperature overnight. The precipitated solid was collected by filtration to give the title compound (170 mg).

¹H NMR (300 MHz, DMSO-d₆) δ 1.45-2.40 (6H, m), 3.55-3.98 (2H, m), 5.13 (2H, s), 5.84 (1H, dd, J=9.7, 2.5 Hz), 7.51 (1H, d, J=9.1 Hz), 7.72-8.00 (6H, m).

F) N-((5-iodo-1-(tetrahydro-2H-pyran-2-yl)-1H-indazol-4-yl)methyl)-4-(trifluoromethoxy)benzamide To a mixture of 2-((5-iodo-1-(tetrahydro-2H-pyran-2-yl)-1H-indazol-4-yl)methyl)-1H-isoindole-1,3(2H)-dione (930 mg) and ethanol (6 mL) was added hydrazine monohydrate (4 mL) at room temperature, and the mixture was stirred at room temperature for 2 hr. The reaction mixture was concentrated, the obtained residue was partitioned with an ethyl acetate-saturated aqueous sodium hydrogen carbonate solution, and the organic layer was washed with saturated brine, dried over anhydrous magnesium sulfate and concentrated under reduced pressure. To a mixture of the obtained residue and DMA (8 mL) were added 4-(trifluoromethoxy)benzoyl chloride (640 mg) and triethylamine (390 mg) at room temperature, and the mixture was stirred at room temperature for 1 hr. To the mixture was added a saturated aqueous sodium hydrogen carbonate solution, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (540 mg).

¹H NMR (300 MHz, DMSO-d₆) δ 1.47-1.61 (2H, m) 1.64-1.85 (1H, m) 1.96-2.08 (2H, m) 2.17-2.44 (1H, m) 3.62-3.79 (1H, m) 3.80-3.92 (1H, m) 4.83 (2H, d, J=5.3 Hz) 5.84 (1H, dd, J=9.7, 2.5 Hz) 7.36-7.58 (3H, m) 7.79 (1H, d, J=8.7 Hz) 7.92-8.08 (2H, m) 8.24 (1H, s) 9.14 (1H, t, J=5.1 Hz).

G) N-((5-iodo-1H-indazol-4-yl)methyl)-4-(trifluoromethoxy)benzamide

To a mixture of N-((5-iodo-1-(tetrahydro-2H-pyran-2-yl)-1H-indazol-4-yl)methyl)-4-(trifluoromethoxy)benzamide (50 mg), ethanol (1 mL) and THF (1 mL) was added 6 N hydrochloric acid (1 mL) at room temperature, and the mixture was stirred at 60° C. for 5 hr. The reaction mixture was concentrated to give the title compound (30 mg).

¹H NMR (300 MHz, DMSO-d₆) δ 4.84 (2H, d, J=5.3 Hz) 7.29 (1H, d, J=8.7 Hz) 7.46 (2H, d, J=7.9 Hz) 7.71 (1H, d, J=8.7 Hz) 7.90-8.03 (2H, m) 8.18 (1H, d, J=1.1 Hz) 9.14 (1H, t, J=5.3 Hz) 13.23 (1H, br. s.).

Example 5

4-(trifluoromethoxy)-N-((5-(trifluoromethyl)-1H-indazol-4-yl)methyl)benzamide

To a mixture of N-((5-iodo-1-(tetrahydro-2H-pyran-2-yl)-1H-indazol-4-yl)methyl)-4-(trifluoromethoxy)benzamide (150 mg) and DMF (2 mL) was added (trifluoromethyl)copper-1,10-phenanthrolin (170 mg) at room temperature, and the mixture was stirred under a nitrogen atmosphere at 90° C. overnight. The mixture was neutralized with a saturated aqueous sodium hydrogen carbonate solution at 0° C., and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give N-((1-(tetrahydro-2H-pyran-2-yl)-5-(trifluoromethyl)-1H-indazol-4-yl)methyl)-4-(trifluoromethoxy)benzamide (19 mg). To a mixture of the obtained N-((1-(tetrahydro-2H-pyran-2-yl)-5-(trifluoromethyl)-1H-indazol-4-yl)methyl)-4-(trifluoromethoxy)benzamide (19 mg), THF (1 mL) and ethanol (1 mL) was added 6 N hydrochloric acid (7 ul) at room temperature, and the mixture was stirred at 60° C. for 2 hr. The mixture was neutralized with a saturated aqueous sodium hydrogen carbonate solution at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (3.0 mg).

¹H NMR (300 MHz, DMSO-d₆) δ 4.96 (2H, d, J=5.3 Hz) 7.46 (2H, d, J=8.0 Hz) 7.65 (2H, s) 7.98 (2H, d, J=8.7 Hz) 8.35 (1H, s) 9.17 (1H, t, J=4.9 Hz) 13.47 (1H, brs).

Example 6

N-((5-methoxy-1H-indazol-4-yl)methyl)-4-(trifluoromethoxy)benzamide

A) N-((5-methoxy-1-(tetrahydro-2H-pyran-2-yl)-1H-indazol-4-yl)methyl)-4-(trifluoromethoxy)benzamide To a mixture of N-((5-iodo-1-(tetrahydro-2H-pyran-2-yl)-1H-indazol-4-yl)methyl)-4-(trifluoromethoxy)benzamide (200 mg) and methanol (0.5 mL) were added copper iodide (7.0 mg), 1,10-phenanthrolin (13 mg) and cesium carbonate (180 mg) at room temperature, and the mixture was stirred at 110° C. overnight. The mixture was neutralized with a saturated aqueous sodium hydrogen carbonate solution at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (110 mg).

¹H NMR (300 MHz, DMSO-d₆) δ 1.47-1.60 (2H, m) 1.65-1.81 (1H, m) 1.89-2.15 (2H, m) 2.23-2.48 (1H, m) 3.62-3.77 (1H, m) 3.82-3.94 (4H, m) 4.77 (2H, d, J=5.7 Hz) 5.70-5.82 (1H, m) 7.29 (1H, d, J=9.1 Hz) 7.44 (2H, d, J=8.0 Hz) 7.62 (1H, d, J=9.1 Hz) 7.93-8.03 (2H, m) 8.09 (1H, s) 9.01 (1H, t, J=5.5 Hz).

B) N-((5-methoxy-1H-indazol-4-yl)methyl)-4-25 (trifluoromethoxy)benzamide

To a mixture of N-((5-methoxy-1-(tetrahydro-2H-pyran-2-yl)-1H-indazol-4-yl)methyl)-4-(trifluoromethoxy)benzamide (110 mg), THF (1 mL) and ethanol (1 mL) was added 6 N hydrochloric acid (500 ul) at room temperature, and the mixture was stirred at 60° C. for 2 hr. The mixture was neutralized with a saturated aqueous sodium hydrogen carbonate solution at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (46 mg).

¹H NMR (300 MHz, DMSO-d₆) δ 3.86 (3H, s) 4.78 (2H, d, J=5.3 Hz) 7.23 (1H, d, J=8.7 Hz) 7.44 (3H, d, J=9.1 Hz) 7.94-8.02 (2H, m) 8.03-8.06 (1H, m) 8.99 (1H, t, J=5.3 Hz) 12.91 (1H, s).

Example 7

N-(1H-indazol-4-ylmethyl)-4-(trifluoromethoxy)benzamide

A) N-((1-(tetrahydro-2H-pyran-2-yl)-1H-indazol-4-yl)methyl)-4-(trifluoromethoxy)benzamide A mixture of N-((5-iodo-1-(tetrahydro-2H-pyran-2-yl)-1H-indazol-4-yl)methyl)-4-(trifluoromethoxy)benzamide (64 mg), 10% palladium-carbon (12 mg) and ethanol (3 mL) was stirred under a hydrogen gas atmosphere at room temperature for 4 hr. Insoluble material was filtered off through celite, and the filtrate was concentrated under reduced pressure. The residue was purified by silica gel column chromatography (ethyl acetate/hexane) to give the title compound (23 mg).

$^1$H NMR (300 MHz, DMSO-d$_6$) δ 1.58 (2H, d, J=4.2 Hz) 1.77 (1H, d, J=7.6 Hz) 1.89-2.25 (2H, m) 2.43 (1H, brs) 3.64-3.81 (1H, m) 3.83-3.97 (1H, m) 4.79 (2H, d, J=5.7 Hz) 5.84 (1H, dd, J=9.7, 2.5 Hz) 7.10 (1H, d, J=6.4 Hz) 7.36 (1H, dd, J=8.5, 7.0 Hz) 7.44-7.54 (2H, m) 7.58-7.80 (1H, m) 7.93-8.10 (2H, m) 8.24 (1H, s) 9.25 (1H, t, J=5.9 Hz).

B) N-(1H-indazol-4-ylmethyl)-4-(trifluoromethoxy)benzamide

To a mixture of N-((1-(tetrahydro-2H-pyran-2-yl)-1H-indazol-4-yl)methyl)-4-(trifluoromethoxy)benzamide (23 mg), THF (0.5 mL) and ethanol (0.5 mL) was added 6 N hydrochloric acid (250 ul) at room temperature, and the mixture was stirred at 60° C. for 2 hr. The mixture was neutralized with a saturated aqueous sodium hydrogen carbonate solution at 0° C. and extracted with ethyl acetate. The organic layer was separated, washed with water and saturated brine, dried over anhydrous magnesium sulfate, and concentrated under reduced pressure to give the title compound (10 mg).

$^1$H NMR (300 MHz, DMSO-d$_6$) δ 4.80 (2H, d, J=5.7 Hz) 7.03 (1H, d, J=6.8 Hz) 7.29 (1H, dd, J=8.3, 6.8 Hz) 7.40-7.55 (3H, m) 7.91-8.09 (2H, m) 8.19 (1H, s) 9.23 (1H, t, J=5.9 Hz) 13.09 (1H, brs).

Example 8

3,5-difluoro-4-methoxy-N-((6-methoxy-1-methyl-1H-benzimidazol-7-yl)methyl)benzamide

A) methyl 6-fluoro-2-(methylamino)-3-nitrobenzoate

A mixture of methyl 2,6-difluoro-3-nitrobenzoate (21 g), potassium carbonate (20 g), 2 M methylamine THF solution (53 mL) and THF (200 ml) was stirred at room temperature overnight. To the mixture was added water, and the mixture was extracted with ethyl acetate. The organic layer was separated, washed with water and saturated brine, dried over anhydrous magnesium sulfate and concentrated under reduced pressure. The residue was crystallized from diisopropyl ether to give the title compound (22 g).

$^1$H NMR (300 MHz, DMSO-d$_6$) δ 2.83-2.88 (3H, m), 3.90 (3H, s), 6.65 (1H, dd, J=9.5, 8.7 Hz), 8.27 (1H, dd, J=9.5, 6.4 Hz), 8.46 (1H, d, J=3.4 Hz).

B) methyl 6-methoxy-2-(methylamino)-3-nitrobenzoate

A mixture of methyl 6-fluoro-2-(methylamino)-3-nitrobenzoate (22 g), 28% sodium methoxide methanol solution (22 g) and methanol (200 mL) was stirred at room temperature for 3 hr. To the mixture was added water, and the precipitated solid was collected by filtration to give the title compound (21 g).

$^1$H NMR (300 MHz, DMSO-d$_6$) δ 2.86 (3H, d, J=5.3 Hz), 3.81 (3H, s), 3.86 (3H, s), 6.56 (1H, d, J=9.8 Hz), 8.22 (1H, d, J=9.5 Hz), 8.37 (1H, d, J=4.9 Hz).

C) methyl 6-methoxy-1-methyl-1H-benzimidazole-7-carboxylate

A mixture of methyl 6-methoxy-2-(methylamino)-3-nitrobenzoate (20 g), zinc (27 g) and formic acid (400 mL) was stirred at 100° C. overnight. Insoluble material was filtered off and the filtrate was concentrated. The obtained residue was partitioned with an ethyl acetate-saturated aqueous sodium hydrogen carbonate solution, and the organic layer was washed with water and saturated brine, dried over anhydrous magnesium sulfate and concentrated under reduced pressure. The residue was purified by silica gel column chromatography (ethyl acetate/methanol) to give the title compound (7.0 g).

$^1$H NMR (300 MHz, DMSO-d$_6$) δ 3.65 (3H, s), 3.83 (3H, s), 3.90 (3H, s), 7.06 (1H, d, J=8.7 Hz), 7.72 (1H, d, J=9.1 Hz), 8.11 (1H, s).

D) 7-(azidomethyl)-6-methoxy-1-methyl-1H-benzimidazole

To a suspension of lithium aluminum hydride (1.8 g) in THF (50 mL) was added dropwise a solution of methyl 6-methoxy-1-methyl-1H-benzimidazole-7-carboxylate (7.0 g) in THE (50 mL) at 0° C. The mixture was stirred at 0° C. for 1 hr, and sodium sulfate.10 hydrate was added to the reaction mixture. Insoluble material was filtered off through celite, and the filtrate was concentrated under reduced pressure. To a mixture of the obtained residue and DMF (100 mL) was added DPPA (13 g) at room temperature, and the mixture was stirred at room temperature overnight. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (3.0 g).

$^1$H NMR (300 MHz, DMSO-d$_6$) δ 3.87 (3H, s), 3.96 (3H, s), 4.80 (2H, s), 7.07 (1H, d, J=9.1 Hz), 7.64 (1H, d, J=8.7 Hz), 8.05 (1H, s).

E) 1-(6-methoxy-1-methyl-1H-benzimidazol-7-yl)methanamine dihydrochloride

A mixture of 7-(azidomethyl)-6-methoxy-1-methyl-1H-benzimidazole (2.8 g), triphenylphosphine (4.0 g), THE (25 mL) and water (6 mL) was stirred at room temperature for 7 hr. The reaction mixture was concentrated, and the obtained residue was dissolved in ethyl acetate, and a 4.0 M hydrogen chloride ethyl acetate solution (9.5 mL) was added. The precipitated solid was collected by filtration and washed with ethyl acetate to give the title compound (2.8 g).

$^1$H NMR (300 MHz, DMSO-d$_6$) δ 3.95 (3H, s), 4.25 (3H, s), 4.38 (2H, d, J=5.7 Hz), 7.36 (1H, d, J=9.1 Hz), 7.50-7.68 (1H, m), 7.85 (1H, d, J=9.1 Hz), 8.38 (3H, brs), 9.12 (1H, brs).

F) 3,5-difluoro-4-methoxy-N-((6-methoxy-1-methyl-1H-benzimidazol-7-yl)methyl)benzamide To a mixture of 1-(6-methoxy-1-methyl-1H-benzimidazol-7-yl)methanamine dihydrochloride (2.0 g) and DMF (25 mL) were added HOBt (1.3 g), WSC·HCl (2.2 g), 3,5-difluoro-4-methoxybenzoic acid (1.6 g) and triethylamine (3.8 g) at room temperature, and the mixture was stirred overnight. To the mixture was added water, and the precipitated solid was collected by filtration and recrystallized from ethyl acetate/ethanol to give the title compound (2.3 g).

$^1$H NMR (300 MHz, DMSO-$d_6$) δ 3.84 (3H, s), 3.94-4.01 (6H, m), 4.81 (2H, d, J=4.2 Hz), 7.02 (1H, d, J=9.1 Hz), 7.58 (1H, d, J=8.7 Hz), 7.64-7.77 (2H, m), 8.02 (1H, s), 8.69 (1H, t, J=4.0 Hz).

Example 16

N-((5-ethyl-1H-indazol-4-yl)methyl)-3,5-difluoro-4-methoxybenzamide

A) methyl 1-(tetrahydro-2H-pyran-2-yl)-5-vinyl-1H-indazole-4-carboxylate

A mixture of methyl 5-iodo-1-(tetrahydro-2H-pyran-2-yl)-1H-indazole-4-carboxylate (7.5 g), 4,4,5,5-tetramethyl-2-vinyl-1,3,2-dioxaborolane (6.0 g), 4-(di-tert-butylphosphino)-N,N-dimethylaniline-dichloropalladium (1.3 g), potassium carbonate (6.7 g), 1,2-dimethoxyethane (36 mL) and water (3.6 mL) was microwaved at 110° C. for 1 hr. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (2.4 g).

$^1$H NMR (300 MHz, DMSO-$d_6$) δ 1.47-2.46 (6H, m), 3.70-3.92 (2H, m), 3.95-3.96 (3H, m), 5.34-5.44 (1H, m), 5.72-6.06 (2H, m), 7.32-7.49 (1H, m), 7.73-7.85 (1H, m), 7.92-8.03 (1H, m), 8.18-8.28 (1H, m).

B) (1-(tetrahydro-2H-pyran-2-yl)-5-vinyl-1H-indazol-4-yl)methanol

To a mixture of lithium aluminum hydride (0.38 g) and THF (30 mL) was added a solution of methyl 1-(tetrahydro-2H-pyran-2-yl)-5-vinyl-1H-indazole-4-carboxylate (2.4 g) in THF (dry) (10 mL) at 0° C., and the mixture was stirred for 4 hr. Sodium sulfate.10 hydrate was added to the reaction mixture. The precipitated insoluble material was filtered off through celite, and the filtrate was concentrated under reduced pressure. The residue was purified by silica gel column chromatography (ethyl acetate/hexane) to give the title compound (540 mg).

$^1$H NMR (300 MHz, DMSO-$d_6$) δ 1.49-2.14 (6H, m), 3.65-3.80 (1H, m), 3.82-3.99 (1H, m), 4.86 (2H, d, J=5.7 Hz), 5.20-5.34 (2H, m), 5.63-5.93 (2H, m), 7.18 (1H, dd, J=17.6, 11.2 Hz), 7.53-7.70 (2H, m), 8.26 (1H, s).

C) 4-(azidomethyl)-1-(tetrahydro-2H-pyran-2-yl)-5-vinyl-1H-indazole

To a mixture of (1-(tetrahydro-2H-pyran-2-yl)-5-vinyl-1H-indazol-4-yl)methanol (540 mg), DBU (480 mg) and toluene (10 mL) was added DPPA (860 mg) at room temperature, and the mixture was stirred overnight. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (570 mg).

$^1$H NMR (300 MHz, DMSO-$d_6$) δ 1.47-1.86 (3H, m), 1.91-2.11 (2H, m), 2.29-2.46 (1H, m), 3.67-3.82 (1H, m), 3.83-3.96 (1H, m), 4.89 (2H, s), 5.28-5.44 (1H, m), 5.75-5.93 (2H, m), 7.08-7.24 (1H, m), 7.74 (2H, s), 8.37 (1H, s).

D) N-((5-ethyl-1H-indazol-4-yl)methyl)-3,5-difluoro-4-methoxybenzamide

A mixture of 4-(azidomethyl)-1-(tetrahydro-2H-pyran-2-yl)-5-vinyl-1H-indazole (570 mg), 10% palladium-carbon (210 mg) and ethanol (15 mL) was stirred under a hydrogen gas atmosphere at room temperature for 4 hr. The reaction mixture was filtered, and the filtrate was concentrated under reduced pressure. The residue was purified by silica gel column chromatography (NH, ethyl acetate/hexane). To a mixture of the obtained residue and DMA (5.00 ml) were added HOBt·$H_2O$ (370 mg), WSC·HCl (540 mg), 3,5-difluoro-4-methoxybenzoic acid (450 mg) and triethylamine (610 mg) at room temperature, and the mixture was stirred overnight. To the mixture was added a saturated aqueous sodium hydrogen carbonate solution at 0° C., and the mixture was extracted with ethyl acetate. The organic layer was separated, washed with water and saturated brine, dried over anhydrous magnesium sulfate and concentrated under reduced pressure. To a mixture of the obtained residue and methanol (3.0 ml) was added 6 N hydrochloric acid (3 mL) at room temperature, and the mixture was stirred at room temperature overnight. To the mixture was added water, and the precipitated solid was collected by filtration and purified by silica gel column chromatography (ethyl acetate/hexane) to give the title compound (150 mg).

$^1$H NMR (300 MHz, DMSO-$d_6$) δ 1.17 (3H, t, J=7.4 Hz), 2.81 (2H, q, J=7.6 Hz), 3.98 (3H, t, J=1.1 Hz), 4.78 (2H, d, J=5.3 Hz), 7.21 (1H, d, J=8.7 Hz), 7.36-7.43 (1H, m), 7.59-7.76 (2H, m), 8.15 (1H, d, J=0.8 Hz), 8.83-9.09 (1H, m).

Example 17

N-((5-cyclopropyl-1H-indazol-4-yl)methyl)-3,5-difluoro-4-methoxybenzamide

To a mixture of 2-((5-iodo-1-(tetrahydro-2H-pyran-2-yl)-1H-indazol-4-yl)methyl)-1H-isoindole-1,3(2H)-dione (65 mg) and ethanol (1 mL) was added hydrazine monohydrate (6.7 mg) at room temperature, and the mixture was stirred at 80° C. for 2 hr. The reaction mixture was concentrated, the obtained residue was partitioned with an ethyl acetate-saturated aqueous sodium hydrogen carbonate solution, and the organic layer was washed with water and saturated brine, dried over anhydrous magnesium sulfate and concentrated under reduced pressure. To a mixture of the obtained residue and DMF (2 mL) were added triethylamine (27 mg), WSC·HCl (26 mg), HOBt·$H_2O$ (20 mg) and 3,5-difluoro-4-methoxybenzoic acid (25 mg) at room temperature, and the mixture was stirred for 3 hr. To the mixture was added a saturated aqueous sodium hydrogen carbonate solution at 0° C., and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give 3,5-difluoro-N-((5-iodo-1-(tetrahydro-2H-pyran-2-yl)-1H-indazol-4-yl)methyl)-4-methoxybenzamide (30 mg). A mixture of the obtained 3,5-difluoro-N-((5-iodo-1-(tetrahydro-2H-pyran-2-yl)-1H-indazol-4-yl)methyl)-4-methoxybenzamide (30 mg), [1,1'-bis(diphenylphosphino)ferrocene]dichloropalladium(II) (2.1 mg), cyclopropylboronic acid (9.8 mg), tripotassium phosphate.7 hydrate (24 mg), toluene (2 mL) and water (0.5 mL) was microwaved at 100° C. for 1 hr. To the mixture was added water, and the mixture was extracted with ethyl acetate. The organic layer was separated, washed with water and saturated brine, dried over anhydrous magnesium sulfate and concentrated under reduced pressure. To a mixture of the obtained residue, methanol (1 mL) and THF (1.0 mL) was added 2 N hydrochloric acid (1 mL) at room temperature, and the mixture was stirred at room temperature overnight. The mixture was neutralized with a saturated aqueous sodium hydrogen carbonate solution at 0° C. and extracted with ethyl acetate. The organic layer was separated, washed with water and saturated brine, dried over anhydrous magnesium sulfate and concentrated under reduced pressure. The residue was separated by HPLC (C18, mobile phase: water/acetonitrile (containing 0.1% TFA)) and the obtained 20 fraction was concentrated under reduced pressure to give the title compound (3.00 mg).

$^1$H NMR (300 MHz, CDCl$_3$) δ 0.65-0.80 (2H, m), 0.97-1.13 (2H, m), 2.01-2.22 (1H, m), 4.04 (3H, t, J=1.5 Hz), 5.14 (2H, d, J=4.9 Hz), 6.18 (1H, brs), 7.14 (1H, d, J=8.7 Hz), 7.27-7.42 (3H, m), 8.14 (1H, s), 10.15 (1H, brs).

Example 20

N-((6-cyclopropyl-1-methyl-1H-benzimidazol-7-yl)methyl)-5-fluoro-6-methoxynicotinamide A) methyl 6-cyclopropyl-1-methyl-1H-benzimidazole-7-carboxylate A mixture of methyl 6-chloro-1-methyl-1H-benzimidazole-7-carboxylate (600 mg), dicyclohexyl(2',6'-dimethoxybiphenyl-2-yl)phosphine (180 mg), cyclopropylboronic acid (340 mg), tris(dibenzylideneacetone)dipalladium (0) (98 mg), 2 M aqueous sodium carbonate solution (2.7 mL) and toluene (10 mL) was microwaved at 100° C. for 5 hr. Insoluble material was filtered off, and the filtrate was concentrated. The obtained residue was partitioned with ethyl acetate-water, and the organic layer was washed with water and saturated brine, dried over anhydrous magnesium sulfate and concentrated under reduced pressure. The residue was purified by silica gel column chromatography (ethyl acetate/methanol) to give the title compound (380 mg).

$^1$H NMR (300 MHz, DMSO-d$_6$) δ 0.19 (1H, dq, J=5.6, 2.8 Hz), 0.65-0.75 (2H, m), 0.89-1.01 (2H, m), 3.72 (3H, s), 3.98 (3H, s), 6.92 (1H, d, J=8.7 Hz), 7.69 (1H, d, J=8.3 Hz), 8.27 (1H, s).

B) (6-cyclopropyl-1-methyl-1H-benzimidazol-7-yl)methanol

To a suspension of lithium aluminum hydride (110 mg) in THF (10 mL) was added dropwise at 0° C. a solution of methyl 6-cyclopropyl-1-methyl-1H-benzimidazole-7-carboxylate (450 mg) in THF (10 mL) at 0° C. The mixture was stirred at room temperature for 1 hr, and sodium sulfate.10 hydrate was added to the reaction mixture. The precipitated insoluble material was filtered off through celite, and the filtrate was concentrated under reduced pressure. The residue was purified by silica gel column chromatography (ethyl acetate/hexane) to give the title compound (150 mg).

MS: [M+H]$^+$ 203.0.

C) 7-(azidomethyl)-6-cyclopropyl-1-methyl-1H-benzimidazole

To a mixture of (6-cyclopropyl-1-methyl-1H-benzimidazol-7-yl)methanol (150 mg), DBU (170 mg) and DMF (3 mL) was added DPPA (300 mg) at 0° C., and the mixture was stirred at room temperature for 15 hr. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (120 mg).

$^1$H NMR (300 MHz, DMSO-d$_6$) δ 0.66-0.73 (2H, m), 0.98-1.07 (2H, m), 2.19 (1H, tt, J=8.4, 5.4 Hz), 4.04 (3H, s), 5.09 (2H, s), 6.96 (1H, d, J=8.3 Hz), 7.55 (1H, d, J=8.3 Hz), 8.10 (1H, s).

D) 1-(6-cyclopropyl-1-methyl-1H-benzimidazol-7-yl)methanamine dihydrochloride

A mixture of 7-(azidomethyl)-6-cyclopropyl-1-methyl-1H-benzimidazole (110 mg), triphenylphosphine (150 mg), THF (5 mL) and water (1.000 mL) was stirred at room temperature for 7 hr. The reaction mixture was concentrated, and the obtained residue was dissolved in ethyl acetate, and 4.0 M hydrogen chloride ethyl acetate solution (0.36 mL) was added. The precipitated solid was collected by filtration and washed with ethyl acetate to give the title compound (130 mg).

$^1$H NMR (300 MHz, DMSO-d$_6$) δ 0.71-0.81 (2H, m), 1.05-1.14 (2H, m), 2.37-2.47 (1H, m), 4.34 (3H, s), 4.70 (2H, d, J=5.3 Hz), 7.32 (1H, d, J=8.7 Hz), 7.79 (1H, d, J=8.3 Hz), 8.84 (3H, brs), 9.44 (1H, s).

E) N-((6-cyclopropyl-1-methyl-1H-benzimidazol-7-yl)methyl)-5-fluoro-6-methoxynicotinamide A mixture of 5-fluoro-6-methoxynicotinic acid (45 mg), triethylamine (110 mg), WSC·HCl (63 mg), HOBt (36 mg), 1-(6-cyclopropyl-1-methyl-1H-benzimidazol-7-yl)methanamine dihydrochloride (60 mg) and DMF (5 mL) was stirred at room temperature overnight. To the mixture was added water, and the precipitated solid was collected by filtration to give the title compound (50 mg).

$^1$H NMR (300 MHz, DMSO-d$_6$) δ 0.63-0.71 (2H, m), 0.88-0.96 (2H, m), 2.11 (1H, tt, J=8.4, 5.4 Hz), 3.98 (3H, s), 4.02 (3H, s), 5.06 (2H, d, J=4.2 Hz), 6.94 (1H, d, J=8.3 Hz), 7.51 (1H, d, J=8.3 Hz), 8.07-8.17 (2H, m), 8.52 (1H, d, J=1.9 Hz), 8.79 (1H, t, J=4.0 Hz).

Example 117

N-((6-methoxy-1-methyl-1H-benzimidazol-7-yl)methyl)-4-(trifluoromethyl)benzamide To a mixture of 1-(6-methoxy-1-methyl-1H-benzimidazol-7-yl)methanamine dihydrochloride (150 mg) and DMF (3 mL) were added HOBt (92 mg), WSC·HCl (163 mg), 4-(trifluoromethyl)benzoic acid (130 mg) and triethylamine (290 mg) at room temperature, and the mixture was stirred overnight. To the mixture was added water, and the precipitated solid was collected by filtration to give the title compound (150 mg).

¹H NMR (300 MHz, DMSO-d₆) δ 3.85 (3H, s), 4.00 (3H, s), 4.85 (2H, d, J=4.2 Hz), 7.02 (1H, d, J=8.7 Hz), 7.58 (1H, d, J=8.7 Hz), 7.80 (2H, d, J=8.3 Hz), 7.99-8.11 (3H, m), 8.88 (1H, t, J=4.2 Hz).

Example 134

6-(difluoromethoxy)-N-((1,6-dimethyl-1H-benzimidazol-7-yl)methyl)-5-fluoronicotinamide A) methyl 5-fluoro-6-oxo-1,6-dihydropyridine-3-carboxylate To a solution of 5-fluoro-6-oxo-1,6-dihydropyridine-3-carboxylic acid (3.2 g) in methanol (50 mL) was added dropwise thionyl chloride (3.0 mL) at 0° C., and the mixture was stirred at 60° C. overnight. The solvent was evaporated under reduced pressure, and the precipitated solid was collected by filtration and washed with water to give the title compound (2.7 g).

¹H NMR (300 MHz, DMSO-d₆) δ 3.78 (3H, s), 7.67 (1H, dd, J=11.1, 2.3 Hz), 7.93 (1H, d, J=2.2 Hz), 12.53-12.81 (1H, m).

B) methyl 6-(difluoromethoxy)-5-fluoronicotinate

To a solution of methyl 5-fluoro-6-oxo-1,6-dihydropyridine-3-carboxylate (5.0 g) in acetonitrile (450 mL) was added sodium hydride (60%, 3.2 g) in several portions at room temperature. After stirring at room temperature for 30 min, 2-(fluorosulfonyl)difluoroacetic acid (5.1 mL) was added dropwise, and the mixture was stirred at room temperature overnight. To the reaction mixture was added water, and the solvent was evaporated under reduced pressure. The residue was diluted with water and extracted with ethyl acetate. The extract was washed with water, dried over anhydrous sodium sulfate, and concentrated under reduced pressure. The residue was purified by silica gel column chromatography (hexane/ethyl acetate) to give the title compound (4.8 g).

¹H NMR (300 MHz, DMSO-d₆) δ 3.89 (3H, s), 7.56-8.07 (1H, m), 8.34 (1H, dd, J=10.1, 2.0 Hz), 8.63 (1H, d, J=1.9 Hz).

C) 6-(difluoromethoxy)-5-fluoronicotinic acid

To a mixture of methyl 6-(difluoromethoxy)-5-fluoronicotinate (4.8 g) and ethanol (110 mL) was added 1 M aqueous sodium hydroxide solution (43 mL), and the mixture was stirred at room temperature for 30 min. To the mixture was added 1N hydrochloric acid (45 mL), and the precipitated solid was collected by filtration and washed with water to give the title compound (3.6 g).

¹H NMR (300 MHz, DMSO-d₆) δ 7.55-8.06 (1H, m), 8.27 (1H, dd, J=10.0, 1.9 Hz), 8.59 (1H, d, J=1.7 Hz), 13.68 (1H, br s).

D) methyl 6-chloro-2-(methylamino)-3-nitrobenzoate

To a mixture of methyl 2,6-dichloro-3-nitrobenzoate (30 g) and THF (500 mL) were added potassium carbonate (25 g) and 2 M methylamine THF solution (63 mL) at 0° C., and the mixture was stirred at room temperature overnight. The reaction mixture was concentrated, and the obtained residue was partitioned with ethyl acetate-water. The organic layer was washed with saturated brine, dried over anhydrous magnesium sulfate and concentrated under reduced pressure. The obtained solid was crystallized from hexane to give the title compound (29 g).

¹H NMR (300 MHz, DMSO-d₆) δ 2.87 (3H, d, J=5.3 Hz), 3.91 (3H, s), 6.84 (1H, d, J=9.1 Hz), 8.15 (1H, d, J=9.1 Hz), 8.25-8.40 (1H, m).

E) methyl 6-chloro-1-methyl-1H-benzimidazole-7-carboxylate

A mixture of methyl 6-chloro-2-(methylamino)-3-nitrobenzoate (4.0 g), iron (9.1 g) and formic acid (80 mL) was stirred at 100° C. for 2 days. Insoluble material was filtered off, and the filtrate was concentrated. The obtained residue was partitioned with an ethyl acetate-saturated aqueous sodium hydrogen carbonate solution, and the organic layer was washed with water and saturated brine, dried over anhydrous magnesium sulfate and concentrated under reduced pressure. The residue was purified by silica gel column chromatography (ethyl acetate/methanol) to give the title compound (2.1 g).

¹H NMR (300 MHz, DMSO-d₆) δ 3.72 (3H, s), 4.00 (3H, s), 7.35 (1H, d, J=8.7 Hz), 7.79 (1H, d, J=8.7 Hz), 8.32 (1H, s).

F) methyl 1,6-dimethyl-1H-benzimidazole-7-carboxylate

A mixture of methyl 6-chloro-1-methyl-1H-benzimidazole-7-carboxylate (3.8 g), dicyclohexyl(2',6'-diisopropoxybiphenyl-2-yl)phosphine palladium(II) phenethylamine chloride (1:1 MTBE solvate) (1.4 g), dicyclohexyl (2',6'-diisopropoxybiphenyl-2-yl)phosphine (1.6 g), cesium carbonate (17 g), trimethylboroxine (13 g), water (17 mL) and toluene (68 mL) was stirred under a nitrogen atmosphere at 105° C. overnight. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (3.5 g).

¹H NMR (300 MHz, DMSO-d₆) δ 2.39 (3H, s), 3.69 (3H, s), 3.95 (3H, s), 7.12 (1H, d, J=8.3 Hz), 7.66 (1H, d, J=8.3 Hz), 8.17 (1H, s).

G) (1,6-dimethyl-1H-benzimidazol-7-yl)methanol

To a suspension of lithium aluminum hydride (160 mg) in THF (14 mL) was added dropwise a solution of methyl 1,6-dimethyl-1H-benzimidazole-7-carboxylate (0.58 g) in TH (14 mL) at 0° C. After stirring at room temperature for 1 hr, sodium sulfate.10 hydrate was added to the reaction mixture. The precipitated insoluble material was filtered off through celite, and the filtrate was concentrated under reduced pressure. The obtained solid was crystallized from ethyl acetate/hexane to give the title compound (270 mg).

¹H NMR (300 MHz, DMSO-d₆) δ 2.46 (3H, s), 4.06 (3H, s), 4.82 (2H, d, J=5.3 Hz), 5.13 (1H, t, J=5.3 Hz), 7.01 (1H, d, J=8.3 Hz), 7.43 (1H, d, J=8.3 Hz), 8.02 (1H, s).

H) 7-(azidomethyl)-1,6-dimethyl-1H-benzimidazole

To a mixture of (1,6-dimethyl-1H-benzimidazol-7-yl) methanol (0.27 g), DBU (0.35 g) and DMF (8.5 mL) was added DPPA (0.63 g) at 0° C., and the mixture was stirred at room temperature for 60 hr. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (280 mg).

$^1$H NMR (300 MHz, DMSO-$d_6$) δ 2.49 (3H, s), 4.02 (3H, s), 4.89 (2H, s), 7.11 (1H, d, J=8.0 Hz), 7.54 (1H, d, J=8.3 Hz), 8.08 (1H, s).

I) 1-(1,6-dimethyl-1H-benzimidazol-7-yl)methanamine dihydrochloride

A mixture of 7-(azidomethyl)-1,6-dimethyl-1H-benzimidazole (0.28 g), triphenylphosphine (0.44 g), THF (5.8 mL) and water (1.2 mL) was stirred at room temperature overnight. The reaction mixture was concentrated, the obtained residue was dissolved in ethyl acetate, and 4.0 M hydrogen chloride ethyl acetate solution (1.0 mL) was added. The precipitated solid was collected by filtration and washed with ethyl acetate to give the title compound (320 mg).

$^1$H NMR (300 MHz, DMSO-$d_6$) δ 2.61 (3H, s), 4.32 (3H, s), 4.41-4.61 (2H, m), 7.48 (1H, d, J=8.7 Hz), 7.79 (1H, d, J=8.4 Hz), 8.74 (3H, brs), 9.40 (1H, s).

J) 6-(difluoromethoxy)-N-((1,6-dimethyl-1H-benzimidazol-7-yl)methyl)-5-fluoronicotinamide To a mixture of 1-(1,6-dimethyl-1H-benzimidazol-7-yl) methanamine dihydrochloride (60 mg) and DMF (2.0 mL) were added HOBt·H$_2$O (44 mg), WSC·HCl (65 mg), 6-(difluoromethoxy)-5-fluoronicotinic acid (60 mg) and triethylamine (120 mg) at room temperature, and the mixture was stirred overnight. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (38 mg).

$^1$H NMR (300 MHz, DMSO-$d_6$) δ 2.42 (3H, s), 4.02 (3H, s), 4.87 (2H, d, J=4.5 Hz), 7.08 (1H, d, J=8.3 Hz), 7.51 (1H, d, J=8.3 Hz), 7.77 (1H, t, J=71.7 Hz), 8.07 (1H, s), 8.34 (1H, dd, J=11.0, 1.9 Hz), 8.56 (1H, d, J=1.9 Hz), 8.90 (1H, brs).

Example 139

N-((6-methoxy-1-methyl-1H-benzimidazol-7-yl)methyl)-5-(trifluoromethyl)thiophene-3-carboxamide To a mixture of 1-(6-methoxy-1-methyl-1H-benzimidazol-7-yl)methanamine dihydrochloride (30 mg) and DMF (2 mL) were added HOBt (18 mg), WSC·HCl (33 mg), 5-(trifluoromethyl)thiophene-3-carboxylic acid (27 mg) and triethylamine (58 mg) at room temperature, and the mixture was stirred overnight. To the mixture was added water, and the precipitated solid was collected by filtration and purified by silica gel column chromatography (NH, ethyl acetate/hexane) to give the title compound (7.4 mg).

$^1$H NMR (300 MHz, DMSO-$d_6$) δ 3.84 (3H, s), 3.97 (3H, s), 4.80 (2H, d, J=4.2 Hz), 7.02 (1H, d, J=8.7 Hz), 7.58 (1H, d, J=8.7 Hz), 8.02 (1H, s), 8.14 (1H, t, J=1.3 Hz), 8.52 (1H, d, J=1.5 Hz), 8.65 (1H, t, J=4.0 Hz).

Example 143

6-(difluoromethoxy)-N-((6-ethyl-1-methyl-1H-benzimidazol-7-yl)methyl)-5-fluoronicotinamide

A) methyl 1-methyl-6-vinyl-1H-benzimidazole-7-carboxylate

A mixture of methyl 6-chloro-1-methyl-1H-benzimidazole-7-carboxylate (3.9 g), 2 M aqueous sodium carbonate solution (2.9 mL), 4,4,5,5-tetramethyl-2-vinyl-1,3,2-dioxaborolane (6.7 g), tris(dibenzylideneacetone)dipalladium(0) (1.6 g), dicyclohexyl(2',6'-dimethoxybiphenyl-2-yl)phosphine (2.1 g) and toluene (72 mL) was microwaved at 110° C. for 3 hr. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (3.7 g).

$^1$H NMR (300 MHz, DMSO-$d_6$) δ 3.71 (3H, s), 3.97 (3H, s), 5.30-5.42 (1H, m), 5.72-5.95 (1H, m), 6.81 (1H, dd, J=17.4, 11.0 Hz), 7.59 (1H, d, J=8.3 Hz), 7.75 (1H, d, J=8.0 Hz), 8.24 (1H, s).

B) 7-(azidomethyl)-6-ethyl-1-methyl-1H-benzimidazole

A mixture of methyl 1-methyl-6-vinyl-1H-benzimidazole-7-carboxylate (3.7 g), 10% palladium-carbon (3.7 g) and ethanol (160 mL) was stirred under a hydrogen gas atmosphere at room temperature for 2 hr. The reaction mixture was filtered, and the filtrate was concentrated under reduced pressure. A solution of the obtained residue in THF (60 mL) was added dropwise to a suspension of lithium aluminum hydride (979 mg) in THF (60 mL) at 0° C. After stirring at room temperature for 2 hr, sodium sulfate.10 hydrate was added to the reaction mixture. The precipitated insoluble material was filtered off through celite, and the filtrate was concentrated under reduced pressure. To a mixture of the obtained residue, DBU (3.9 g) and toluene (100 mL) was added DPPA (7.1 g) at 0° C., and the mixture was stirred at room temperature for 15 hr. To the mixture was added saturated aqueous ammonium chloride solution, and the mixture was extracted with ethyl acetate. The organic layer was separated, washed with water and saturated brine, dried over anhydrous magnesium sulfate and concentrated under reduced pressure. The residue was purified by silica gel column chromatography (NH, ethyl acetate/hexane) to give the title compound (3.3 g).

$^1$H NMR (300 MHz, DMSO-$d_6$) δ 1.12-1.28 (3H, m), 2.83 (2H, q, J=7.4 Hz), 4.04 (3H, s), 4.91 (2H, s), 7.13 (1H, d, J=8.3 Hz), 7.58 (1H, d, J=8.3 Hz), 8.09 (1H, s).

C) 1-(6-ethyl-1-methyl-1H-benzimidazol-7-yl)methanamine dihydrochloride

A mixture of 7-(azidomethyl)-6-ethyl-1-methyl-1H-benzimidazole (1.1 g), triphenylphosphine (1.5 g), THF (25 mL) and water (5 mL) was stirred at 60° C. for 2 hr. The reaction mixture was concentrated, the obtained residue was dissolved in ethyl acetate, and 4.0 M hydrogen chloride ethyl acetate solution (3.8 mL) was added. The precipitated solid was collected by filtration and washed with ethyl acetate to give the title compound (1.3 g).

$^1$H NMR (300 MHz, DMSO-d$_6$) δ 1.22 (3H, t, J=7.4 Hz), 2.94 (2H, q, J=7.6 Hz), 4.33 (3H, s), 4.50 (2H, d, J=5.3 Hz), 7.52 (1H, d, J=8.3 Hz), 7.84 (1H, d, J=8.7 Hz), 8.46-9.12 (3H, m), 9.46 (1H, s).

D) 6-(difluoromethoxy)-N-((6-ethyl-1-methyl-1H-benzimidazol-7-yl)methyl)-5-fluoronicotinamide To a mixture of 1-(6-ethyl-1-methyl-1H-benzimidazol-7-yl)methanamine dihydrochloride (55 mg) and DMA (1 mL) were added HOBt·H$_2$O (39 mg), WSC·HCl (48 mg), 6-(difluoromethoxy)-5-fluoronicotinic acid (48 mg) and triethylamine (110 mg) at room temperature, and the mixture was stirred for 3 hr. To the mixture was added water, and the precipitated solid was collected by filtration and purified by silica gel column chromatography (NH, ethyl acetate/hexane) to give the title compound (42 mg).

$^1$H NMR (300 MHz, DMSO-d$_6$) δ 1.17 (3H, t, J=7.6 Hz), 2.75 (2H, q, J=7.3 Hz), 4.02 (3H, s), 4.88 (2H, d, J=4.2 Hz), 7.11 (1H, d, J=8.3 Hz), 7.47-8.02 (2H, m), 8.05-8.13 (1H, m), 8.35 (1H, dd, J=10.8, 2.1 Hz), 8.57 (1H, d, J=1.9 Hz), 8.90-9.05 (1H, m).

Example 152

N-((1,6-dimethyl-1H-benzimidazol-7-yl)methyl)-4-(trifluoromethoxy)benzamide

To a mixture of 1-(1,6-dimethyl-1H-benzimidazol-7-yl)methanamine dihydrochloride (60 mg) and DMF (2.0 mL) were added HOBt·H$_2$O (44 mg), WSC·HCl (65 mg), 4-(trifluoromethoxy)benzoic acid (60 mg) and triethylamine (120 mg) at room temperature and the mixture was stirred overnight. To the mixture was added water, and the precipitated solid was collected by filtration to give the title compound (60 mg).

$^1$H NMR (300 MHz, DMSO-d$_6$) δ 2.42 (3H, s), 4.02 (3H, s), 4.86 (2H, d, J=4.5 Hz), 7.07 (1H, d, J=8.3 Hz), 7.38-7.46 (2H, m), 7.49 (1H, d, J=8.0 Hz), 7.95-8.03 (2H, m), 8.05 (1H, s), 8.82 (1H, t, J=4.4 Hz).

Example 193

5-fluoro-6-methoxy-N-((5-methyl-1H-benzotriazol-4-yl)methyl)nicotinamide

A) methyl 6-chloro-2-((4-methoxybenzyl)amino)-3-nitrobenzoate

To a mixture of methyl 2,6-dichloro-3-nitrobenzoate (2.5 g), triethylamine (2.1 mL) and tetrahydrofuran (50 mL) was added 4-methoxybenzylamine (2.0 mL) at room temperature over 15 min, and the mixture was refluxed for 10 hr. To the mixture was added water, THF was evaporated under reduced pressure, and the mixture was neutralized with 1 N hydrochloric acid. The mixture was extracted with ethyl acetate, washed with water and saturated brine, dried over anhydrous magnesium sulfate, and concentrated under reduced pressure. The residue was purified by silica gel column chromatography (ethyl acetate/hexane) to give the title compound (2.0 g).

$^1$H NMR (400 MHz, DMSO-d$_6$) δ 3.75 (3H, s), 3.89 (3H, s), 4.27 (2H, d, J=4.7 Hz), 6.93 (3H, t, J=8.6 Hz), 7.27 (2H, d, J=7.6 Hz), 8.08-8.20 (2H, m).

B) methyl 2-amino-6-chloro-3-nitrobenzoate

A mixture of methyl 6-chloro-2-((4-methoxybenzyl)amino)-3-nitrobenzoate (2.5 g) and TFA (12 mg) was stirred at room temperature for 2 hr. The reaction mixture was concentrated, the obtained residue was partitioned with an ethyl acetate-saturated aqueous sodium hydrogen carbonate solution, and the organic layer was washed with saturated brine, dried over anhydrous magnesium sulfate and concentrated under reduced pressure. The residue was purified by silica gel column chromatography (ethyl acetate/hexane) to give the title compound (1.3 g).

$^1$H NMR (400 MHz, DMSO-d$_6$) δ 3.91 (3H, s), 6.81 (1H, d, J=9.2 Hz), 7.47 (2H, s), 8.12 (1H, d, J=9.2 Hz).

C) methyl 2,3-diamino-6-chlorobenzoate

To a mixture of methyl 2-amino-6-chloro-3-nitrobenzoate (4.5 g), acetone (200 mL) and water (20 mL) were added zinc (13 g) and ammonium chloride (16 g) under ice-cooling, and the mixture was stirred at room temperature for 3 hr. Insoluble material was filtered through celite, and the filtrate was concentrated. The obtained residue was dissolved in dichloromethane, washed with water and saturated brine, dried over anhydrous magnesium sulfate and concentrated under reduced pressure. The residue was purified by silica gel column chromatography (ethyl acetate/hexane) to give the title compound (3.1 g).

$^1$H NMR (400 MHz, DMSO-d$_6$) δ 3.82 (3H, s), 4.87 (2H, s), 5.01 (2H, s), 6.47 (1H, d, J=8.3 Hz), 6.55 (1H, d, J=8.3 Hz).

D) methyl 5-chloro-1H-benzotriazole-4-carboxylate

To a mixture of methyl 2,3-diamino-6-chlorobenzoate (3.1 g) and acetic acid (28 mL) was added a solution of sodium nitrite (1.6 g) in water (7 mL) at room temperature, and the mixture was stirred at room temperature for 3 hr. To the mixture was added saturated aqueous sodium carbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (2.2 g).

$^1$H NMR (400 MHz, DMSO-d$_6$) δ 4.00 (3H, s), 7.58 (1H, d, J=8.8 Hz), 8.23-8.30 (1H, m).

E) methyl 5-chloro-1-(tetrahydro-2H-pyran-2-yl)-1H-benzotriazole-4-carboxylate or methyl 5-chloro-2-(tetrahydro-2H-pyran-2-yl)-2H-benzotriazole-4-carboxylate or methyl 6-chloro-1-(tetrahydro-2H-pyran-2-yl)-1H-benzotriazole-7-carboxylate To a solution of methyl 5-chloro-1H-benzotriazole-4-carboxylate (2.1 g) in dichloromethane (40 mL) were added 3,4-dihydro-2H-pyran (4.5 mL) and p-toluenesulfonic acid·monohydrate (0.17 g) at room temperature, and the mixture was stirred at room temperature for 16 hr. To the mixture was added water, and the mixture was extracted with dichloromethane. The organic layer was separated, washed with water and saturated brine, dried over anhydrous magnesium sulfate, and concentrated under reduced pressure. The residue was purified by silica gel column chromatography (ethyl acetate/hexane) to give the title compound (2.8 g).

$^1$H NMR (400 MHz, DMSO-d$_6$) δ 1.20-4.70 (11H, s), 6.24 (1H, dd, J=8.9, 2.8 Hz), 7.75 (1H, d, J=8.9 Hz), 8.12 (1H, d, J=8.9 Hz).

F) methyl 5-methyl-1-(tetrahydro-2H-pyran-2-yl)-1H-benzotriazole-4-carboxylate or methyl 5-methyl-2-(tetrahydro-2H-pyran-2-yl)-2H-benzotriazole-4-carboxylate or methyl 6-methyl-1-(tetrahydro-2H-pyran-2-yl)-1H-benzotriazole-7-carboxylate To a mixture of methyl 5-chloro-1-(tetrahydro-2H-pyran-2-yl)-1H-benzotriazole-4-carboxylate or methyl 5-chloro-2-(tetrahydro-2H-pyran-2-yl)-2H-benzotriazole-4-carboxylate or methyl 6-chloro-1-(tetrahydro-2H-pyran-2-yl)-1H-benzotriazole-7-carboxylate (1.5 g), dioxane (9 mL) and DMF (3 mL) were added trimethylboroxine (2.2 mL), potassium phosphate (2.2 g), tricyclophosphine (140 mg) and palladium acetate (57 mg), and the mixture was deaerated for 15 min and stirred at 120° C. for 16 hr. Insoluble material was filtered off through celite, water was added to the filtrate, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (500 mg).

$^1$H NMR (400 MHz, DMSO-$d_6$) δ 1.65 (3H, dd, J=8.1, 4.3 Hz), 1.71-1.84 (3H, m), 1.99-2.10 (1H, m), 2.12-2.14 (1H, m), 2.39-2.47 (1H, m), 3.81-3.84 (1H, m), 3.86 (1H, t, J=3.6 Hz), 3.96 (3H, s), 6.18 (1H, dd, J=9.2, 2.7 Hz), 7.53 (1H, d, J=8.6 Hz), 7.97 (1H, d, J=8.5 Hz).

G) 1-(5-methyl-1-(tetrahydro-2H-pyran-2-yl)-1H-benzotriazol-4-yl)methanamine or 1-(5-methyl-2-(tetrahydro-2H-pyran-2-yl)-2H-benzotriazol-4-yl)methanamine or 1-(6-methyl-1-(tetrahydro-2H-pyran-2-yl)-1H-benzotriazol-7-yl)methanamine To a mixture of methyl 5-methyl-1-(tetrahydro-2H-pyran-2-yl)-1H-benzotriazole-4-carboxylate or methyl 5-chloro-2-(tetrahydro-2H-pyran-2-yl)-2H-benzotriazole-4-carboxylate or methyl 6-chloro-1-(tetrahydro-2H-pyran-2-yl)-1H-benzotriazole-7-carboxylate (450 mg) and THE (5 mL) was added 2 M lithium aluminum hydride THE solution (2.45 mL) at 0° C., and the mixture was stirred for 4 hr. To the mixture was added saturated aqueous ammonium chloride solution, and the mixture was extracted with ethyl acetate. The organic layer was separated, washed with water and saturated brine, dried over anhydrous magnesium sulfate, and concentrated under reduced pressure to give (5-methyl-1-(tetrahydro-2H-pyran-2-yl)-1H-benzotriazol-4-yl)methanol or (5-methyl-2-(tetrahydro-2H-pyran-2-yl)-2H-benzotriazol-4-yl)methanol or (6-methyl-1-(tetrahydro-2H-pyran-2-yl)-1H-benzotriazol-7-yl)methanol (425 mg). To a mixture of this compound (425 mg) and dichloromethane (5 mL) were added mesyl chloride (0.2 mL) and triethylamine (0.71 mL) at room temperature, and the mixture was stirred at room temperature for 4 hr. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give 4-(chloromethyl)-5-methyl-1-(tetrahydro-2H-pyran-2-yl)-1H-benzotriazole or 4-(chloromethyl)-5-methyl-2-(tetrahydro-2H-pyran-2-yl)-2H-benzotriazole or 7-(chloromethyl)-6-methyl-1-(tetrahydro-2H-pyran-2-yl)-1H-benzotriazole (260 mg). To a mixture of this compound (130 mg) and DMF (2 mL) was added sodium azide (130 mg), and the mixture was stirred at room temperature for 16 hr. To the mixture was added water, and the mixture was extracted with ethyl acetate. The organic layer was separated, washed with water and saturated brine, dried over anhydrous magnesium sulfate, and concentrated under reduced pressure. The residue was dissolved in THE (3 mL), 2 M lithium aluminum hydride THE solution (0.36 mL) was added at 0° C., and the mixture was stirred for 1 hr. To the mixture was added 1 M aqueous sodium hydroxide solution (0.10 mL), and the mixture was stirred at room temperature for 1 hr. To the mixture was added ethyl acetate (50 mL), and the mixture was dried over anhydrous magnesium sulfate, and concentrated under reduced pressure to give the title compound (100 mg).

$^1$H NMR (400 MHz, DMSO-$d_6$) δ 1.62-1.67 (3H, m), 1.74-1.88 (2H, m), 2.01-2.13 (3H, m), 2.47 (3H, s), 3.75-3.81 (1H, m), 3.89 (1H, d, J=11.4 Hz), 4.18 (2H, s), 6.11 (1H, dd, J=9.1, 2.1 Hz), 7.37 (1H, d, J=8.5 Hz), 7.63 (1H, d, J=8.4 Hz).

H) 5-fluoro-6-methoxy-N-((5-methyl-1-(tetrahydro-2H-pyran-2-yl)-1H-benzotriazol-4-yl)methyl)nicotinamide or 5-fluoro-6-methoxy-N-((5-methyl-2-(tetrahydro-2H-pyran-2-yl)-2H-benzotriazol-4-yl)methyl)nicotinamide or 5-fluoro-6-methoxy-N-((6-methyl-1-(tetrahydro-2H-pyran-2-yl)-1H-benzotriazol-7-yl)methyl)nicotinamide To a mixture of 1-(5-methyl-1-(tetrahydro-2H-pyran-2-yl)-1H-benzotriazol-4-yl)methanamine or 1-(5-methyl-2-(tetrahydro-2H-pyran-2-yl)-2H-benzotriazol-4-yl)methanamine or 1-(6-methyl-1-(tetrahydro-2H-pyran-2-yl)-1H-benzotriazol-7-yl)methanamine (70 mg), 5-fluoro-6-methoxynicotinic acid (73 mg) and dichloromethane (3 mL) were added WSC·HCl (82 mg) and DMAP (69 mg) at room temperature, and the mixture was stirred at room temperature for 16 hr. To the mixture was added water, and the mixture was extracted with dichloromethane. The organic layer was separated, washed with water and saturated brine, dried over anhydrous magnesium sulfate, and concentrated under reduced pressure. The residue was purified by silica gel column chromatography (ethyl acetate/hexane) to give the title compound (80 mg).

$^1$H NMR (400 MHz, CDCl$_3$) δ 1.71-1.78 (2H, m), 1.79-1.89 (1H, m), 2.12-2.26 (2H, m), 2.55 (3H, s), 2.57-2.63 (1H, m), 3.72-3.83 (1H, m), 3.88-3.97 (1H, m), 4.06 (3H, s), 5.11 (2H, d, J=4.5 Hz), 5.97-6.04 (1H, m), 7.33 (1H, d, J=8.5 Hz), 7.55 (1H, d, J=8.6 Hz), 7.87 (1H, d, J=10.6 Hz), 8.51 (1H, s), 8.76-8.84 (1H, m).

I) 5-fluoro-6-methoxy-N-((5-methyl-1H-benzotriazol-4-yl)methyl)nicotinamide

To a mixture of 5-fluoro-6-methoxy-N-((5-methyl-1-(tetrahydro-2H-pyran-2-yl)-1H-benzotriazol-4-yl)methyl)nicotinamide or 5-fluoro-6-methoxy-N-((5-methyl-2-(tetrahydro-2H-pyran-2-yl)-2H-benzotriazol-4-yl)methyl)nicotinamide or 5-fluoro-6-methoxy-N-((6-methyl-1-(tetrahydro-2H-pyran-2-yl)-1H-benzotriazol-7-yl)methyl)nicotinamide (65 mg) and acetonitrile (5 mL) was added 10 N hydrochloric acid (0.13 mL) at 0° C., and the mixture was stirred at room temperature for 2 hr. To the mixture was added water, and the mixture was basified with saturated sodium carbonate and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (45 mg).

¹H NMR (400 MHz, DMSO-d₆) δ 2.47 (3H, s), 3.98 (3H, s), 4.87 (2H, s), 7.27 (1H, d, J=8.4 Hz), 7.77 (1H, d, J=9.6 Hz), 8.07 (1H, dd, J=11.4, 1.6 Hz), 8.51 (1H, d, J=1.5 Hz), 8.92 (1H, s), 15.60 (1H, s).

Example 207

3,5-difluoro-4-methoxy-N-((5-methoxy-1H-benzotriazol-4-yl)methyl)benzamide

A) methyl 2,3-diamino-6-methoxybenzoate

A mixture of methyl 2-amino-6-methoxy-3-nitrobenzoate (2.5 g), 10% palladium-carbon (1.2 g) and methanol (150 mL) was stirred under a hydrogen gas atmosphere at room temperature for 15 hr. The reaction mixture was filtered, insoluble material was washed with methanol, and the filtrate was concentrated under reduced pressure to give the title compound (2.1 g).
¹H NMR (300 MHz, DMSO-d₆) δ 3.60 (3H, s), 3.75 (3H, s), 4.26 (2H, brs), 5.03 (2H, brs), 6.08 (1H, d, J=8.3 Hz), 6.58 (1H, d, J=8.3 Hz).

B) methyl 5-methoxy-1H-benzotriazole-4-carboxylate

To a mixture of methyl 2,3-diamino-6-methoxybenzoate (2.1 g), acetic acid (27 mL) and water (11 mL) was added a solution of sodium nitrite (0.89 g) in water (5.4 mL) at 0° C., and the mixture was stirred at 0° C. for 1 hr. To the mixture was added water, and the precipitated solid was collected by filtration and washed with water to give the title compound (1.3 g).
¹H NMR (300 MHz, DMSO-d₆) δ 3.90 (3H, s), 3.98 (3H, s), 7.35 (1H, d, J=9.1 Hz), 8.27 (1H, d, J=9.1 Hz).

C) methyl 5-methoxy-1-(tetrahydro-2H-pyran-2-yl)-1H-benzotriazole-4-carboxylate or methyl 5-methoxy-2-(tetrahydro-2H-pyran-2-yl)-2H-benzotriazole-4-carboxylate or methyl 6-methoxy-1-(tetrahydro-2H-pyran-2-yl)-1H-benzotriazole-7-carboxylate A mixture of methyl 5-methoxy-1H-benzotriazole-4-carboxylate (1.5 g), 3,4-dihydro-2H-pyran (3.0 g), p-toluenesulfonic acid.monohydrate (0.14 g) and DMF (72 mL) was stirred at 60° C. overnight. The mixture was neutralized with a saturated aqueous sodium hydrogen carbonate solution at 0° C. and extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (390 mg).
¹H NMR (300 MHz, CDCl₃) δ 1.47-1.88 (3H, m), 2.06-2.23 (1H, m), 2.32-2.46 (1H, m), 2.66-2.82 (1H, m), 3.44-3.56 (1H, m), 3.57-3.69 (1H, m), 3.97 (3H, s), 3.99 (3H, s), 5.85-5.95 (1H, m), 7.13 (1H, d, J=9.0 Hz), 8.09 (1H, d, J=9.0 Hz).

D) (5-methoxy-1-(tetrahydro-2H-pyran-2-yl)-1H-benzotriazol-4-yl)methanol or (5-methoxy-2-(tetrahydro-2H-pyran-2-yl)-2H-benzotriazol-4-yl)methanol or (6-methoxy-1-(tetrahydro-2H-pyran-2-yl)-1H-benzotriazol-7-yl)methanol To a mixture of 2.5 M lithium aluminum hydride THF solution (0.80 mL) and THF (6.7 mL) was added a solution of methyl 5-methoxy-1-(tetrahydro-2H-pyran-2-yl)-1H-benzotriazole-4-carboxylate or methyl 5-methoxy-2-(tetrahydro-2H-pyran-2-yl)-2H-benzotriazole-4-carboxylate or methyl 6-methoxy-1-(tetrahydro-2H-pyran-2-yl)-1H-benzotriazole-7-carboxylate (0.39 g) in THF (6.7 mL) at 0° C. After stirring at room temperature for 1 hr, sodium sulfate.10 hydrate was added to the reaction mixture. The precipitated insoluble material was filtered off through celite, and the filtrate was concentrated under reduced pressure. The residue was purified by silica gel column chromatography (ethyl acetate/hexane) to give the title compound (250 mg).
¹H NMR (300 MHz, CDCl₃) δ 1.60-1.92 (3H, m), 2.18-2.39 (2H, m), 2.67-2.88 (1H, m), 3.05 (1H, brs), 3.73-3.96 (5H, m), 4.83-4.95 (1H, m), 5.18 (1H, d, J=12.5 Hz), 6.17 (1H, dd, J=2.7, 8.1 Hz), 7.07 (1H, d, J=9.0 Hz), 7.92 (1H, d, J=9.0 Hz).

E) 1-(5-methoxy-1-(tetrahydro-2H-pyran-2-yl)-1H-benzotriazol-4-yl)methanamine or 1-(5-methoxy-2-(tetrahydro-2H-pyran-2-yl)-2H-benzotriazol-4-yl)methanamine or 1-(6-methoxy-1-(tetrahydro-2H-pyran-2-yl)-1H-benzotriazol-7-yl)methanamine To a mixture of (5-methoxy-1-(tetrahydro-2H-pyran-2-yl)-1H-benzotriazol-4-yl)methanol or (5-methoxy-2-(tetrahydro-2H-pyran-2-yl)-2H-benzotriazol-4-yl)methanol or (6-methoxy-1-(tetrahydro-2H-pyran-2-yl)-1H-benzotriazol-7-yl)methanol (0.25 g) and DMF (5.3 mL) were added DBU (0.22 g) and DPPA (0.39 g), and the mixture was stirred at room temperature overnight. To the mixture was added water, and the mixture was extracted with ethyl acetate. The organic layer was separated, washed with water and saturated brine, dried over anhydrous magnesium sulfate, and concentrated under reduced pressure. A mixture of the obtained residue, triphenylphosphine (290 mg), THF (4 mL) and water (0.79 mL) was stirred at room temperature for 15 hr. The reaction mixture was concentrated, the obtained residue was partitioned with ethyl acetate-water, and the organic layer was washed with saturated brine, dried over anhydrous magnesium sulfate and concentrated under reduced pressure. The residue was purified by silica gel column chromatography (NH, ethyl acetate/hexane) to give the title compound (250 mg).
MS: [M+H]⁺ 263.2.

F) 3,5-difluoro-4-methoxy-N-((5-methoxy-1H-benzotriazol-4-yl)methyl)benzamide

To a mixture of 1-(5-methoxy-1-(tetrahydro-2H-pyran-2-yl)-1H-benzotriazol-4-yl)methanamine or 1-(5-methoxy-2-(tetrahydro-2H-pyran-2-yl)-2H-benzotriazol-4-yl)methanamine or 1-(6-methoxy-1-(tetrahydro-2H-pyran-2-yl)-1H-benzotriazol-7-yl)methanamine (50 mg) and DMF (1.6 mL) were added HOBt·H₂O (35 mg), WSC·HCl (51 mg), 3,5-difluoro-4-methoxybenzoic acid (43 mg) and triethylamine (96 mg) at room temperature, and the mixture was stirred overnight. To the mixture was added water, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane). The obtained residue was dissolved in ethyl acetate (2 mL), 4.0 M hydrogen chloride ethyl acetate solution (4 mL) was added, and the mixture was stirred at room temperature for 1 hr. The reaction mixture was concentrated, the obtained residue was partitioned with an ethyl acetate-saturated aqueous sodium hydrogen carbonate solution, and the organic layer was washed with saturated brine, dried over anhydrous magnesium sulfate and concentrated under reduced pressure. The residue was purified by silica gel column chromatography (ethyl acetate/hexane) to give the title compound (12 mg).

$^1$H NMR (400 MHz, DMSO-d$_6$) δ3.91 (3H, s), 3.98 (3H, s), 4.74 (2H, d, J=4.9 Hz), 7.27 (1H, d, J=9.1 Hz), 7.59-7.75 (2H, m), 7.92 (1H, d, J=9.1 Hz), 8.85 (1H, t, J=4.7 Hz), 15.47 (1H, brs).

Example 215

1-((6-methoxy-1-methyl-1H-benzimidazol-7-yl)methyl)-3-(3-methylphenyl)urea

To a mixture of 1-(6-methoxy-1-methyl-1H-benzimidazol-7-yl)methanamine and dichloromethane (2 mL) were added triethylamine (0.03 mL) and 3-methylphenyl isocyanate (41 mg), and the mixture was stirred at room temperature for 2 hr. The reaction mixture was concentrated, and the residue was separated by HPLC (C18, mobile phase: water/acetonitrile (containing 20 mM ammonium formate)) to give the title compound (4.8 mg).

MS: [M+H]$^+$ 325.2.

Example 272

N-[(3-bromo-1H-indazol-4-yl)methyl]-3-fluoro-4-(trifluoromethoxy)benzamide $^1$H NMR (300 MHz, DMSO-d$_6$) δ 5.06 (2H, d, J=5.4 Hz), 7.06 (1H, d, J=7.1 Hz), 7.37 (1H, t, J=7.6 Hz), 7.49 (1H, d, J=8.3 Hz), 7.71-7.78 (1H, m), 7.90 (1H, d, J=8.7 Hz), 8.03 (1H, dd, J=11.2, 2.0 Hz), 9.23 (1H, t, J=5.4 Hz), 13.50 (1H, brs).

The Example compounds are shown in the following Tables 1-1 to 48. In the Tables, MS shows Found values. When the MS in the Tables is ND, it means that MS was not detected. The compounds of Examples 9-15, 18, 19, 21-116, 118-133, 135-138, 140-142, 144-151, 153-192, 194-206, 208-214, 216-284 in the following Tables were produced according to the methods shown in the above-mentioned Examples or methods analogous thereto.

TABLE 1-1

| Example No. | IUPAC name | structural formula | salt | MS |
|---|---|---|---|---|
| 1 | N-((2,5-dimethyl-2H-indazol-4-yl)methyl)-4-(trifluoromethoxy)benzamide | | | 364.2 |
| 2 | N-((5-methyl-1H-indazol-4-yl)methyl)-4-(trifluoromethoxy)benzamide | | | 350.1 |
| 3 | N-((5-methyl-1H-benzimidazol-4-yl)methyl)-4-(trifluoromethoxy)benzamide | | | 350.3 |
| 4 | N-((5-iodo-1H-indazol-4-yl)methyl)-4-(trifluoromethoxy)benzamide | | | 459.9 |
| 5 | 4-(trifluoromethoxy)-N-((5-(trifluoromethyl)-1H-indazol-4-yl)methyl)benzamide | | | 401.9 |

TABLE 1-1-continued

| Example No. | IUPAC name | structural formula | salt | MS |
|---|---|---|---|---|
| 6 | N-((5-methoxy-1H-indazol-4-yl)methyl)-4-(trifluoromethoxy)benzamide | | | 366.1 |

TABLE 1-2

| Example No. | IUPAC name | structural formula | salt | MS |
|---|---|---|---|---|
| 7 | N-(1H-indazol-4-ylmethyl)-4-(trifluoromethoxy)benzamide | | | 333.9 |
| 8 | 3,5-difluoro-4-methoxy-N-((6-methoxy-1-methyl-1H-benzimidazol-7-yl)methyl)benzamide | | | 362.1 |
| 9 | 3,5-difluoro-N-((6-methoxy-1-methyl-1H-benzimidazol-7-yl)methyl)-4-methylbenzamide | | | 346.2 |
| 10 | 5-fluoro-6-methoxy-N-((6-methoxy-1-methyl-1H-benzimidazol-7-yl)methyl)nicotinamide | | | 345.2 |
| 11 | 3-fluoro-4-methoxy-N-((6-methoxy-1-methyl-1H-benzimidazol-7-yl)methyl)benzamide | | | 344.2 |

TABLE 1-2-continued

| Example No. | IUPAC name | structural formula | salt | MS |
|---|---|---|---|---|
| 12 | N-((6-methoxy-1-methyl-1H-benzimidazol-7-yl)methyl)-4-(trifluoromethoxy)benzamide | | | 380.2 |

TABLE 1-3

| Example No. | IUPAC name | structural formula | salt | MS |
|---|---|---|---|---|
| 13 | 3-fluoro-N-((6-methoxy-1-methyl-1H-benzimidazol-7-yl)methyl)-4-(trifluoromethyl)benzamide | | | 380 |
| 14 | 3-fluoro-N-((6-methoxy-1-methyl-1H-benzimidazol-7-yl)methyl)-4-methylbenzamide | | | 328.2 |
| 15 | 4-chloro-3,5-difluoro-N-((6-methoxy-1-methyl-1H-benzimidazol-7-yl)methyl)benzamide | | | 366.1 |
| 16 | N-((5-ethyl-1H-indazol-4-yl)methyl)-3,5-difluoro-4-methoxybenzamide | | | 346.2 |
| 17 | N-((5-cyclopropyl-1H-indazol-4-yl)methyl)-3,5-difluoro-4-methoxybenzamide | | | 358.2 |

TABLE 1-3-continued

| Example No. | IUPAC name | structural formula | salt | MS |
|---|---|---|---|---|
| 18 | 3-chloro-4,5-difluoro-N-((6-methoxy-1-methyl-1H-benzimidazol-7-yl)methyl)benzamide | | | 366.1 |

TABLE 1-4

| Example No. | IUPAC name | structural formula | salt | MS |
|---|---|---|---|---|
| 19 | N-((1,6-dimethyl-1H-benzimidazol-7-yl)methyl)-5-fluoro-6-methoxynicotinamide | | | 329.2 |
| 20 | N-((6-cyclopropyl-1-methyl-1H-benzimidazol-7-yl)methyl)-5-fluoro-6-methoxynicotinamide | | | 355.2 |
| 21 | N-((6-cyclopropyl-1-methyl-1H-benzimidazol-7-yl)methyl)-3,5-difluoro-4-methoxybenzamide | | | 372.2 |
| 22 | N-((6-ethyl-1-methyl-1H-benzimidazol-7-yl)methyl)-5-fluoro-6-methoxynicotinamide | | | 343.2 |
| 23 | N-((6-ethyl-1-methyl-1H-benzimidazol-7-yl)methyl)-3,5-difluoro-4-methoxybenzamide | | | 360.2 |

TABLE 1-4-continued

| Example No. | IUPAC name | structural formula | salt | MS |
|---|---|---|---|---|
| 24 | 3,5-difluoro-N-((6-methoxy-1-methyl-1H-benzimidazol-7-yl)methyl)-4-(trifluoromethyl)benzamide | | | 398 |

15

TABLE 1-5

| Example No. | IUPAC name | structural formula | salt | MS |
|---|---|---|---|---|
| 25 | N-((1,6-dimethyl-1H-benzimidazol-7-yl)methyl)-3,5-difluoro-4-methoxybenzamide | | | 346.2 |
| 26 | N-((1,6-dimethyl-1H-benzimidazol-7-yl)methyl)-3,5-difluoro-4-(trifluoromethylbenzamide | | | 382 |
| 27 | N-((6-methoxy-1-methyl-1H-benzimidazol-7-yl)methyl)-5-methylthiophene-3-carboxamide | | | 316.1 |
| 28 | 5-chloro-N-((6-methoxy-1-methyl-1H-benzimidazol-7-yl)methyl)thiophene-3-carboxamide | | | 336.1 |
| 29 | 5-ethyl-N-((6-methoxy-1-methyl-1H-benzimidazol-7-yl)methyl)thiophene-3-carboxamide | | | 330.2 |

TABLE 1-5-continued

| Example No. | IUPAC name | structural formula | salt | MS |
|---|---|---|---|---|
| 30 | N-((1,6-dimethyl-1H-benzimidazol-7-yl)methyl)-3-fluoro-4-(trifluoromethoxy)benzamide | | | 382.1 |

TABLE 1-6

| Example No. | IUPAC name | structural formula | salt | MS |
|---|---|---|---|---|
| 31 | 3-chloro-4-(difluoromethoxy)-N-((1,6-dimethyl-1H-benzimidazol-7-yl)methyl)benzamide | | | 378 |
| 32 | N-((6-methoxy-1-methyl-1H-benzimidazol-7-yl)methyl)-5-methylthiophene-2-carboxamide | | | 316.2 |
| 33 | N-((6-methoxy-1-methyl-1H-benzimidazol-7-yl)methyl)-2-(2-thienyl)acetamide | | | 316.2 |
| 34 | 3-chloro-4-methoxy-N-((6-methoxy-1-methyl-1H-benzimidazol-7-yl)methyl)benzamide | | | 360.1 |
| 35 | 4-methoxy-N-((6-methoxy-1-methyl-1H-benzimidazol-7-yl)methyl)-3,5-dimethylbenzamide | | | 354.2 |

TABLE 1-6-continued

| Example No. | IUPAC name | structural formula | salt | MS |
|---|---|---|---|---|
| 36 | 5-chloro-N-((6-methoxy-1-methyl-1H-benzimidazol-7-yl)methyl)thiophene-2-carboxamide | | | 336.1 |

TABLE 1-7

| Example No. | IUPAC name | structural formula | salt | MS |
|---|---|---|---|---|
| 37 | 3-chloro-4-fluoro-N-((6-methoxy-1-methyl-1H-benzimidazol-7-yl)methyl)benzamide | | | 348.1 |
| 38 | 3-chloro-N-((6-methoxy-1-methyl-1H-benzimidazol-7-yl)methyl)-4-methylbenzamide | | | 344.1 |
| 39 | 4-chloro-N-((6-methoxy-1-methyl-1H-benzimidazol-7-yl)methyl)-3-methylbenzamide | | | 344.1 |
| 40 | 4-fluoro-N-((6-methoxy1-methyl-1H-benzimidazol-7-yl)methyl)-3-(trifluoromethyl)benzamide | | | 382.1 |
| 41 | 3,4,5-trifluoro-N-((6-methoxy-1-methyl-1H-benzimidazol-7-yl)methyl)benzamide | | | 348 |

TABLE 1-7-continued

| Example No. | IUPAC name | structural formula | salt | MS |
|---|---|---|---|---|
| 42 | 4-chloro-N-((6-methoxy-1-methyl-1H-benzimidazol-7-yl)methyl)thiophene-2-carboxamide | | | 336.1 |

TABLE 1-8

| Example No. | IUPAC name | structural formula | salt | MS |
|---|---|---|---|---|
| 43 | N-((6-methoxy-1-methyl-1H-benzimidazol-7-yl)methyl)-4-methylthiophene-2-carboxamide | | | 316.2 |
| 44 | 4-chloro-3-fluoro-N-((6-methoxy-1-methyl-1H-benzimidazol-7-yl)methyl)benzamide | | | 348.2 |
| 45 | 4-chloro-3-methoxy-N-((6-methoxy-1-methyl-1H-benzimidazol-7-yl)methyl)benzamide | | | 360.1 |
| 46 | 4-fluoro-3-methoxy-N-((6-methoxy-1-methyl-1H-benzimidazol-7-yl)methyl)benzamide | | | 344.2 |
| 47 | N-((6-methoxy-1-methyl-1H-benzimidazol-7-yl)methyl)-4-methyl-3-(trifluoromethyl)benzamide | | | 378.2 |

TABLE 1-8-continued

| Example No. | IUPAC name | structural formula | salt | MS |
|---|---|---|---|---|
| 48 | 5-methoxy-N-((6-methoxy-1-methyl-1H-benzimidazol-7-yl)methyl)thiopene-2-carboxamide | | | 332.2 |

TABLE 1-9

| Example No. | IUPAC name | structural formula | salt | MS |
|---|---|---|---|---|
| 49 | 3,5-dichloro-4-fluoro-N-((6-methoxy-1-methyl-1H-benzimidazol-7-yl)methyl)benzamide | | | 382.1 |
| 50 | N-((6-methoxy-1-methyl-1H-benzimidazol-7-yl)methyl)-5-(trifluoromethyl)thiophene-2-carboxamide | | | 367.9 |
| 51 | 3-chloro-N-((6-methoxy-1-methyl-1H-benzimidazol-7-yl)methyl)-4-(trifluoromethyl)benzamide | | | 398.1 |
| 52 | 3-fluoro-N-((6-methoxy-1-methyl-1H-benzimidazol-7-yl)methyl)-4-(trifluoromethoxy)benzamide | | | 398.2 |

TABLE 1-9-continued

| Example No. | IUPAC name | structural formula | salt | MS |
|---|---|---|---|---|
| 53 | 4,5-dichloro-N-((6-methoxy-1-methyl-1H-benzimidazol-7-yl)methyl)thiophene-2-carboxamide | | | 370 |
| 54 | 3,4-difluoro-N-((6-methoxy-1-methyl-1H-benzimidazol-7-yl)methyl)-5-methylbenzamide | | | 346.2 |

TABLE 1-10

| Example No. | IUPAC name | structural formula | salt | MS |
|---|---|---|---|---|
| 55 | 3,4-dichloro-5-fluoro-N-((6-methoxy-1-methyl-1H-benzimidazol-7-yl)methyl)benzamide | | | 382.1 |
| 56 | N-((6-methoxy-1-methyl-1H-benzimidazol-7-yl)methyl)-6-(trifluoromethoxy)-nicotinamide | | | 379 |
| 57 | 5-chloro-6-methoxy-N-((6-methoxy-1-methyl-1H-benzimidazol-7-yl)methyl)nicotinamide | | | 361.1 |

TABLE 1-10-continued

| Example No. | IUPAC name | structural formula | salt | MS |
|---|---|---|---|---|
| 58 | 5-chloro-6-ethoxy-N-((6-methoxy-1-methyl-1H-benzimidazol-7-yl)methyl)nicotinamide | | | 375.2 |
| 59 | 6-(difluoromethoxy)-5-fluoro-N-((6-methoxy-1-methyl-1H-benzimidazol-7-yl)methyl)nicotinamide | | | 381.2 |
| 60 | 3-chloro-N-((1,6-dimethyl-1H-benzimidazol-7-yl)methyl)-4-(trifluoromethoxy)benzamide | | | 396 |

TABLE 1-11

| Example No. | IUPAC name | structural formula | salt | MS |
|---|---|---|---|---|
| 61 | N-((5-cyclopropyl-1H-indazol-4-yl)methyl)-4-(trifluoromethyl)benzamide | | | 360.1 |
| 62 | N-((5-cyclopropyl-1H-indazol-4-yl)methyl)-4-(trifluoromethoxy)benzamide | | | 376.1 |
| 63 | N-((5-cyclopropyl-1H-indazol-4-yl)methyl)-4-methylthiophene-2-carboxamide | | | 312.2 |

TABLE 1-11-continued

| Example No. | IUPAC name | structural formula | salt | MS |
|---|---|---|---|---|
| 64 | N-((5-cyclopropyl-1H-indazol-4-yl)methyl)-5-methylthiophene-2-carboxmaide | | | 312.2 |
| 65 | N-((5-cyclopropyl-1H-indazol-4-yl)methyl)-2-(2-thienyl)acetamide | | | 312.2 |
| 66 | N-((5-cyclopropyl-1H-indazol-4-yl)methyl)-5-methylthiophene-3-carboxamide | | | 310.1 |

TABLE 1-12

| Example No. | IUPAC name | structural formula | salt | MS |
|---|---|---|---|---|
| 67 | N-((5-cyclopropyl-1H-indazol-4-yl)methyl)-5-methoxythiophene-2-carboxamide | | | 328.1 |
| 68 | N-((5-cyclopropyl-1H-indazol-4-yl)methyl)-4-methoxythiophene-2-carboxamide | | | 328.2 |
| 69 | 5-chloro-N-((5-cyclopropyl-1H-indazol-4-yl)methyl)thiophene-3-carboxamide | | | 329.9 |

TABLE 1-12-continued

| Example No. | IUPAC name | structural formula | salt | MS |
|---|---|---|---|---|
| 70 | 4-chloro-N-((5-cyclopropyl-1H-indazol-4-yl)methyl)thiophene-2-carboxamide | | | 332.2 |
| 71 | 5-chloro-N-((5-cyclopropyl-1H-indazol-4-yl)methyl)thiophene-2-carboxamide | | | 332.2 |
| 72 | N-((5-cyclopropyl-1H-indazol-4-yl)methyl)-4-fluoro-3-methoxybenzamide | | | 338.1 |

TABLE 1-13

| Example No. | IUPAC name | structural formula | salt | MS |
|---|---|---|---|---|
| 73 | 4-chloro-N-((5-cyclopropyl-1H-indazol-4-yl)methyl)-3-methylbenzamide | | | 340.2 |
| 74 | 3-chloro-N-((5-cyclopropyl-1H-indazol-4-yl)methyl)-4-methylbenzamide | | | 338 |
| 75 | N-((5-cyclopropyl-1H-indazol-4-yl)methyl)-4-fluoro-3-methylbenzamide | | | 322 |

TABLE 1-13-continued

| Example No. | IUPAC name | structural formula | salt | MS |
|---|---|---|---|---|
| 76 | N-((5-cyclopropyl-1H-indazol-4-yl)methyl)-3,4-difluoro-5-methylbenzamide | | | 342.1 |
| 77 | 3-chloro-N-((5-cyclopropyl-1H-indazol-4-yl)methyl)-4-fluorobenzamide | | | 342 |
| 78 | 4-chloro-N-((5-cyclopropyl-1H-indazol-4-yl)methyl)-3-fluorobenzamide | | | 342 |

TABLE 1-14

| Example No. | IUPAC name | structural formula | salt | MS |
|---|---|---|---|---|
| 79 | N-((5-cyclopropyl-1H-indazol-4-yl)methyl)-3,4,5-trifluorobenzamide | | | 344 |
| 80 | 3-chloro-N-((5-cyclopropyl-1H-indazol-4-yl)methyl)-4-methoxybenzamide | | | 356.2 |
| 81 | 4-chloro-N-((5-cyclopropyl-1H-indazol-4-yl)methyl)-3-methoxybenzamide | | | 356.2 |

TABLE 1-14-continued

| Example No. | IUPAC name | structural formula | salt | MS |
|---|---|---|---|---|
| 82 | N-((5-cyclopropyl-1H-indazol-4-yl)methyl)-5-(trifluoromethyl)thiophene-2-carboxamide | | | 366.1 |
| 83 | 4,5-dichloro-N-((5-cyclopropyl-1H-indazol-4-yl)methyl)thiophene-2-carboxamide | | | 366 |
| 84 | N-((5-cyclopropyl-1H-indazol-4-yl)methyl)-4-methyl-3-(trifluoromethyl)benzamide | | | 374.2 |

TABLE 1-15

| Example No. | IUPAC name | structural formula | salt | MS |
|---|---|---|---|---|
| 85 | N-((5-cyclopropyl-1H-indazol-4-yl)methyl)-4-fluoro-3-(trifluoromethyl)benzamide | | | 378.2 |
| 86 | 3,5-dichloro-N-((5-cyclopropyl-1H-indazol-4-yl)methyl)-4-fluorobenzamide | | | 378.1 |
| 87 | 3,4-dichloro-N-((5-cyclopropyl-1H-indazol-4-yl)methyl)-5-fluorobenzamide | | | 378.1 |

TABLE 1-15-continued

| Example No. | IUPAC name | structural formula | salt | MS |
|---|---|---|---|---|
| 88 | N-((5-cyclopropyl-1H-indazol-4-yl)methyl)-3-fluoro-4-(trifluoromethoxy)benzamide | | | 392 |
| 89 | 3-chloro-N-((5-cyclopropyl-1H-indazol-4-yl)methyl)-4-(trifluoromethyl)benzamide | | | 392 |
| 90 | 4-chloro-N-((5-cyclopropyl-1H-indazol-4-yl)methyl)-3,5-difluorobenzamide | | | 362.1 |

TABLE 1-16

| Example No. | IUPAC name | structural formula | salt | MS |
|---|---|---|---|---|
| 91 | N-((5-cyclopropyl-1H-indazol-4-yl)methyl)-3,5-difluoro-4-(trifluoromethyl)benzamide | | | 394 |
| 92 | N-((5-cyclopropyl-1H-indazol-4-yl)methyl)-3-fluoro-4-(trifluoromethyl)benzamide | | | 378.2 |
| 93 | N-((5-cyclopropyl-1H-indazol-4-yl)methyl)-3-fluoro-4-methylbenzmaide | | | 322 |

TABLE 1-16-continued

| Example No. | IUPAC name | structural formula | salt | MS |
|---|---|---|---|---|
| 94 | N-((5-cyclopropyl-1H-indazol-4-yl)methyl)-3-fluoro-4-methoxybenzamide | | | 337.9 |
| 95 | 3-chloro-N-((5-cyclopropyl-1H-indazol-4-yl)methyl)-4,5-difluorobenzamide | | | 362.1 |
| 96 | N-((5-cyclopropyl-1H-indazol-4-yl)methyl)-5-fluoro-6-methoxynicotinamide | | | 339 |

TABLE 1-17

| Example No. | IUPAC name | structural formula | salt | MS |
|---|---|---|---|---|
| 97 | N-((5-cyclopropyl-1H-indazol-4-yl)methyl)-3,5-difluoro-4-methylbenzamide | | | 342.1 |
| 98 | N-((5-cyclopropyl-1H-indazol-4-yl)methyl)-4-(difluoromethyl)benzamide | | | 342.1 |
| 99 | N-((5-cyclopropyl-1H-indazol-4-yl)methyl)-4-methylbenzamide | | | 304 |

TABLE 1-17-continued

| Example No. | IUPAC name | structural formula | salt | MS |
|---|---|---|---|---|
| 100 | N-((5-cyclopropyl-1H-indazol-4-yl)methyl)-4-(difluoromethoxy)benzamide | 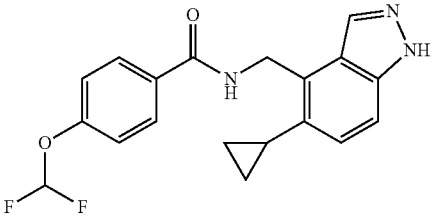 [SMILES: O=C(NCc1c(C2CC2)ccc2[nH]ncc12)c1ccc(OC(F)F)cc1] | | 358.2 |
| 101 | N-((5-cyclopropyl-1H-indazol-4-yl)methyl)-4-methoxybenzamide | 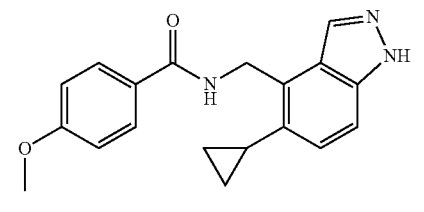 [SMILES: COc1ccc(C(=O)NCc2c(C3CC3)ccc3[nH]ncc23)cc1] | | 320 |
| 102 | 4-chloro-N-((5-cyclopropyl-1H-indazol-4-yl)methyl)benzamide | 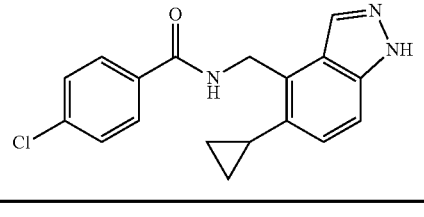 | | 324 |

TABLE 1-18

| Example No. | IUPAC name | structural formula | salt | MS |
|---|---|---|---|---|
| 103 | 5-chloro-N-((5-cyclopropyl-1H-indazol-4-yl)methyl)-6-methoxynicotinamide | 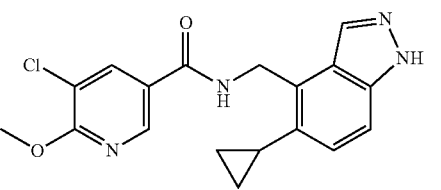 [SMILES: COc1ncc(C(=O)NCc2c(C3CC3)ccc3[nH]ncc23)cc1Cl] | | 357.1 |
| 104 | 5-chloro-N-((5-cyclopropyl-1H-indazol-4-yl)methyl)-6-ethoxynicotinamide | 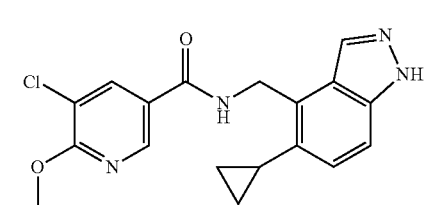 | | 371.2 |
| 105 | N-((5-cyclopropyl-1H-indazol-4-yl)methyl)-6-(difluoromethoxy)-5-fluoronicotinamide | 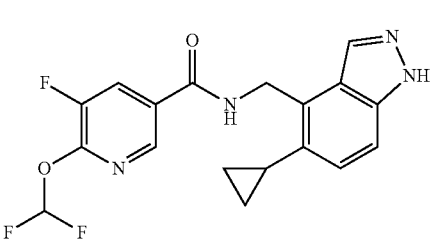 [SMILES: O=C(NCc1c(C2CC2)ccc2[nH]ncc12)c1cnc(OC(F)F)c(F)c1] | | 377.2 |

TABLE 1-18-continued

| Example No. | IUPAC name | structural formula | salt | MS |
|---|---|---|---|---|
| 106 | N-((5-cyclopropyl-1H-indazol-4-yl)methyl)-6-(trifluoromethoxy)-nicotinamide | 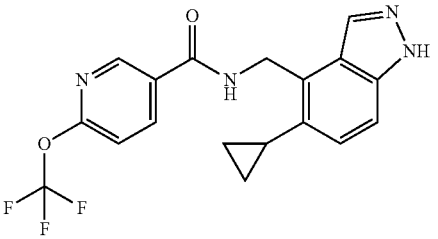 [SMILES: O=C(NCc1c(C2CC2)ccc2[nH]ncc12)c1ccc(OC(F)(F)F)nc1] | | 375 |
| 107 | 3-chloro-N-((5-cyclopropyl-1H-indazol-4-yl)methyl)-4-(difluoromethxoy)-benzamide | 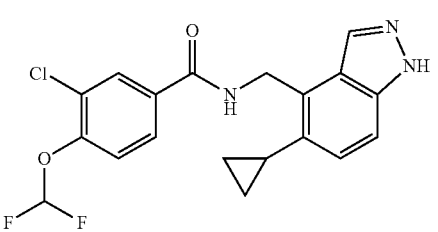 [SMILES: O=C(NCc1c(C2CC2)ccc2[nH]ncc12)c1ccc(OC(F)F)c(Cl)c1] | | 392.1 |
| 108 | N-((5-cyclopropyl-1H-indazol-4-yl)methyl)-4-(difluoromethyl)-3,5-difluorobenzamide | 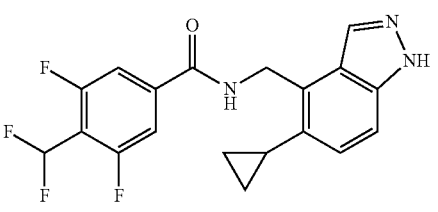 [SMILES: O=C(NCc1c(C2CC2)ccc2[nH]ncc12)c1cc(F)c(C(F)F)c(F)c1] | | 376 |

TABLE 1-19

| Example No. | IUPAC name | structural formula | salt | MS |
|---|---|---|---|---|
| 109 | 4-(difluoromethoxy)-N-((1,6-dimethyl-1H-benzimidazol-7-yl)methyl)-3-fluorobenzamide | 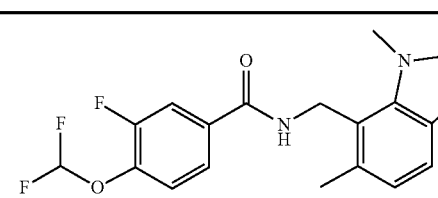 | | 364.2 |
| 110 | 5-(difluoromethyl)-N-((6-methoxy-1-methyl-1H-benzimidazol-7-yl)methyl)thiophene-3-carboxamide | 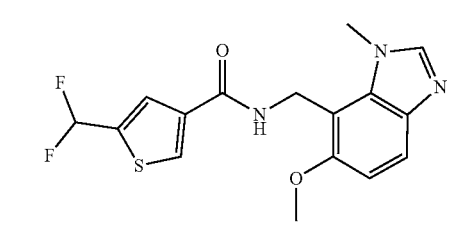 [SMILES: COc1ccc2ncn(C)c2c1CNC(=O)c1csc(C(F)F)c1] | | 352.1 |
| 111 | 3-chloro-5-fluoro-4-methoxy-N-((6-methoxy-1-methyl-1H-benzimidazol-7-yl)methyl)benzamide | 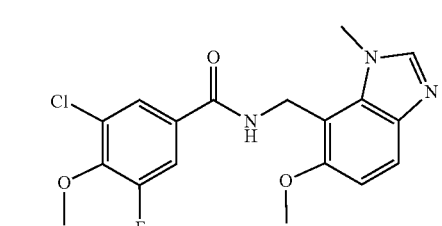 | | 378.1 |

TABLE 1-19-continued

| Example No. | IUPAC name | structural formula | salt | MS |
|---|---|---|---|---|
| 112 | 3-chloro-4-(difluoromethyl)-N-((6-methoxy-1-methyl-1H-benzimidazol-7-yl)methyl)benzamide | | | 380.2 |
| 113 | 5-chloro-N-((6-methoxy-1-methyl-1H-benzimidazol-7-yl)methyl)-6-(trifluoromethyl)-nicotinamide | | | 397 |
| 114 | N-((6-methoxy-1-methyl-1H-benzimidazol-7-yl)methyl)-4-methylbenzamide | | | 310.3 |

TABLE 1-20

| Example No. | IUPAC name | structural formula | salt | MS |
|---|---|---|---|---|
| 115 | 5-cyclopropyl-N-((6-methoxy-1-methyl-1H-benzimidazol-7-yl)methyl)thiophene-3-carboxamide | | | 342.1 |
| 116 | 4-chloro-N-((6-methoxy-1-methyl-1H-benzimidazol-7-yl)methyl)benzamide | | | 330.2 |
| 117 | N-((6-methoxy-1-methyl-1H-benzimidazol-7-yl)methyl)-4-(trifluoromethyl)benzamide | | | 364.1 |

TABLE 1-20-continued

| Example No. | IUPAC name | structural formula | salt | MS |
|---|---|---|---|---|
| 118 | N-((5-cyclopropyl-1H-indazol-4-yl)methyl)-4-(difluoromethyl)-3-fluorobenzamide | 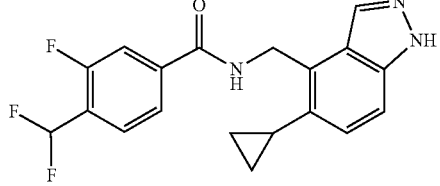 | | 360.1 |
| 119 | N-((5-cyclopropyl-1H-indazol-4-yl)methyl)-6-ethoxy-5-fluoronicotinamide | 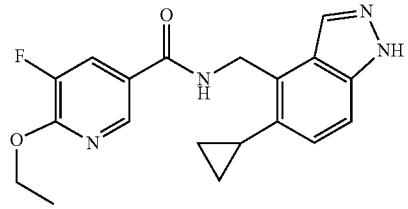 [SMILES: CCOc1ncc(C(=O)NCc2c(C3CC3)ccc3[nH]ncc23)cc1F] | | 355.2 |
| 120 | N-((5-cyclopropyl-1H-indazol-4-yl)methyl)-4-(difluoromethoxy)-3-fluorobenzamide | 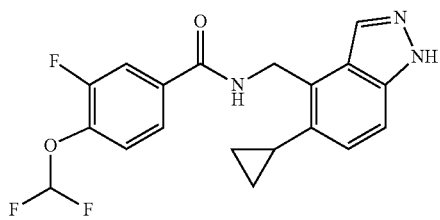 [SMILES: O=C(NCc1c(C2CC2)ccc2[nH]ncc12)c1ccc(OC(F)F)c(F)c1] | | 376.1 |

TABLE 1-21

| Example No. | IUPAC name | structural formula | salt | MS |
|---|---|---|---|---|
| 121 | 5-chloro-N-((5-cyclopropyl-1H-indazol-4-yl)methyl)-6-(difluoromethoxy)-nicotinamide | 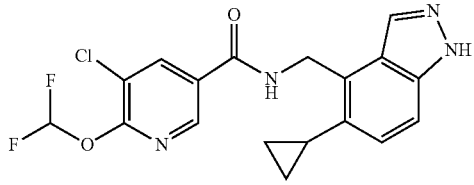 [SMILES: O=C(NCc1c(C2CC2)ccc2[nH]ncc12)c1cnc(OC(F)F)c(Cl)c1] | | 391 |
| 122 | 5-ethyl-N-((6-methoxy-1-methyl-1H-benzimidazol-7-yl)methyl)thiophene-2-carboxamide | 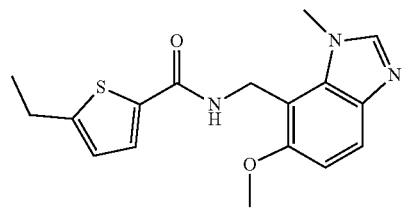 [SMILES: CCc1ccc(C(=O)NCc2c(OC)ccc3ncn(C)c23)s1] | | 330.2 |
| 123 | 4-(difluoromethyl)-N-((6-methoxy-1-methyl-1H-benzimidazol-7-yl)methyl)benzamide | 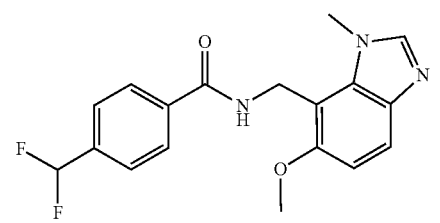 [SMILES: COc1ccc2ncn(C)c2c1CNC(=O)c1ccc(C(F)F)cc1] | | 346.2 |

TABLE 1-21-continued

| Example No. | IUPAC name | structural formula | salt | MS |
|---|---|---|---|---|
| 124 | 4-(difluoromethyl)-3-fluoro-N-((6-methoxy-1-methyl-1H-benzimidazol-7-yl)methyl)benzamide | 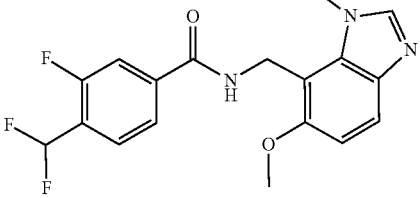 | | 364.2 |
| 125 | 5-(difluoromethyl)-N-((6-ethoxy-1-methyl-1H-benzimidazol-7-yl)methyl)thiophene-3-carboxamide | 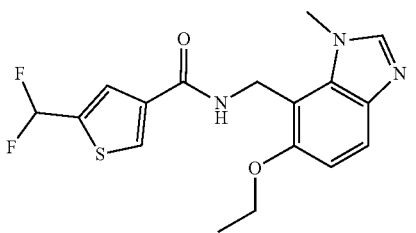 | | 366.1 |
| 126 | 5-(difluoromethyl)-N-((6-ethoxy-1-methyl-1H-benzimidazol-7-yl)methyl)thiophene-2-carboxamide | 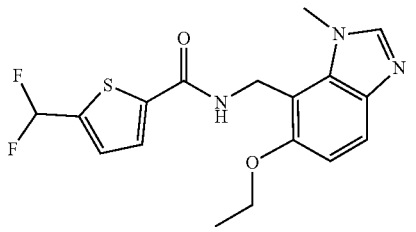 [SMILES: CCOc1ccc2ncn(C)c2c1CNC(=O)c1ccc(C(F)F)s1] | | 366.1 |

TABLE 1-22

| Example No. | IUPAC name | structural formula | salt | MS |
|---|---|---|---|---|
| 127 | N-((6-ethoxy-1-methyl-1H-benzimidazol-7-yl)methyl)-3,5-difluoro-4-methoxybenzamide | 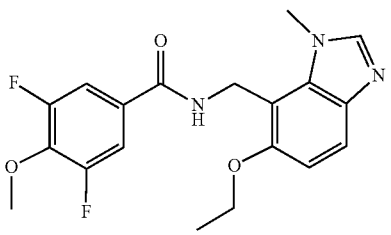 [SMILES: CCOc1ccc2ncn(C)c2c1CNC(=O)c1cc(F)c(OC)c(F)c1] | | 376.1 |
| 128 | N-((6-ethoxy-1-methyl-1H-benzimidazol-7-yl)methyl)-4-(trifluoromethyl)-benzamide | 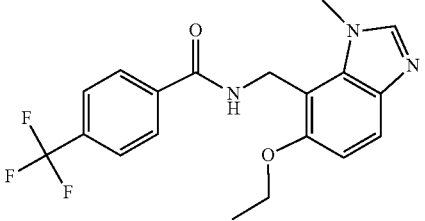 [SMILES: CCOc1ccc2ncn(C)c2c1CNC(=O)c1ccc(C(F)(F)F)cc1] | | 378.2 |
| 129 | N-((1,6-dimethyl-1H-benzimidazol-7-yl)methyl)-3-fluoro-4-methoxybenzamide | 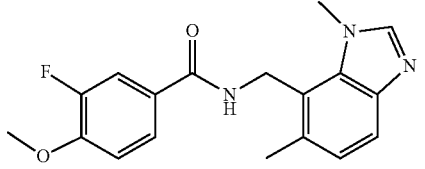 [SMILES: COc1ccc(C(=O)NCc2c(C)ccc3ncn(C)c23)cc1F] | | 328.2 |

TABLE 1-22-continued

| Example No. | IUPAC name | structural formula | salt | MS |
|---|---|---|---|---|
| 130 | N-((6-ethyl-1-methyl-1H-benzimidazol-7-yl)methyl)-3-fluoro-4-methoxybenzamide | | | 342.2 |
| 131 | 4-(difluoromethoxy)-N-((6-ethyl-1-methyl-1H-benzimidazol-7-yl)methyl)-3,5-difluorobenzamide | | | 394 |
| 132 | 5-(difluoromethyl)-N-((6-ethyl-1-methyl-1H-benzimidazol-7-yl)methyl)thiophene-3-carboxamide | | | 348 |

TABLE 1-23

| Example No. | IUPAC name | structural formula | salt | MS |
|---|---|---|---|---|
| 133 | 4-(difluoromethyl)-N-((6-ethyl-1-methyl-1H-benzimidazol-7-yl)methyl)benzamide | | | 344.2 |
| 134 | 6-(difluoromethoxy)-N-((1,6-dimethyl-1H-benzimidazol-7-yl)methyl)-5-fluoronicotinamide | | | 365.1 |
| 135 | 4-(difluoromethoxy)-N-((1,6-dimethyl-1H-benzimidazol-7-yl)methyl)benzamide | | | 346.2 |

TABLE 1-23-continued

| Example No. | IUPAC name | structural formula | salt | MS |
|---|---|---|---|---|
| 136 | 4-(difluoromethyl)-N-((1,6-dimethyl-1H-benzimidazol-7-yl)methyl)-3-fluorobenzamide | | | 348.2 |
| 137 | 5-(difluoromethyl)-N-((1,6-dimethyl-1H-benzimidazol-7-yl)methyl)thiophene-2-carboxamide | | | 334 |
| 138 | N-((1,6-dimethyl-1H-benzimidazol-7-yl)methyl)-6-(trifluoromethoxy)-nicotinamide | | | 365.1 |

TABLE 1-24

| Example No. | IUPAC name | structural formula | salt | MS |
|---|---|---|---|---|
| 139 | N-((6-methoxy-1-methyl-1H-benzimidazol-7-yl)methyl)-5-(trifluoromethyl)-thiophene-3-carboxamide | | | 370.1 |
| 140 | 4-(difluoromethyl)-N-((6-ethoxy-1-methyl-1H-benzimidazol-7-yl)methyl)benzamide | | | 360.2 |
| 141 | 4-(difluoromethyl)-N-((6-ethoxy-1-methyl-1H-benzlmidazol-7-yl)methyl)-3-fluorobenzamide | | | 378.2 |

TABLE 1-24-continued

| Example No. | IUPAC name | structural formula | salt | MS |
|---|---|---|---|---|
| 142 | 5-(difluoromethyl)-N-((1,6-dimethyl-1H-benzimidazol-7-yl)methyl)thiophene-3-carboxamide | | | 334 |
| 143 | 6-(difluoromethoxy)-N-((6-ethyl-1-methyl-1H-benzimidazol-7-yl)methyl)-5-fluoronicotinamide | | | 379.2 |
| 144 | 5-cyclopropyl-N-((1,6-dimethyl-1H-benzimidazol-7-yl)methyl)thiophene-3-carboxamide | | | 326.2 |

TABLE 1-25

| Example No. | IUPAC name | structural formula | salt | MS |
|---|---|---|---|---|
| 145 | N-((6-ethyl-1-methyl-1H-benzimidazol-7-yl)methyl)-4-methoxybenzamide | | | 324.3 |
| 146 | 4-(difluoromethyl)-N-((6-ethyl-1-methyl-1H-benzimidazol-7-yl)methyl)-3-fluorobenzamide | | | 362.1 |
| 147 | 5-chloro-N-((6-ethyl-1-methyl-1H-benzimidazol-7-yl)methyl)thiophene-3-carboxamide | | | 332 |
| 148 | 4-(difluoromethoxy)-N-((6-ethyl-1-methyl-1H-benzimidazol-7-yl)methyl)benzamide | | | 360.2 |

TABLE 1-25-continued

| Example No. | IUPAC name | structural formula | salt | MS |
|---|---|---|---|---|
| 149 | N-((6-ethyl-1-methyl-1H-benzimidazol-7-yl)methyl)-6-(trifluoromethoxy)-nicotinamide | | | 379.1 |
| 150 | N-((1-ethyl-6-methoxy-1H-benzimidazol-7-yl)methyl)-5-fluoro-6-methoxynicotinamide | | | 359.2 |

TABLE 1-26

| Example No. | IUPAC name | structural formula | salt | MS |
|---|---|---|---|---|
| 151 | N-((1-ethyl-6-methoxy-1H-benzimidazol-7-yl)methyl)-3,5-difluoro-4-methoxybenzamide | | | 376.1 |
| 152 | N-((1,6-dimethyl-1H-benzimidazol-7-yl)methyl)-4-(trifluoromethoxy)-benzamide | | | 364.2 |
| 153 | N-((5-cyclopropyl-1H-indazol-4-yl)methyl)-4-(difluoromethoxy)-3,5-difluorobenzamide | | | 394.1 |
| 154 | N-((5-cyclopropyl-1H-indazol-4-yl)methyl)-5-(difluoromethyl)-thiophene-3-carboxamide | | | 346 |
| 155 | N-((5-cyclopropyl-1H-indazol-4-yl)methyl)-5-(difluoromethyl)-thiophene-2-carboxamide | | | 348.2 |

TABLE 1-26-continued

| Example No. | IUPAC name | structural formula | salt | MS |
|---|---|---|---|---|
| 156 | 5-chloro-N-((1,6-dimethyl-1H-benzimidazol-7-yl)methyl)thiophene-3-carboxamide | | | 317.9 |

TABLE 1-27

| Example No. | IUPAC name | structural formula | salt | MS |
|---|---|---|---|---|
| 157 | 4-(difluoromethyl)-N-((1,6-dimethyl-1H-benzimidazol-7-yl)methyl)benzamide | | | 330.2 |
| 158 | 4-(difluoromethoxy)-N-((1,6-dimethyl-1H-benzimidazol-7-yl)methyl)-3,5-difluorobenzamide | | | 382.1 |
| 159 | 6-(difluoromethoxy)-N-((1,6-dimethyl-1H-benzimidazol-7-yl)methyl)nicotinamide | | | 347.2 |
| 160 | 3,5-difluoro-4-methoxy-N-((1-methyl-1H-benzimidazol-7-yl)methyl)benzamide | | | 332.2 |
| 161 | 4-(difluoromethoxy)-3,5-difluoro-N-((6-methoxy-1-methyl-1H-benzimidazol-7-yl)methyl)benzamide | | | 396 |

TABLE 1-27-continued

| Example No. | IUPAC name | structural formula | salt | MS |
|---|---|---|---|---|
| 162 | N-((6-methoxy-1-methyl-1H-benzimidazol-7-yl)methyl)-5-(trifluoromethyl)-thiophene-2-carboxamide hydrochloride | | HCl | 370.3 |

TABLE 1-28

| Example No. | IUPAC name | structural formula | salt | MS |
|---|---|---|---|---|
| 163 | N-((1,6-dimethyl-1H-benzimidazol-7-yl)methyl)-5-(trifluoromethyl)-thiophene-3-carboxamide | | | 354.1 |
| 164 | 6-(difluoromethoxy)-N-((6-ethyl-1-methyl-1H-benzimidazol-7-yl)methyl)nicotinamide | | | 361.1 |
| 165 | N-((5-cyclopropyl-1H-benzotriazol-4-yl)methyl)-5-fluoro-6-methoxynicotinamide | | | 342.1 |
| 166 | 5-chloro-N-(1H-indazol-4-ylmethyl)thiophene-3-carboxamide | | | 292 |
| 167 | N-(1H-indazol-4-ylmethyl)-5-(trifluoromethyl)-thiophene-2-carboxamide | | | 326 |
| 168 | 4,5-dichloro-N-(1H-indazol-4-ylmethyl)thiophene-2-carboxamide | | | 326 |

TABLE 1-29

| Example No. | IUPAC name | structural formula | salt | MS |
|---|---|---|---|---|
| 169 | 5-chloro-N-(1H-indazol-4-ylmethyl)-6-methoxynicotinamide | | | 317.1 |
| 170 | N-(1H-indazol-4-ylmethyl)-6-(trifluoromethoxy)-nicotinamide | | | 337 |
| 171 | 6-ethoxy-5-fluoro-N-(1H-indazol-4-ylmethyl)nicotinamide | | | 315.1 |
| 172 | 5-fluoro-N-(1H-indazol-4-ylmethyl)-6-methoxynicotinamide | | | 301.1 |
| 173 | 3,5-difluoro-N-(1H-indazol-4-ylmethyl)-4-(trifluoromethyl)-benzamide | | | 354 |
| 174 | 3-fluoro-N-(1H-indazol-4-ylmethyl)-4-(trifluoromethyl)-benzamide | | | 338.1 |

TABLE 1-30

| Example No. | IUPAC name | structural formula | salt | MS |
|---|---|---|---|---|
| 175 | N-(1H-indazol-4-ylmethyl)-4-(trifluoromethyl)-benzamide | | | 320.1 |

TABLE 1-30-continued

| Example No. | IUPAC name | structural formula | salt | MS |
|---|---|---|---|---|
| 176 | 3-fluoro-N-(1H-indazol-4-ylmethyl)-4-methylbenzamide | | | 284.1 |
| 177 | 4-(difluoromethyl)-N-(1H-indazol-4-ylmethyl)benzamide | | | 302.1 |
| 178 | 4-(difluoromethyl)-3-fluoro-N-(1H-indazol-4-ylmethyl)benzamide | | | 318 |
| 179 | 3-fluoro-N-(1H-indazol-4-ylmethyl)-4-(trifluoromethoxy)-benzamide | | | 354.1 |
| 180 | 3,5-difluoro-N-(1H-indazol-4-ylmethyl)-4-methoxybenzamide | | | 318.1 |

TABLE 1-31

| Example No. | IUPAC name | structural formula | salt | MS |
|---|---|---|---|---|
| 181 | 3-fluoro-N-(1H-indazol-4-ylmethyl)-4-methoxybenzamide | | | 300.1 |

TABLE 1-31-continued

| Example No. | IUPAC name | structural formula | salt | MS |
|---|---|---|---|---|
| 182 | 3-chloro-4-(difluoromethoxy)-N-(1H-indazol-4-ylmethyl)benzamide | | | 352 |
| 183 | 4-(difluoromethoxy)-N-(1H-indazol-4-ylmethyl)benzamide | | | 318.1 |
| 184 | 4-(difluoromethoxy)-3,5-difluoro-N-(1H-indazol-4-ylmethyl)benzamide | | | 354 |
| 185 | 3-chloro-N-(1H-indazol-4-ylmethyl)-4-methylbenzamide | | | 300.1 |
| 186 | 3-chloro-4-fluoro-N-(1H-indazol-4-ylmethyl)benzamide | | | 304.1 |

TABLE 1-32

| Example No. | IUPAC name | structural formula | salt | MS |
|---|---|---|---|---|
| 187 | 4-chloro-3-fluoro-N-(1H-indazol-4-ylmethyl)benzamide | | | 304.1 |
| 188 | 3-chloro-4,5-difluoro-N-(1H-indazol-4-ylmethyl)benzamide | | | 322 |

TABLE 1-32-continued

| Example No. | IUPAC name | structural formula | salt | MS |
|---|---|---|---|---|
| 189 | 4-chloro-3,5-difluoro-N-(1H-indazol-4-ylmethyl)benzamide | | | 322 |
| 190 | 3-chloro-4-(difluoromethyl)-N-(1H-indazol-4-ylmethyl)benzamide | | | 336.1 |
| 191 | 6-(difluoromethoxy)-5-fluoro-N-(1H-indazol-4-ylmethyl)nicotinamide | | | 337 |
| 192 | 4-(difluoromethoxy)-3-fluoro-N-(1H-indazol-4-ylmethyl)benzamide | | | 336.1 |

TABLE 1-33

| Example No. | IUPAC name | structural formula | salt | MS |
|---|---|---|---|---|
| 193 | 5-fluoro-6-methoxy-N-((5-methyl-1H-benzotriazol-4-yl)methyl)nicotinamide | | | 316.1 |
| 194 | N-((5-methyl-1H-benzotriazol-4-yl)methyl)-4-(trifluoromethoxy)-benzamide | | | 351.1 |
| 195 | 3,5-difluoro-N-((5-methyl-1H-benzotriazol-4-yl)methyl)-4-(trifluoromethyl)-benzamide | | | 371.1 |

TABLE 1-33-continued

| Example No. | IUPAC name | structural formula | salt | MS |
|---|---|---|---|---|
| 196 | 3,5-difluoro-4-methyl-N-((5-methyl-1H-benzotriazol-4-yl)methyl)benzamide | | | 317.3 |
| 197 | 3,5-difluoro-4-methoxy-N-((5-methyl-1H-benzotriazol-4-yl)methyl)benzamide | | | 333.1 |
| 198 | 4-chloro-3,5-difluoro-N-((5-methyl-1H-benzotriazol-4-yl)methyl)benzamide | | | 337 |

TABLE 1-34

| Example No. | IUPAC name | structural formula | salt | MS |
|---|---|---|---|---|
| 199 | 3-fluoro-N-((5-methyl-1H-benzotriazol-4-yl)methyl)-4-(trifluoromethyl)-benzamide | | | 353 |
| 200 | 3-fluoro-4-methyl-N-((5-methyl-1H-benzotriazol-4-yl)methyl)benzamide | | | 299.2 |
| 201 | 3-fluoro-4-methoxy-N-((5-methyl-1H-benzotriazol-4-yl)methyl))benzamide | | | 315.2 |
| 202 | 3-chloro-4,5-difluoro-N-((5-methyl-1H-benzotriazol-4-yl)methyl)benzamide | | | 337 |

TABLE 1-34-continued

| Example No. | IUPAC name | structural formula | salt | MS |
|---|---|---|---|---|
| 203 | N-((5-cyclopropyl-1H-benzotriazol-4-yl)methyl)-4-(trifluoromethoxy)-benzamide | 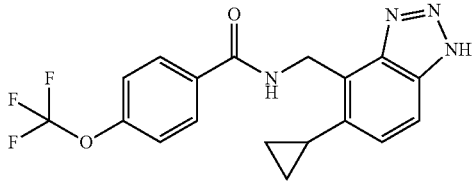 [SMILES: O=C(NCc1c(C2CC2)ccc2[nH]nnc12)c1ccc(OC(F)(F)F)cc1] | | 377.1 |
| 204 | N-((5-cyclopropyl-1H-benzotriazol-4-yl)methyl)-3,5-difluoro-4-methoxybenzamide | 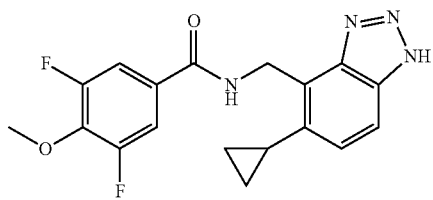 [SMILES: COc1c(F)cc(C(=O)NCc2c(C3CC3)ccc3[nH]nnc23)cc1F] | | 359.1 |

TABLE 1-35

| Example No. | IUPAC name | structural formula | salt | MS |
|---|---|---|---|---|
| 205 | N-((5-ethyl-1H-benzotriazol-4-yl)methyl)-3,5-difluoro-4-(trifluoromethyl)-benzamide | 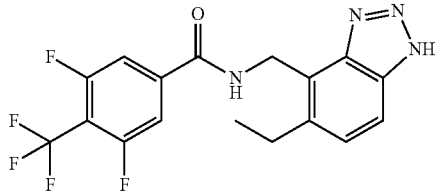 [SMILES: CCc1ccc2[nH]nnc2c1CNC(=O)c1cc(F)c(C(F)(F)F)c(F)c1] | | 383 |
| 206 | N-((5-ethyl-1H-benzotriazol-4-yl)methyl)-3,5-difluoro-4-methoxybenzamide | 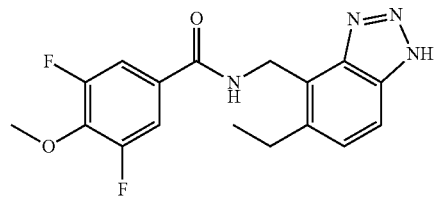 [SMILES: CCc1ccc2[nH]nnc2c1CNC(=O)c1cc(F)c(OC)c(F)c1] | | 347.1 |
| 207 | 3,5-difluoro-4-methoxy-N-((5-methoxy-1H-benzotriazol-4-yl)methyl)benzamide | 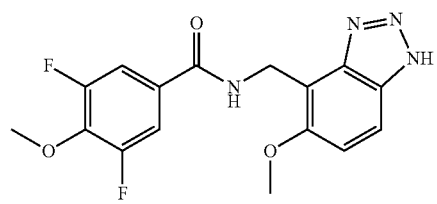 [SMILES: COc1ccc2[nH]nnc2c1CNC(=O)c1cc(F)c(OC)c(F)c1] | | 349.1 |
| 208 | N-((5-ethyl-1H-benzotriazol-4-yl)methyl)-5-fluoro-6-methoxynicotinamide | 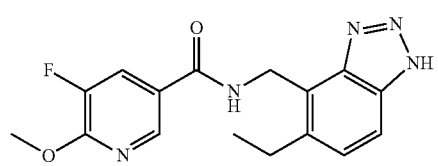 [SMILES: CCc1ccc2[nH]nnc2c1CNC(=O)c1cnc(OC)c(F)c1] | | 330.2 |

TABLE 1-35-continued

| Example No. | IUPAC name | structural formula | salt | MS |
|---|---|---|---|---|
| 209 | N-((5-ethyl-1H-benzotriazol-4-yl)methyl)-4-(trifluoromethoxy)-benzamide | | | 365.1 |
| 210 | 3,5-difluoro-N-((6-fluoro-1-methyl-1H-benzimidazol-7-yl)methyl)-4-methoxybenzamide | | | 350.1 |

TABLE 1-36

| Example No. | IUPAC name | structural formula | salt | MS |
|---|---|---|---|---|
| 211 | N-(1H-benzotriazol-4-ylmethyl)-3,5-difluoro-4-methoxybenzamide | | | 319.1 |
| 212 | N-((5-cyclopropyl-1H-benzotriazol-4-yl)methyl)-4-(difluoromethoxy)-3-fluorobenzamide | | | 377.1 |
| 213 | N-((5-methoxy-1H-benzotriazol-4-yl)methyl)-4-(trifluoromethoxy)-benzamide | | | 365 |
| 214 | 3,5-difluoro-4-methoxy-N-((6-methoxy-1,2-dimethyl-1H-benzimidazol-7-yl)methyl)benzamide | | | 376.1 |

TABLE 1-36-continued

| Example No. | IUPAC name | structural formula | salt | MS |
|---|---|---|---|---|
| 215 | 1-((6-methoxy-1-methyl-1H-benzimidazol-7-yl)methyl)-3-(3-methylphenyl)urea | | | 325.2 |
| 216 | 1-(3-fluorophenyl)-3-((6-methoxy-1-methyl-1H-benzimidazol-7-yl)methyl)urea | | | 327 |

TABLE 1-37

| Example No. | IUPAC name | structural formula | salt | MS |
|---|---|---|---|---|
| 217 | 1-(4-fluoro-3-mehtylphenyl)-3-((6-methoxy-1-methyl-1H-benzimidazol-7-yl)methyl)urea | | | 343.2 |
| 218 | 1-(3-fluoro-4-methylphenyl)-3-((6-methoxy-1-methyl-1H-benzimidazol-7-yl)methyl)urea | | | 343.1 |
| 219 | 1-(3-chlorophenyl)-3-((6-methoxy-1-methyl-1H-benzimidazol-7-yl)methyl)urea | | | 345.1 |

TABLE 1-37-continued

| Example No. | IUPAC name | structural formula | salt | MS |
|---|---|---|---|---|
| 220 | 1-((6-methoxy-1-methyl-1H-benzimidazol-7-yl)methyl)-3-(3,4,5-trifluorophenyl)urea | | | 365.1 |
| 221 | 1-(4-(difluoromethoxy)phenyl)-3-((6-methoxy-1-methyl-1H-benzimidazol-7-yl)methyl)urea | | | 377.1 |
| 222 | 1-((6-methoxy-1-methyl-1H-benzimidazol-7-yl)methyl)-3-(3-(trifluoromethyl)phenyl)urea | | | 377.1 |

TABLE 1-38

| Example No. | IUPAC name | structural formula | salt | MS |
|---|---|---|---|---|
| 223 | 1-((6-methoxy-1-methyl-1H-benzimidazol-7-yl)methyl)-3-(4-(trifluoromethoxy)phenyl)urea | | | 395.1 |
| 224 | 1-(4-fluorophenyl)-3-((6-methoxy-1-methyl-1H-benzimidazol-7-yl)methyl)urea | | | 327.1 |

TABLE 1-38-continued

| Example No. | IUPAC name | structural formula | salt | MS |
|---|---|---|---|---|
| 225 | 1-(3-fluoro-4-methoxyphenyl)-3-((6-methoxy-1-methyl-1H-benzimidazol-7-yl)methyl)urea | | | 357.1 |
| 226 | N-((5-cyclopropyl-1H-benzotriazol-4-yl)methyl)-6-(difluoromethoxy)-5-fluoronicotinamide | | | 378.1 |
| 227 | 3-fluoro-N-((5-methoxy-1H-benzotriazol-4-yl)methyl)-4-(trifluoromethoxy)-benzamide | | | 385 |
| 228 | 5-chloro-N-((6-methoxy-1,2-dimethyl-1H-benzimidazol-7-yl)methyl)thiophene-3-carboxamide | | | 350.1 |

TABLE 1-39

| Example No. | IUPAC name | structural formula | salt | MS |
|---|---|---|---|---|
| 229 | 5-chloro-N-((6-methoxy-1,2-dimethyl-1H-benzimidazol-7-yl)methyl)thiophene-2-carboxamide | | | 350 |
| 230 | N-((6-methoxy-1,2-dimethyl-1H-benzimidazol-7-yl)methyl)-5-(trifluoromethyl)-thiophene-3-carboxamide | | | 384.1 |

TABLE 1-39-continued

| Example No. | IUPAC name | structural formula | salt | MS |
|---|---|---|---|---|
| 231 | N-((6-methoxy-1,2-dimethyl-1H-benzimidazol-7-yl)methyl)-5-(trifluoromethyl)-thiophene-2-carboxamide | | | 384.1 |
| 232 | 5-(difluoromethyl)-N-((6-methoxy-1,2-dimethyl-1H-benzimidazol-7-yl)methyl)thiophene-3-carboxamide | | | 366.1 |
| 233 | N-((6-methoxy-1,2-dimethyl-1H-benzimidazol-7-yl)methyl)-6-(trifluoromethoxy)-nicotinamide | | | 395.1 |
| 234 | 6-ethoxy-5-fluoro-N-((6-methoxy-1,2-dimethyl-1H-benzimidazol-7-yl)methyl)nicotinamide | | | 373.1 |

TABLE 1-40

| Example No. | IUPAC name | structural formula | salt | MS |
|---|---|---|---|---|
| 235 | 5-fluoro-6-methoxy-N-((6-methoxy-1,2-dimethyl-1H-benzimidazol-7-yl)methyl)nicotinamide | | | 359.1 |
| 236 | 3-fluoro-N-((6-methoxy-1,2-dimethyl-1H-benzimidazol-7-yl)methyl)-4-(trifluoromethyl)-benzamide | | | 396.1 |

TABLE 1-40-continued

| Example No. | IUPAC name | structural formula | salt | MS |
|---|---|---|---|---|
| 237 | N-((6-methoxy-1,2-dimethyl-1H-benzimidazol-7-yl)methyl)-4-(trifluoromethyl)benzamide | | | 378.1 |
| 238 | 3-fluoro-N-((6-methoxy-1,2-dimethyl-1H-benzimidazol-7-yl)methyl)-4-methylbenzamide | | | 342.1 |
| 239 | 3,5-difluoro-N-((6-methoxy-1,2-dimethyl-1H-benzimidazol-7-yl)methyl)-4-methylbenzamide | | | 360.1 |
| 240 | 4-(difluoromethyl)-3,5-difluoro-N-((6-methoxy-1,2-dimethyl-1H-benzimidazol-7-yl)methyl)benzamide | | | 396.1 |

TABLE 1-41

| Example No. | IUPAC name | structural formula | salt | MS |
|---|---|---|---|---|
| 241 | 4-(difluoromethyl)-N-((6-methoxy-1,2-dimethyl-1H-benzimidazol-7-yl)methyl)benzamide | | | 360.1 |

TABLE 1-41-continued

| Example No. | IUPAC name | structural formula | salt | MS |
|---|---|---|---|---|
| 242 | 4-(difluoromethyl)-3-fluoro-N-((6-methoxy-1,2-dimethyl-1H-benzimidazol-7-yl)methyl)benzamide | | | 378.1 |
| 243 | 3-fluoro-4-methoxy-N-((6-methoxy-1,2-dimethyl-1H-benzimidazol-7-yl)methyl)benzamide | | | 358.1 |
| 244 | 3-chloro-4-(difluoromethoxy)-N-((6-methoxy-1,2-dimethyl-1H-benzimidazol-7-yl)methyl)benzamide | | | 410 |
| 245 | 4-(difluoromethoxy)-N-((6-methoxy-1,2-dimethyl-1H-benzimidazol-7-yl)methyl)benzamide | | | 376.1 |
| 246 | 4-(difluoromethoxy)-3,5-difluoro-N-((6-methoxy-1,2-dimethyl-1H-benzimidazol-7-yl)methyl)benzamide | | | 412.1 |

TABLE 1-42

| Example No. | IUPAC name | structural formula | salt | MS |
|---|---|---|---|---|
| 247 | 3-chloro-4-fluoro-N-((6-methoxy-1,2-dimethyl-1H-benzimidazol-7-yl)methyl)benzamide | | | 362.1 |

TABLE 1-42-continued

| Example No. | IUPAC name | structural formula | salt | MS |
|---|---|---|---|---|
| 248 | 4-chloro-3-fluoro-N-((6-methoxy-1,2-dimethyl-1H-benzimidazol-7-yl)methyl)benzamide | | | 362 |
| 249 | 4-chloro-N-((6-methoxy-1,2-dimethyl-1H-benzimidazol-7-yl)methyl)benzamide | | | 344.1 |
| 250 | 3-chloro-4-(difluoromethyl)-N-((6-methoxy-1,2-dimethyl-1H-benzimidazol-7-yl)methyl)benzamide | | | 394.1 |
| 251 | 6-(difluoromethoxy)-5-fluoro-N-((6-methoxy-1,2-dimethyl-1H-benzimidazol-7-yl)methyl)nicotinamide | | | 395.1 |
| 252 | N-((6-methoxy-1,2-dimethyl-1H-benzimidazol-7-yl)methyl)-4-(trifluoromethoxy)-benzamide | | | 394.1 |

TABLE 1-43

| Example No. | IUPAC name | structural formula | salt | MS |
|---|---|---|---|---|
| 253 | 4-(difluoromethoxy)-3-fluoro-N-((6-methoxy-1,2-dimethyl-1H-benzimidazol-7-yl)methyl)benzamide | | | 394.1 |

TABLE 1-43-continued

| Example No. | IUPAC name | structural formula | salt | MS |
|---|---|---|---|---|
| 254 | 6-(difluoromethoxy)-N-((6-methoxy-1,2-dimethyl-1H-benzimidazol-7-yl)methyl)nicotinamide | 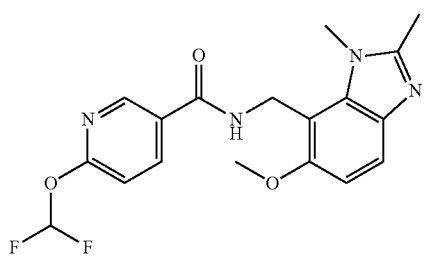 [SMILES: COc1ccc2nc(C)n(C)c2c1CNC(=O)c1ccc(OC(F)F)nc1] | | 377.1 |
| 255 | 1-((6-methoxy-1-methyl-1H-benzimidazol-7-yl)methyl)-3-phenylurea | 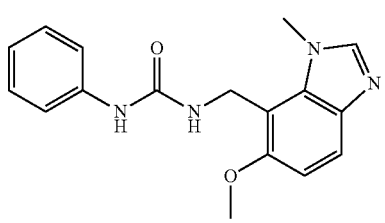 [SMILES: COc1ccc2ncn(C)c2c1CNC(=O)Nc1ccccc1] | | 311.2 |
| 256 | 1-((6-methoxy-1-methyl-1H-benzimidazol-7-yl)methyl)-3-(4-methylphenyl)urea | 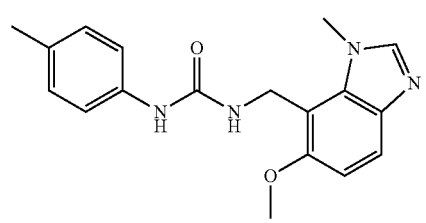 [SMILES: COc1ccc2ncn(C)c2c1CNC(=O)Nc1ccc(C)cc1] | | 325.2 |
| 257 | 1-(4-chlorophenyl)-3-((6-methoxy-1-methyl-1H-benzimidazol-7-yl)methyl)urea | 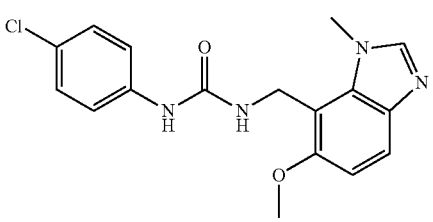 [SMILES: COc1ccc2ncn(C)c2c1CNC(=O)Nc1ccc(Cl)cc1] | | 343 |
| 258 | 1-(3,4-difluorophenyl)-3-((6-methoxy-1-methyl-1H-benzimidazol-7-yl)methyl)urea | 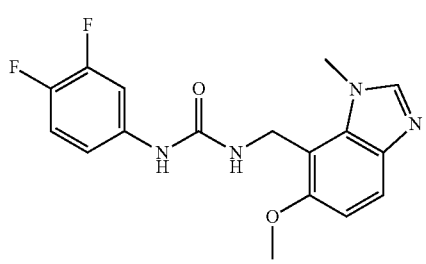 [SMILES: COc1ccc2ncn(C)c2c1CNC(=O)Nc1ccc(F)c(F)c1] | | 345 |

TABLE 1-44

| Example No. | IUPAC name | structural formula | salt | MS |
|---|---|---|---|---|
| 259 | 1-(2,3-difluoro-4-methoxyphenyl)-3-((6-methoxy-1-methyl-1H-benzimidazol-7-yl)methyl)urea | | | 377.1 |
| 260 | 1-(2-fluoro-4-(trifluoromethyl)-phenyl)-3-((6-methoxy-1-methyl-1H-benzimidazol-7-yl)methyl)urea | | | 397.1 |
| 261 | 1-(3-fluoro-4-(trifluoromethyl)-phenyl)-3-((6-methoxy-1-methyl-1H-benzimidazol-7-yl)methyl)urea | | | 395.1 |
| 262 | 1-((6-methoxy-1-methyl-1H-benzimidazol-7-yl)methyl)-3-(4-(trifluoromethyl)-phenyl)urea | | | 379.1 |
| 263 | 4-(difluoromethoxy)-3-fluoro-N-((5-methyl-1H-benzotriazol-4-yl)methyl)benzamide | | | 351.1 |
| 264 | 4-methoxy-N-((5-methyl-1H-benzotriazol-4-yl)methyl)benzamide | | | 297.1 |

TABLE 1-45

| Example No. | IUPAC name | structural formula | salt | MS |
|---|---|---|---|---|
| 265 | 4-(difluoromethoxy)-N-((5-methyl-1H-benzotriazol-4-yl)methyl)benzamide | 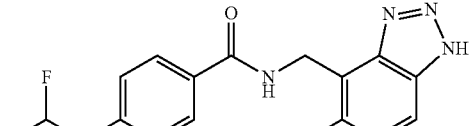 | | 333.1 |
| 266 | 1-((6-methoxy-1-methyl-1H-benzimidazol-7-yl)methyl)-3-(4-methoxyphenyl)urea | 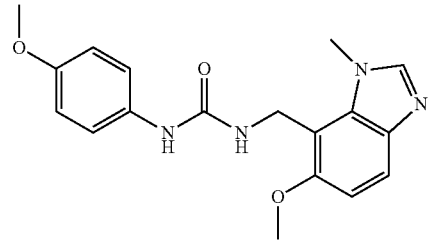 [SMILES: COc1ccc(NC(=O)NCc2c(OC)ccc3ncn(C)c23)cc1] | | 341.2 |
| 267 | 1-(4-fluoro-3-(trifluoromethyl)phenyl)-3-((6-methoxy-1-methyl-1H-benzimidazol-7-yl)methyl)urea | 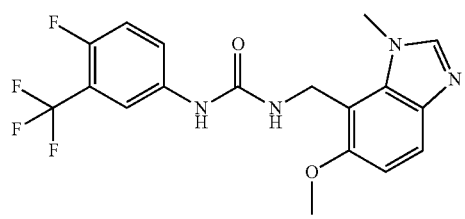 [SMILES: COc1ccc2ncn(C)c2c1CNC(=O)Nc1ccc(F)c(C(F)(F)F)c1] | | 395.1 |
| 268 | 6-(difluoromethoxy)-5-fluoro-N-((5-methyl-1H-benzotriazol-4-yl)methyl)nicotinamide | 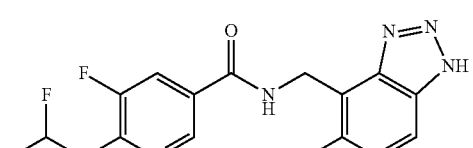 | | 352 |
| 269 | 3-fluoro-N-((3-methyl-1H-indazol-4-yl)methyl)-4-(trifluoromethoxy)benzamide | 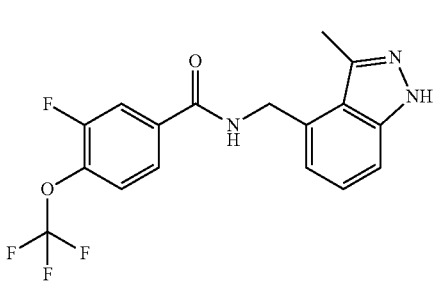 [SMILES: Cc1n[nH]c2cccc(CNC(=O)c3ccc(OC(F)(F)F)c(F)c3)c12] | | 368 |
| 270 | 3,5-difluoro-4-methoxy-N-((3-methyl-1H-indazol-4-yl)methyl)benzamide | 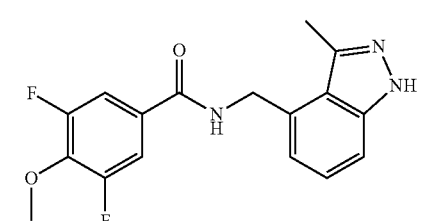 | | 332.2 |

TABLE 1-46

| Example No. | IUPAC name | structural formula | salt | MS |
|---|---|---|---|---|
| 271 | 6-(difluoromethoxy)-5-fluoro-N-((3-methyl-1H-indazol-4-yl)methyl)nicotinamide | | | 351.1 |
| 272 | N-[(3-bromo-1H-indazol-4-yl)methyl]-3-fluoro-4-(trifluoromethoxy)-benzamide | | | ND |
| 273 | N-[(5-fluoro-1H-indazol-4-yl)methyl]-4-(trifluoromethoxy)-benzamide | | | 353.9 |
| 274 | 3-fluoro-N-[(1-methyl-1H-benzotriazol-7-yl)methyl]-4-(trifluoromethoxy)-benzamide | | | 369.2 |
| 275 | 6-(difluoromethoxy)-5-fluoro-N-[(1-methyl-1H-benzotriazol-7-yl)methyl]pyridine-3-carboxamide | | | 350.0 |
| 276 | 6-(difluoromethoxy)-N-[(6-methoxy-1-methyl-1H-benzimidazol-7-yl)methyl]pyridine-3-carboxamide | | | 363.0 |

TABLE 1-47

| Example No. | IUPAC name | structural formula | salt | MS |
|---|---|---|---|---|
| 277 | 4-(difluoromethoxy)-2-fluoro-N-[(6-methoxy-1-methyl-1H-benzimidazol-7-yl)methyl]benzamide | | | 380.2 |
| 278 | N-[(6-methoxy-1-methyl-1H-benzimidazol-7-yl)methyl]-4-(2,2,2-trifluoroethyl)-benzamide | | | 378.0 |
| 279 | 3,5-difluoro-4-methoxy-N-{[6-(methoxymethyl)-1-methyl-1H-benzimidazol-7-yl]methyl}benzamide | | | 376.1 |
| 280 | N-{[6-(methoxymethyl)-1-methyl-1H-benzimidazol-7-yl]methyl}-4-(trifluoromethyl)-benzamide | | | 378.2 |
| 281 | 6-(difluoromethoxy)-5-fluoro-N-{[6-(methoxymethyl)-1-methyl-1H-benzimidazol-7-yl]methyl}pyridine-3-carboxamide | | | 395.2 |
| 282 | N-{[6-(methoxymethyl)-1-methyl-1H-benzimidazol-7-yl]methyl}-5-(trifluoromethyl)-thiophene-3-carboxamide | | | 384.1 |

TABLE 1-48

| Example No. | IUPAC name | structural formula | salt | MS |
|---|---|---|---|---|
| 283 | 3-chloro-4-(difluoromethoxy)-N-{[6-(methoxymethyl)-1-methyl-1H-benzimidazol-7-yl]methyl}benzamide | | | 410.1 |
| 284 | 3-fluoro-N-{[6-(methoxymethyl)-1-methyl-1H-benzimidazol-7-yl]methyl}-4-(trifluoromethoxy)-benzamide | | | 412.2 |

Experimental Example

NR2B Ca$^{2+}$ influx assay

To confirm the "antagonistic action on an NMDA receptor containing the NR2B subunit" of the compound of the present invention, human embryonic kidney cell expressing the "NMDA receptor composed of four subunits including 2 sets of heterodimers of NR1 and NR2B", specifically HEK293 cell expressing human glutamate ionotropic receptor NMDA type subunit 1 (GRIN1) and human glutamate ionotropic receptor NMDA type subunit 2B (GRIN2B), was used and the activation suppressive effect on the receptors was measured.

As an index of the NMDA receptor activation, intracellular calcium ion (Ca$^{2+}$) influx caused by the binding of glycine and glutamic acid with NR1 and NR2B, respectively, was used. HEK293 cells were purchased from ChanTest. The cells were cultured in a DMEM/F-12 (COSMO BIO, 10-092-CM) medium added with 10% FBS (fetal bovine serum, AusGene), 100 units/mL penicillin, 100 μg/mL streptomycin, 500 μg/mL neomycin, 100 μg/mL Zeocin, 5 μg/mL Blasticidin at 37° C., 5% CO$_2$. The cells were detached from flask with trypsin the day before the assay, suspended in a seeding medium (DMEM (Invitrogen, 31053) added with 10% FBS, 100 units/mL penicillin, 100 μg/mL streptomycin) at 8×10$^5$ cells/mL, seeded by 25 μL per well in a 384-well plate (Falcon, 356663) at 20000 cells/well, and cultured overnight in an incubator. On the day of the assay, tetracycline (Wako Pure Chemical Industries, Ltd., 209-16561) was diluted with the seeding medium at 2 μg/mL, added at 25 μg/mL to the plate seeded with the cells, and cultured for 2 hr in an incubator. Thereafter, the medium was removed, and the cells were washed with 50 μL/well assay buffer (137 mM NaCl, 4 mM KCl, 1.8 mM CaCl$_2$, 10 mM HEPES (pH 7.2), 10 mM Glucose, 0.1% BSA). Then, a loading buffer (assay buffer added with 2.5 uM Fluo-4AM, 2 mM Amaranth, 1 mM Tartrazine) was added at 25 μL/well, and loading was performed in the incubator for 30 min, and at room temperature for 15 min. A solution (25 μL) of the Example compound diluted with the above-mentioned assay buffer at 30 μM (final concentration 10 μM) was added, and the cells were stood for 15 min at room temperature. Using FLIPR (Molecular Devices), 25 μL of an assay buffer containing 30 μM glutamic acid, 30 μM glycine was added, and the fluorescence signal was measured every 3 seconds for 5 min. The inhibitory activity was calculated as a relative activity value (inhibitory rate) that inhibits 100% of the cumulative value of the fluorescence value of a well added with a buffer free of glutamic acid, glycine, relative to the cumulative value of the fluorescence value of each well. The results are shown in Tables 2-1 to -5.

TABLE 2-1

| Ex. No. | inhibitory rate (10 μM compound concentration) |
|---|---|
| 1 | 82 |
| 2 | 92 |
| 3 | 97 |
| 4 | 87 |
| 5 | 85 |
| 6 | 91 |
| 7 | 93 |
| 8 | 92 |
| 9 | 92 |
| 10 | 92 |
| 11 | 92 |
| 12 | 94 |
| 13 | 94 |
| 14 | 92 |
| 15 | 95 |
| 16 | 94 |
| 17 | 93 |
| 18 | 87 |
| 19 | 83 |
| 20 | 90 |
| 21 | 91 |
| 22 | 90 |
| 23 | 93 |
| 24 | 90 |
| 25 | 92 |
| 26 | 66 |
| 27 | 82 |
| 28 | 90 |
| 29 | 91 |
| 30 | 90 |
| 31 | 91 |
| 32 | 77 |

TABLE 2-1-continued

| Ex. No. | inhibitory rate (10 μM compound concentration) |
|---|---|
| 33 | 86 |
| 34 | 89 |
| 35 | 77 |
| 36 | 89 |
| 37 | 91 |
| 38 | 91 |
| 39 | 91 |
| 40 | 89 |
| 41 | 90 |
| 137 | 72 |
| 138 | 88 |
| 139 | 91 |
| 140 | 90 |
| 141 | 90 |
| 142 | 85 |
| 143 | 91 |
| 144 | 90 |
| 145 | 92 |
| 146 | 90 |
| 147 | 92 |
| 148 | 91 |
| 149 | 93 |
| 150 | 60 |
| 151 | 83 |
| 152 | 91 |
| 153 | 90 |
| 154 | 91 |
| 155 | 92 |
| 156 | 76 |
| 157 | 85 |
| 158 | 89 |
| 159 | 86 |
| 160 | 65 |
| 161 | 92 |
| 162 | 92 |
| 163 | 89 |
| 164 | 92 |
| 165 | 91 |
| 166 | 56 |
| 167 | 58 |
| 168 | 90 |
| 169 | 70 |
| 170 | 76 |
| 171 | 85 |
| 172 | 60 |
| 173 | 80 |
| 174 | 80 |
| 175 | 82 |
| 176 | 51 |
| 177 | 52 |

TABLE 2-2

| Ex. No. | inhibitory rate (10 μM compound concentration) |
|---|---|
| 42 | 87 |
| 43 | 61 |
| 44 | 89 |
| 45 | 64 |
| 46 | 68 |
| 47 | 85 |
| 48 | 84 |
| 49 | 69 |
| 50 | 89 |
| 51 | 90 |
| 52 | 91 |
| 53 | 91 |
| 54 | 85 |
| 55 | 90 |
| 56 | 93 |
| 57 | 91 |
| 58 | 93 |
| 59 | 94 |

TABLE 2-2-continued

| Ex. No. | inhibitory rate (10 μM compound concentration) |
|---|---|
| 60 | 94 |
| 61 | 94 |
| 62 | 94 |
| 63 | 89 |
| 64 | 91 |
| 65 | 90 |
| 66 | 91 |
| 67 | 92 |
| 68 | 86 |
| 69 | 93 |
| 70 | 92 |
| 71 | 92 |
| 72 | 89 |
| 73 | 94 |
| 74 | 93 |
| 75 | 92 |
| 76 | 93 |
| 77 | 92 |
| 78 | 93 |
| 79 | 92 |
| 80 | 93 |
| 81 | 82 |
| 82 | 94 |
| 178 | 70 |
| 179 | 96 |
| 180 | 89 |
| 181 | 67 |
| 182 | 97 |
| 183 | 87 |
| 184 | 93 |
| 185 | 74 |
| 186 | 56 |
| 187 | 74 |
| 188 | 52 |
| 189 | 67 |
| 190 | 86 |
| 191 | 94 |
| 192 | 94 |
| 193 | 86 |
| 194 | 97 |
| 195 | 91 |
| 196 | 78 |
| 197 | 96 |
| 198 | 90 |
| 199 | 92 |
| 200 | 85 |
| 201 | 92 |
| 202 | 83 |
| 203 | 93 |
| 204 | 93 |
| 205 | 87 |
| 206 | 95 |
| 207 | 98 |
| 208 | 85 |
| 209 | 94 |
| 210 | 90 |
| 211 | 95 |
| 212 | 93 |
| 213 | 98 |
| 214 | 86 |
| 215 | 53 |
| 216 | 78 |
| 217 | 82 |
| 218 | 93 |

TABLE 2-3

| Ex. No. | inhibitory rate (10 μM compound concentration) |
|---|---|
| 83 | 93 |
| 84 | 91 |
| 85 | 93 |
| 86 | 94 |

TABLE 2-3-continued

| Ex. No. | inhibitory rate (10 μM compound concentration) |
|---|---|
| 87 | 94 |
| 88 | 93 |
| 89 | 91 |
| 90 | 94 |
| 91 | 94 |
| 92 | 93 |
| 93 | 94 |
| 94 | 93 |
| 95 | 95 |
| 96 | 93 |
| 97 | 94 |
| 98 | 90 |
| 99 | 91 |
| 100 | 91 |
| 101 | 92 |
| 102 | 92 |
| 103 | 93 |
| 104 | 90 |
| 105 | 93 |
| 106 | 93 |
| 107 | 93 |
| 108 | 94 |
| 109 | 92 |
| 110 | 92 |
| 111 | 93 |
| 112 | 92 |
| 113 | 90 |
| 114 | 87 |
| 115 | 93 |
| 116 | 90 |
| 117 | 90 |
| 118 | 94 |
| 119 | 94 |
| 120 | 92 |
| 121 | 91 |
| 122 | 90 |
| 123 | 88 |
| 219 | 72 |
| 220 | 87 |
| 221 | 88 |
| 222 | 55 |
| 223 | 83 |
| 224 | 81 |
| 225 | 84 |
| 226 | 94 |
| 227 | 97 |
| 228 | 70 |
| 229 | 62 |
| 230 | 82 |
| 231 | 73 |
| 232 | 64 |
| 233 | 72 |
| 234 | 73 |
| 235 | 57 |
| 236 | 59 |
| 237 | 68 |
| 238 | 61 |
| 239 | 60 |
| 240 | 53 |
| 241 | 70 |
| 242 | 69 |
| 243 | 69 |
| 244 | 87 |
| 245 | 81 |
| 246 | 87 |
| 247 | 71 |
| 248 | 64 |
| 249 | 57 |
| 250 | 58 |
| 251 | 76 |
| 252 | 88 |
| 253 | 84 |
| 254 | 69 |
| 255 | 67 |
| 256 | 90 |
| 257 | 90 |
| 258 | 85 |
| 259 | 87 |

TABLE 2-4

| Ex. No. | inhibitory rate (10 μM compound concentration) |
|---|---|
| 124 | 90 |
| 125 | 92 |
| 126 | 88 |
| 127 | 92 |
| 128 | 91 |
| 129 | 88 |
| 130 | 91 |
| 131 | 93 |
| 132 | 90 |
| 133 | 91 |
| 134 | 90 |
| 135 | 90 |
| 136 | 83 |
| 260 | 92 |
| 261 | 92 |
| 262 | 91 |
| 263 | 98 |
| 264 | 83 |
| 265 | 97 |
| 266 | 58 |
| 267 | 74 |
| 268 | 97 |
| 269 | 87 |
| 270 | 67 |
| 271 | 82 |

TABLE 2-5

| Ex. No. | inhibitory rate (10 μM compound concentration) |
|---|---|
| 272 | 59 |
| 273 | 93 |
| 274 | 93 |
| 275 | 82 |
| 276 | 88 |
| 277 | 63 |
| 278 | 77 |
| 279 | 88 |
| 280 | 75 |
| 281 | 82 |
| 282 | 76 |
| 283 | 93 |
| 284 | 95 |

As shown in the above-mentioned Tables 2-1 to 5, the compound of the present invention suppressed intracellular calcium ion ($Ca^{2+}$) influx in the NMDA receptors containing the NR2B subunit. That is, it has been confirmed that the compound of the present invention has an antagonistic action on an NMDA receptor containing the NR2B subunit.

Formulation Example 1 (Production of Capsule)

1) compound of Example 1 30 mg
2) finely-powdered cellulose 10 mg
3) lactose 19 mg
4) magnesium stearate 1 mg
  total 60 mg 1), 2), 3) and 4) are mixed and filled in a gelatin capsule.

Formulation Example 2 (Production of Tablets)

1) compound of Example 1 30 g
2) lactose 50 g
3) cornstarch 15 g
4) calcium carboxymethylcellulose 44 g
5) magnesium stearate 1 g
   1000 tablets total 140 g The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention can have an antagonistic action on an NMDA receptor containing the NR2B subunit, and is expected to be useful as a prophylactic or therapeutic agent for major depression, bipolar disorder, migraine, pain, peripheral symptoms of dementia and the like.

This application is based on a patent application No. 2017-146744 filed in Japan (filing date: Jul. 28, 2017), the contents of which are incorporated in full herein.

The invention claimed is:
1. A method for antagonizing an NMDA receptor containing an NR2B subunit in a mammal, comprising administering to the mammal an effective amount of a compound chosen from:
   N-((2,5-dimethyl-2H-indazol-4-yl)methyl)-4-(trifluoromethoxy)benzamide;
   N-((5-methyl-1H-indazol-4-yl)methyl)-4-(trifluoromethoxy)benzamide;
   N-((5-methyl-1H-benzimidazol-4-yl)methyl)-4-(trifluoromethoxy)benzamide;
   N-((5-iodo-1H-indazol-4-yl)methyl)-4-(trifluoromethoxy)benzamide;
   4-(trifluoromethoxy)-N-((5-(trifluoromethyl)-1H-indazol-4-yl)methyl)benzamide;
   N-((5-methoxy-1H-indazol-4-yl)methyl)-4-(trifluoromethoxy)benzamide;
   N-(1H-indazol-4-ylmethyl)-4-(trifluoromethoxy)benzamide;
   3,5-difluoro-4-methoxy-N-((6-methoxy-1-methyl-1H-benzimidazol-7-yl)methyl)benzamide;
   3,5-difluoro-N-((6-methoxy-1-methyl-1H-benzimidazol-7-yl)methyl)-4-methylbenzamide;
   5-fluoro-6-methoxy-N-((6-methoxy-1-methyl-1H-benzimidazol-7-yl)methyl)nicotinamide;
   3-fluoro-4-methoxy-N-((6-methoxy-1-methyl-1H-benzimidazol-7-yl)methyl)benzamide;
   N-((6-methoxy-1-methyl-1H-benzimidazol-7-yl)methyl)-4-(trifluoromethoxy)benzamide;
   3-fluoro-N-((6-methoxy-1-methyl-1H-benzimidazol-7-yl)methyl)-4-(trifluoromethyl)benzamide;
   3-fluoro-N-((6-methoxy-1-methyl-1H-benzimidazol-7-yl)methyl)-4-methylbenzamide;
   4-chloro-3,5-difluoro-N-((6-methoxy-1-methyl-1H-benzimidazol-7-yl)methyl)benzamide;
   N-((5-ethyl-1H-indazol-4-yl)methyl)-3,5-difluoro-4-methoxybenzamide;
   N-((5-cyclopropyl-1H-indazol-4-yl)methyl)-3,5-difluoro-4-methoxybenzamide;
   3-chloro-4,5-difluoro-N-((6-methoxy-1-methyl-1H-benzimidazol-7-yl)methyl)benzamide;
   N-((1,6-dimethyl-1H-benzimidazol-7-yl)methyl)-5-fluoro-6-methoxynicotinamide;
   N-((6-cyclopropyl-1-methyl-1H-benzimidazol-7-yl)methyl)-5-fluoro-6-methoxynicotinamide;
   N-((6-cyclopropyl-1-methyl-1H-benzimidazol-7-yl)methyl)-3,5-difluoro-4-methoxybenzamide;
   N-((6-ethyl-1-methyl-1H-benzimidazol-7-yl)methyl)-5-fluoro-6-methoxynicotinamide;
   N-((6-ethyl-1-methyl-1H-benzimidazol-7-yl)methyl)-3,5-difluoro-4-methoxybenzamide;
   3,5-difluoro-N-((6-methoxy-1-methyl-1H-benzimidazol-7-yl)methyl)-4-(trifluoromethyl)benzamide;
   N-((1,6-dimethyl-1H-benzimidazol-7-yl)methyl)-3,5-difluoro-4-methoxybenzamide;
   N-((1,6-dimethyl-1H-benzimidazol-7-yl)methyl)-3,5-difluoro-4-(trifluoromethyl)benzamide;
   N-((6-methoxy-1-methyl-1H-benzimidazol-7-yl)methyl)-5-methylthiophene-3-carboxamide;
   5-chloro-N-((6-methoxy-1-methyl-1H-benzimidazol-7-yl)methyl)thiophene-3-carboxamide;
   5-ethyl-N-((6-methoxy-1-methyl-1H-benzimidazol-7-yl)methyl)thiophene-3-carboxamide;
   N-((1,6-dimethyl-1H-benzimidazol-7-yl)methyl)-3-fluoro-4-(trifluoromethoxy)benzamide;
   3-chloro-4-(difluoromethoxy)-N-((1,6-dimethyl-1H-benzimidazol-7-yl)methyl)benzamide;
   N-((6-methoxy-1-methyl-1H-benzimidazol-7-yl)methyl)-5-methylthiophene-2-carboxamide;
   N-((6-methoxy-1-methyl-1H-benzimidazol-7-yl)methyl)-2-(2-thienyl)acetamide;
   3-chloro-4-methoxy-N-((6-methoxy-1-methyl-1H-benzimidazol-7-yl)methyl)benzamide;
   4-methoxy-N-((6-methoxy-1-methyl-1H-benzimidazol-7-yl)methyl)-3,5-dimethylbenzamide;
   5-chloro-N-((6-methoxy-1-methyl-1H-benzimidazol-7-yl)methyl)thiophene-2-carboxamide;
   3-chloro-4-fluoro-N-((6-methoxy-1-methyl-1H-benzimidazol-7-yl)methyl)benzamide;
   3-chloro-N-((6-methoxy-1-methyl-1H-benzimidazol-7-yl)methyl)-4-methylbenzamide;
   4-chloro-N-((6-methoxy-1-methyl-1H-benzimidazol-7-yl)methyl)-3-methylbenzamide;
   4-fluoro-N-((6-methoxy-1-methyl-1H-benzimidazol-7-yl)methyl)-3-(trifluoromethyl)benzamide;
   3,4,5-trifluoro-N-((6-methoxy-1-methyl-1H-benzimidazol-7-yl)methyl)benzamide;
   4-chloro-N-((6-methoxy-1-methyl-1H-benzimidazol-7-yl)methyl)thiophene-2-carboxamide;
   N-((6-methoxy-1-methyl-1H-benzimidazol-7-yl)methyl)-4-methylthiophene-2-carboxamide;
   4-chloro-3-fluoro-N-((6-methoxy-1-methyl-1H-benzimidazol-7-yl)methyl)benzamide;
   4-chloro-3-methoxy-N-((6-methoxy-1-methyl-1H-benzimidazol-7-yl)methyl)benzamide;
   4-fluoro-3-methoxy-N-((6-methoxy-1-methyl-1H-benzimidazol-7-yl)methyl)benzamide;
   N-((6-methoxy-1-methyl-1H-benzimidazol-7-yl)methyl)-4-methyl-3-(trifluoromethyl)benzamide;
   5-methoxy-N-((6-methoxy-1-methyl-1H-benzimidazol-7-yl)methyl)thiophene-2-carboxamide;
   3,5-dichloro-4-fluoro-N-((6-methoxy-1-methyl-1H-benzimidazol-7-yl)methyl)benzamide;
   N-((6-methoxy-1-methyl-1H-benzimidazol-7-yl)methyl)-5-(trifluoromethyl)thiophene-2-carboxamide;
   3-chloro-N-((6-methoxy-1-methyl-1H-benzimidazol-7-yl)methyl)-4-(trifluoromethyl)benzamide;

3-fluoro-N-((6-methoxy-1-methyl-1H-benzimidazol-7-yl)methyl)-4-(trifluoromethoxy)benzamide;
4,5-dichloro-N-((6-methoxy-1-methyl-1H-benzimidazol-7-yl)methyl)thiophene-2-carboxamide;
3,4-difluoro-N-((6-methoxy-1-methyl-1H-benzimidazol-7-yl)methyl)-5-methylbenzamide;
3,4-dichloro-5-fluoro-N-((6-methoxy-1-methyl-1H-benzimidazol-7-yl)methyl)benzamide;
N-((6-methoxy-1-methyl-1H-benzimidazol-7-yl)methyl)-6-(trifluoromethoxy)-nicotinamide;
5-chloro-6-methoxy-N-((6-methoxy-1-methyl-1H-benzimidazol-7-yl)methyl)nicotinamide;
5-chloro-6-ethoxy-N-((6-methoxy-1-methyl-1H-benzimidazol-7-yl)methyl)nicotinamide;
6-(difluoromethoxy)-5-fluoro-N-((6-methoxy-1-methyl-1H-benzimidazol-7-yl)methyl)nicotinamide;
3-chloro-N-((1,6-dimethyl-1H-benzimidazol-7-yl)methyl)-4-(trifluoromethoxy)-benzamide;
N-((5-cyclopropyl-1H-indazol-4-yl)methyl)-4-(trifluoromethyl)benzamide;
N-((5-cyclopropyl-1H-indazol-4-yl)methyl)-4-(trifluoromethoxy)benzamide;
N-((5-cyclopropyl-1H-indazol-4-yl)methyl)-4-methylthiophene-2-carboxamide;
N-((5-cyclopropyl-1H-indazol-4-yl)methyl)-5-methylthiophene-2-carboxamide;
N-((5-cyclopropyl-1H-indazol-4-yl)methyl)-2-(2-thienyl)acetamide;
N-((5-cyclopropyl-1H-indazol-4-yl)methyl)-5-methylthiophene-3-carboxamide;
N-((5-cyclopropyl-1H-indazol-4-yl)methyl)-5-methoxythiophene-2-carboxamide;
N-((5-cyclopropyl-1H-indazol-4-yl)methyl)-4-methoxythiophene-2-carboxamide;
5-chloro-N-((5-cyclopropyl-1H-indazol-4-yl)methyl)thiophene-3-carboxamide;
4-chloro-N-((5-cyclopropyl-1H-indazol-4-yl)methyl)thiophene-2-carboxamide;
5-chloro-N-((5-cyclopropyl-1H-indazol-4-yl)methyl)thiophene-2-carboxamide;
N-((5-cyclopropyl-1H-indazol-4-yl)methyl)-4-fluoro-3-methoxybenzamide;
4-chloro-N-((5-cyclopropyl-1H-indazol-4-yl)methyl)-3-methylbenzamide;
3-chloro-N-((5-cyclopropyl-1H-indazol-4-yl)methyl)-4-methylbenzamide;
N-((5-cyclopropyl-1H-indazol-4-yl)methyl)-4-fluoro-3-methylbenzamide;
N-((5-cyclopropyl-1H-indazol-4-yl)methyl)-3,4-difluoro-5-methylbenzamide;
3-chloro-N-((5-cyclopropyl-1H-indazol-4-yl)methyl)-4-fluorobenzamide;
4-chloro-N-((5-cyclopropyl-1H-indazol-4-yl)methyl)-3-fluorobenzamide;
N-((5-cyclopropyl-1H-indazol-4-yl)methyl)-3,4,5-trifluorobenzamide;
3-chloro-N-((5-cyclopropyl-1H-indazol-4-yl)methyl)-4-methoxybenzamide;
4-chloro-N-((5-cyclopropyl-1H-indazol-4-yl)methyl)-3-methoxybenzamide;
N-((5-cyclopropyl-1H-indazol-4-yl)methyl)-5-(trifluoromethyl)thiophene-2-carboxamide;
4,5-dichloro-N-((5-cyclopropyl-1H-indazol-4-yl)methyl)thiophene-2-carboxamide;
N-((5-cyclopropyl-1H-indazol-4-yl)methyl)-4-methyl-3-(trifluoromethyl)benzamide;
N-((5-cyclopropyl-1H-indazol-4-yl)methyl)-4-fluoro-3-(trifluoromethyl)benzamide;
3,5-dichloro-N-((5-cyclopropyl-1H-indazol-4-yl)methyl)-4-fluorobenzamide;
3,4-dichloro-N-((5-cyclopropyl-1H-indazol-4-yl)methyl)-5-fluorobenzamide;
N-((5-cyclopropyl-1H-indazol-4-yl)methyl)-3-fluoro-4-(trifluoromethoxy)benzamide;
3-chloro-N-((5-cyclopropyl-1H-indazol-4-yl)methyl)-4-(trifluoromethyl)benzamide;
4-chloro-N-((5-cyclopropyl-1H-indazol-4-yl)methyl)-3,5-difluorobenzamide;
N-((5-cyclopropyl-1H-indazol-4-yl)methyl)-3,5-difluoro-4-(trifluoromethyl)benzamide;
N-((5-cyclopropyl-1H-indazol-4-yl)methyl)-3-fluoro-4-(trifluoromethyl)benzamide;
N-((5-cyclopropyl-1H-indazol-4-yl)methyl)-3-fluoro-4-methylbenzamide;
N-((5-cyclopropyl-1H-indazol-4-yl)methyl)-3-fluoro-4-methoxybenzamide;
3-chloro-N-((5-cyclopropyl-1H-indazol-4-yl)methyl)-4,5-difluorobenzamide;
N-((5-cyclopropyl-1H-indazol-4-yl)methyl)-5-fluoro-6-methoxynicotinamide;
N-((5-cyclopropyl-1H-indazol-4-yl)methyl)-3,5-difluoro-4-methylbenzamide;
N-((5-cyclopropyl-1H-indazol-4-yl)methyl)-4-(difluoromethyl)benzamide;
N-((5-cyclopropyl-1H-indazol-4-yl)methyl)-4-methylbenzamide;
N-((5-cyclopropyl-1H-indazol-4-yl)methyl)-4-(difluoromethoxy)benzamide;
N-((5-cyclopropyl-1H-indazol-4-yl)methyl)-4-methoxybenzamide;
4-chloro-N-((5-cyclopropyl-1H-indazol-4-yl)methyl)benzamide;
5-chloro-N-((5-cyclopropyl-1H-indazol-4-yl)methyl)-6-methoxynicotinamide;
5-chloro-N-((5-cyclopropyl-1H-indazol-4-yl)methyl)-6-ethoxynicotinamide;
N-((5-cyclopropyl-1H-indazol-4-yl)methyl)-6-(difluoromethoxy)-5-fluoronicotinamide;
N-((5-cyclopropyl-1H-indazol-4-yl)methyl)-6-(trifluoromethoxy)-nicotinamide;
3-chloro-N-((5-cyclopropyl-1H-indazol-4-yl)methyl)-4-(difluoromethoxy)-benzamide;
N-((5-cyclopropyl-1H-indazol-4-yl)methyl)-4-(difluoromethyl)-3,5-difluorobenzamide;
4-(difluoromethoxy)-N-((1,6-dimethyl-1H-benzimidazol-7-yl)methyl)-3-fluorobenzamide;
5-(difluoromethyl)-N-((6-methoxy-1-methyl-1H-benzimidazol-7-yl)methyl)thiophene-3-carboxamide;
3-chloro-5-fluoro-4-methoxy-N-((6-methoxy-1-methyl-1H-benzimidazol-7-yl)methyl)benzamide;
3-chloro-4-(difluoromethyl)-N-((6-methoxy-1-methyl-1H-benzimidazol-7-yl)methyl)benzamide;
5-chloro-N-((6-methoxy-1-methyl-1H-benzimidazol-7-yl)methyl)-6-(trifluoromethyl)-nicotinamide;
N-((6-methoxy-1-methyl-1H-benzimidazol-7-yl)methyl)-4-methylbenzamide;
5-cyclopropyl-N-((6-methoxy-1-methyl-1H-benzimidazol-7-yl)methyl)thiophene-3-carboxamide;
4-chloro-N-((6-methoxy-1-methyl-1H-benzimidazol-7-yl)methyl)benzamide;
N-((6-methoxy-1-methyl-1H-benzimidazol-7-yl)methyl)-4-(trifluoromethyl)benzamide;

N-((5-cyclopropyl-1H-indazol-4-yl)methyl)-4-(difluoromethyl)-3-fluorobenzamide;
N-((5-cyclopropyl-1H-indazol-4-yl)methyl)-6-ethoxy-5-fluoronicotinamide;
N-((5-cyclopropyl-1H-indazol-4-yl)methyl)-4-(difluoromethoxy)-3-fluorobenzamide;
5-chloro-N-((5-cyclopropyl-1H-indazol-4-yl)methyl)-6-(difluoromethoxy)-nicotinamide;
5-ethyl-N-((6-methoxy-1-methyl-1H-benzimidazol-7-yl)methyl)thiophene-2-carboxamide;
4-(difluoromethyl)-N-((6-methoxy-1-methyl-1H-benzimidazol-7-yl)methyl)benzamide;
4-(difluoromethyl)-3-fluoro-N-((6-methoxy-1-methyl-1H-benzimidazol-7-yl)methyl)benzamide;
5-(difluoromethyl)-N-((6-ethoxy-1-methyl-1H-benzimidazol-7-yl)methyl)thiophene-3-carboxamide;
5-(difluoromethyl)-N-((6-ethoxy-1-methyl-1H-benzimidazol-7-yl)methyl)thiophene-2-carboxamide;
N-((6-ethoxy-1-methyl-1H-benzimidazol-7-yl)methyl)-3,5-difluoro-4-methoxybenzamide;
N-((6-ethoxy-1-methyl-1H-benzimidazol-7-yl)methyl)-4-(trifluoromethyl)-benzamide;
N-((1,6-dimethyl-1H-benzimidazol-7-yl)methyl)-3-fluoro-4-methoxybenzamide;
N-((6-ethyl-1-methyl-1H-benzimidazol-7-yl)methyl)-3-fluoro-4-methoxybenzamide;
4-(difluoromethoxy)-N-((6-ethyl-1-methyl-1H-benzimidazol-7-yl)methyl)-3,5-difluorobenzamide;
5-(difluoromethyl)-N-((6-ethyl-1-methyl-1H-benzimidazol-7-yl)methyl)thiophene-3-carboxamide;
4-(difluoromethyl)-N-((6-ethyl-1-methyl-1H-benzimidazol-7-yl)methyl)benzamide;
6-(difluoromethoxy)-N-((1,6-dimethyl-1H-benzimidazol-7-yl)methyl)-5-fluoronicotinamide;
4-(difluoromethoxy)-N-((1,6-dimethyl-1H-benzimidazol-7-yl)methyl)benzamide;
4-(difluoromethyl)-N-((1,6-dimethyl-1H-benzimidazol-7-yl)methyl)-3-fluorobenzamide;
5-(difluoromethyl)-N-((1,6-dimethyl-1H-benzimidazol-7-yl)methyl)thiophene-2-carboxamide;
N-((1,6-dimethyl-1H-benzimidazol-7-yl)methyl)-6-(trifluoromethoxy)-nicotinamide;
N-((6-methoxy-1-methyl-1H-benzimidazol-7-yl)methyl)-5-(trifluoromethyl)-thiophene-3-carboxamide;
4-(difluoromethyl)-N-((6-ethoxy-1-methyl-1H-benzimidazol-7-yl)methyl)benzamide;
4-(difluoromethyl)-N-((6-ethoxy-1-methyl-1H-benzimidazol-7-yl)methyl)-3-fluorobenzamide;
5-(difluoromethyl)-N-((1,6-dimethyl-1H-benzimidazol-7-yl)methyl)thiophene-3-carboxamide;
6-(difluoromethoxy)-N-((6-ethyl-1-methyl-1H-benzimidazol-7-yl)methyl)-5-fluoronicotinamide;
5-cyclopropyl-N-((1,6-dimethyl-1H-benzimidazol-7-yl)methyl)thiophene-3-carboxamide;
N-((6-ethyl-1-methyl-1H-benzimidazol-7-yl)methyl)-4-methoxybenzamide;
4-(difluoromethyl)-N-((6-ethyl-1-methyl-1H-benzimidazol-7-yl)methyl)-3-fluorobenzamide;
5-chloro-N-((6-ethyl-1-methyl-1H-benzimidazol-7-yl)methyl)thiophene-3-carboxamide;
4-(difluoromethoxy)-N-((6-ethyl-1-methyl-1H-benzimidazol-7-yl)methyl)benzamide;
N-((6-ethyl-1-methyl-1H-benzimidazol-7-yl)methyl)-6-(trifluoromethoxy)-nicotinamide;
N-((1-ethyl-6-methoxy-1H-benzimidazol-7-yl)methyl)-5-fluoro-6-methoxynicotinamide;
N-((1-ethyl-6-methoxy-1H-benzimidazol-7-yl)methyl)-3,5-difluoro-4-methoxybenzamide;
N-((1,6-dimethyl-1H-benzimidazol-7-yl)methyl)-4-(trifluoromethoxy)-benzamide;
N-((5-cyclopropyl-1H-indazol-4-yl)methyl)-4-(difluoromethoxy)-3,5-difluorobenzamide;
N-((5-cyclopropyl-1H-indazol-4-yl)methyl)-5-(difluoromethyl)-thiophene-3-carboxamide;
N-((5-cyclopropyl-1H-indazol-4-yl)methyl)-5-(difluoromethyl)-thiophene-2-carboxamide;
5-chloro-N-((1,6-dimethyl-1H-benzimidazol-7-yl)methyl)thiophene-3-carboxamide;
4-(difluoromethyl)-N-((1,6-dimethyl-1H-benzimidazol-7-yl)methyl)benzamide;
4-(difluoromethoxy)-N-((1,6-dimethyl-1H-benzimidazol-7-yl)methyl)-3,5-difluorobenzamide;
6-(difluoromethoxy)-N-((1,6-dimethyl-1H-benzimidazol-7-yl)methyl)nicotinamide;
3,5-difluoro-4-methoxy-N-((1-methyl-1H-benzimidazol-7-yl)methyl)benzamide;
4-(difluoromethoxy)-3,5-difluoro-N-((6-methoxy-1-methyl-1H-benzimidazol-7-yl)methyl)benzamide;
N-((6-methoxy-1-methyl-1H-benzimidazol-7-yl)methyl)-5-(trifluoromethyl)-thiophene-2-carboxamide hydrochloride;
N-((1,6-dimethyl-1H-benzimidazol-7-yl)methyl)-5-(trifluoromethyl)-thiophene-3-carboxamide;
6-(difluoromethoxy)-N-((6-ethyl-1-methyl-1H-benzimidazol-7-yl)methyl)nicotinamide;
N-((5-cyclopropyl-1H-benzotriazol-4-yl)methyl)-5-fluoro-6-methoxynicotinamide;
5-chloro-N-(1H-indazol-4-ylmethyl)thiophene-3-carboxamide;
N-(1H-indazol-4-ylmethyl)-5-(trifluoromethyl)-thiophene-2-carboxamide;
4,5-dichloro-N-(1H-indazol-4-ylmethyl)thiophene-2-carboxamide;
5-chloro-N-(1H-indazol-4-ylmethyl)-6-methoxynicotinamide;
N-(1H-indazol-4-ylmethyl)-6-(trifluoromethoxy)-nicotinamide;
6-ethoxy-5-fluoro-N-(1H-indazol-4-ylmethyl)nicotinamide;
5-fluoro-N-(1H-indazol-4-ylmethyl)-6-methoxynicotinamide;
3,5-difluoro-N-(1H-indazol-4-ylmethyl)-4-(trifluoromethyl)-benzamide;
3-fluoro-N-(1H-indazol-4-ylmethyl)-4-(trifluoromethyl)-benzamide;
N-(1H-indazol-4-ylmethyl)-4-(trifluoromethyl)-benzamide;
3-fluoro-N-(1H-indazol-4-ylmethyl)-4-methylbenzamide;
4-(difluoromethyl)-N-(1H-indazol-4-ylmethyl)benzamide;
4-(difluoromethyl)-3-fluoro-N-(1H-indazol-4-ylmethyl)benzamide;
3-fluoro-N-(1H-indazol-4-ylmethyl)-4-(trifluoromethoxy)-benzamide;
3,5-difluoro-N-(1H-indazol-4-ylmethyl)-4-methoxybenzamide;
3-fluoro-N-(1H-indazol-4-ylmethyl)-4-methoxybenzamide;
3-chloro-4-(difluoromethoxy)-N-(1H-indazol-4-ylmethyl)benzamide;
4-(difluoromethoxy)-N-(1H-indazol-4-ylmethyl)benzamide;

4-(difluoromethoxy)-3,5-difluoro-N-(1H-indazol-4-ylmethyl)benzamide;
3-chloro-N-(1H-indazol-4-ylmethyl)-4-methylbenzamide;
3-chloro-4-fluoro-N-(1H-indazol-4-ylmethyl)benzamide;
4-chloro-3-fluoro-N-(1H-indazol-4-ylmethyl)benzamide;
3-chloro-4,5-difluoro-N-(1H-indazol-4-ylmethyl)benzamide;
4-chloro-3,5-difluoro-N-(1H-indazol-4-ylmethyl)benzamide;
3-chloro-4-(difluoromethyl)-N-(1H-indazol-4-ylmethyl)benzamide;
6-(difluoromethoxy)-5-fluoro-N-(1H-indazol-4-ylmethyl)nicotinamide;
4-(difluoromethoxy)-3-fluoro-N-(1H-indazol-4-ylmethyl)benzamide;
5-fluoro-6-methoxy-N-((5-methyl-1H-benzotriazol-4-yl)methyl)nicotinamide;
N-((5-methyl-1H-benzotriazol-4-yl)methyl)-4-(trifluoromethoxy)-benzamide;
3,5-difluoro-N-((5-methyl-1H-benzotriazol-4-yl)methyl)-4-(trifluoromethyl)-benzamide;
3,5-difluoro-4-methyl-N-((5-methyl-1H-benzotriazol-4-yl)methyl)benzamide;
3,5-difluoro-4-methoxy-N-((5-methyl-1H-benzotriazol-4-yl)methyl)benzamide;
4-chloro-3,5-difluoro-N-((5-methyl-1H-benzotriazol-4-yl)methyl)benzamide;
3-fluoro-N-((5-methyl-1H-benzotriazol-4-yl)methyl)-4-(trifluoromethyl)-benzamide;
3-fluoro-4-methyl-N-((5-methyl-1H-benzotriazol-4-yl)methyl)benzamide;
3-fluoro-4-methoxy-N-((5-methyl-1H-benzotriazol-4-yl)methyl)benzamide;
3-chloro-4,5-difluoro-N-((5-methyl-1H-benzotriazol-4-yl)methyl)benzamide;
N-((5-cyclopropyl-1H-benzotriazol-4-yl)methyl)-4-(trifluoromethoxy)-benzamide;
N-((5-cyclopropyl-1H-benzotriazol-4-yl)methyl)-3,5-difluoro-4-methoxybenzamide;
N-((5-ethyl-1H-benzotriazol-4-yl)methyl)-3,5-difluoro-4-(trifluoromethyl)-benzamide;
N-((5-ethyl-1H-benzotriazol-4-yl)methyl)-3,5-difluoro-4-methoxybenzamide;
3,5-difluoro-4-methoxy-N-((5-methoxy-1H-benzotriazol-4-yl)methyl)benzamide;
N-((5-ethyl-1H-benzotriazol-4-yl)methyl)-5-fluoro-6-methoxynicotinamide;
N-((5-ethyl-1H-benzotriazol-4-yl)methyl)-4-(trifluoromethoxy)-benzamide;
3,5-difluoro-N-((6-fluoro-1-methyl-1H-benzimidazol-7-yl)methyl)-4-methoxybenzamide;
N-(1H-benzotriazol-4-yl methyl)-3,5-difluoro-4-methoxybenzamide;
N-((5-cyclopropyl-1H-benzotriazol-4-yl)methyl)-4-(difluoromethoxy)-3-fluorobenzamide;
N-((5-methoxy-1H-benzotriazol-4-yl)methyl)-4-(trifluoromethoxy)-benzamide;
3,5-difluoro-4-methoxy-N-((6-methoxy-1,2-dimethyl-1H-benzimidazol-7-yl)methyl)benzamide;
1-((6-methoxy-1-methyl-1H-benzimidazol-7-yl)methyl)-3-(3-methylphenyl)urea;
1-(3-fluorophenyl)-3-((6-methoxy-1-methyl-1H-benzimidazol-7-yl)methyl)urea;
1-(4-fluoro-3-methylphenyl)-3-((6-methoxy-1-methyl-1H-benzimidazol-7-yl)methyl)urea;
1-(3-fluoro-4-methylphenyl)-3-((6-methoxy-1-methyl-1H-benzimidazol-7-yl)methyl)urea;
1-(3-chlorophenyl)-3-((6-methoxy-1-methyl-1H-benzimidazol-7-yl)methyl)urea;
1-((6-methoxy-1-methyl-1H-benzimidazol-7-yl)methyl)-3-(3,4,5-trifluorophenyl)urea;
1-(4-(difluoromethoxy)-phenyl)-3-((6-methoxy-1-methyl-1H-benzimidazol-7-yl)methyl)urea;
1-((6-methoxy-1-methyl-1H-benzimidazol-7-yl)methyl)-3-(3-(trifluoromethyl)-phenyl)urea;
1-((6-methoxy-1-methyl-1H-benzimidazol-7-yl)methyl)-3-(4-(trifluoromethoxy)-phenyl)urea;
1-(4-fluorophenyl)-3-((6-methoxy-1-methyl-1H-benzimidazol-7-yl)methyl)urea;
1-(3-fluoro-4-methoxyphenyl)-3-((6-methoxy-1-methyl-1H-benzimidazol-7-yl)methyl)urea;
N-((5-cyclopropyl-1H-benzotriazol-4-yl)methyl)-6-(difluoromethoxy)-5-fluoronicotinamide;
3-fluoro-N-((5-methoxy-1H-benzotriazol-4-yl)methyl)-4-(trifluoromethoxy)-benzamide;
5-chloro-N-((6-methoxy-1,2-dimethyl-1H-benzimidazol-7-yl)methyl)thiophene-3-carboxamide;
5-chloro-N-((6-methoxy-1,2-dimethyl-1H-benzimidazol-7-yl)methyl)thiophene-2-carboxamide;
N-((6-methoxy-1,2-dimethyl-1H-benzimidazol-7-yl)methyl)-5-(trifluoromethyl)-thiophene-3-carboxamide;
N-((6-methoxy-1,2-dimethyl-1H-benzimidazol-7-yl)methyl)-5-(trifluoromethyl)-thiophene-2-carboxamide;
5-(difluoromethyl)-N-((6-methoxy-1,2-dimethyl-1H-benzimidazol-7-yl)methyl)thiophene-3-carboxamide;
N-((6-methoxy-1,2-dimethyl-1H-benzimidazol-7-yl)methyl)-6-(trifluoromethoxy)-nicotinamide;
6-ethoxy-5-fluoro-N-((6-methoxy-1,2-dimethyl-1H-benzimidazol-7-yl)methyl)nicotinamide;
5-fluoro-6-methoxy-N-((6-methoxy-1,2-dimethyl-1H-benzimidazol-7-yl)methyl)nicotinamide;
3-fluoro-N-((6-methoxy-1,2-dimethyl-1H-benzimidazol-7-yl)methyl)-4-(trifluoromethyl)-benzamide;
N-((6-methoxy-1,2-dimethyl-1H-benzimidazol-7-yl)methyl)-4-(trifluoromethyl)-benzamide;
3-fluoro-N-((6-methoxy-1,2-dimethyl-1H-benzimidazol-7-yl)methyl)-4-methylbenzamide;
3,5-difluoro-N-((6-methoxy-1,2-dimethyl-1H-benzimidazol-7-yl)methyl)-4-methylbenzamide;
4-(difluoromethyl)-3,5-difluoro-N-((6-methoxy-1,2-dimethyl-1H-benzimidazol-7-yl)methyl)benzamide;
4-(difluoromethyl)-N-((6-methoxy-1,2-dimethyl-1H-benzimidazol-7-yl)methyl)benzamide;
4-(difluoromethyl)-3-fluoro-N-((6-methoxy-1,2-dimethyl-1H-benzimidazol-7-yl)methyl)benzamide;
3-fluoro-4-methoxy-N-((6-methoxy-1,2-dimethyl-1H-benzimidazol-7-yl)methyl)benzamide;
3-chloro-4-(difluoromethoxy)-N-((6-methoxy-1,2-dimethyl-1H-benzimidazol-7-yl)methyl)benzamide;
4-(difluoromethoxy)-N-((6-methoxy-1,2-dimethyl-1H-benzimidazol-7-yl)methyl)benzamide;
4-(difluoromethoxy)-3,5-difluoro-N-((6-methoxy-1,2-dimethyl-1H-benzimidazol-7-yl)methyl)benzamide;
3-chloro-4-fluoro-N-((6-methoxy-1,2-dimethyl-1H-benzimidazol-7-yl)methyl)benzamide;
4-chloro-3-fluoro-N-((6-methoxy-1,2-dimethyl-1H-benzimidazol-7-yl)methyl)benzamide;
4-chloro-N-((6-methoxy-1,2-dimethyl-1H-benzimidazol-7-yl)methyl)benzamide;
3-chloro-4-(difluoromethyl)-N-((6-methoxy-1,2-dimethyl-1H-benzimidazol-7-yl)methyl)benzamide;

6-(difluoromethoxy)-5-fluoro-N-((6-methoxy-1,2-dimethyl-1H-benzimidazol-7-yl)methyl)nicotinamide;
N-((6-methoxy-1,2-dimethyl-1H-benzimidazol-7-yl)methyl)-4-(trifluoromethoxy)-benzamide;
4-(difluoromethoxy)-3-fluoro-N-((6-methoxy-1,2-dimethyl-1H-benzimidazol-7-yl)methyl)benzamide;
6-(difluoromethoxy)-N-((6-methoxy-1,2-dimethyl-1H-benzimidazol-7-yl)methyl)nicotinamide;
1-((6-methoxy-1-methyl-1H-benzimidazol-7-yl)methyl)-3-phenylurea;
1-((6-methoxy-1-methyl-1H-benzimidazol-7-yl)methyl)-3-(4-methylphenyl)urea;
1-(4-chlorophenyl)-3-((6-methoxy-1-methyl-1H-benzimidazol-7-yl)methyl)urea;
1-(3,4-difluorophenyl)-3-((6-methoxy-1-methyl-1H-benzimidazol-7-yl)methyl)urea;
1-(2,3-difluoro-4-methoxyphenyl)-3-((6-methoxy-1-methyl-1H-benzimidazol-7-yl)methyl)urea;
1-(2-fluoro-4-(trifluoromethyl)-phenyl)-3-((6-methoxy-1-methyl-1H-benzimidazol-7-yl)methyl)urea;
1-(3-fluoro-4-(trifluoromethyl)-phenyl)-3-((6-methoxy-1-methyl-1H-benzimidazol-7-yl)methyl)urea;
1-((6-methoxy-1-methyl-1H-benzimidazol-7-yl)methyl)-3-(4-(trifluoromethyl)-phenyl)urea;
4-(difluoromethoxy)-3-fluoro-N-((5-methyl-1H-benzotriazol-4-yl)methyl)benzamide;
4-methoxy-N-((5-methyl-1H-benzotriazol-4-yl)methyl)benzamide;
4-(difluoromethoxy)-N-((5-methyl-1H-benzotriazol-4-yl)methyl)benzamide;
1-((6-methoxy-1-methyl-1H-benzimidazol-7-yl)methyl)-3-(4-methoxyphenyl)urea;
1-(4-fluoro-3-(trifluoromethyl)-phenyl)-3-((6-methoxy-1-methyl-1H-benzimidazol-7-yl)methyl)urea;
6-(difluoromethoxy)-5-fluoro-N-((5-methyl-1H-benzotriazol-4-yl)methyl)nicotinamide;
3-fluoro-N-((3-methyl-1H-indazol-4-yl)methyl)-4-(trifluoromethoxy)-benzamide;
3,5-difluoro-4-methoxy-N-((3-methyl-1H-indazol-4-yl)methyl)benzamide;
6-(difluoromethoxy)-5-fluoro-N4(3-methyl-1H-indazol-4-yl)methyl)nicotinamide;
N-[(3-bromo-1H-indazol-4-yl)methyl]-3-fluoro-4-(trifluoromethoxy)-benzamide;
N-[(5-fluoro-1H-indazol-4-yl)methyl]-4-(trifluoromethoxy)-benzamide;
3-fluoro-N-[(1-methyl-1H-benzotriazol-7-yl)methyl]-4-(trifluoromethoxy)-benzamide;
6-(difluoromethoxy)-5-fluoro-N-[(1-methyl-1H-benzotriazol-7-yl)methyl]pyridine-3-carboxamide;
6-(difluoromethoxy)-N-[(6-methoxy-1-methyl-1H-benzimidazol-7-yl)methyl]pyridine-3-carboxamide;
4-(difluoromethoxy)-2-fluoro-N-[(6-methoxy-1-methyl-1H-benzimidazol-7-yl)methyl]benzamide;
N-[(6-methoxy-1-methyl-1H-benzimidazol-7-yl)methyl]-4-(2,2,2-trifluoroethyl)-benzamide;
3,5-difluoro-4-methoxy-N-{[6-(methoxymethyl)-1-methyl-1H-benzimidazol-7-yl]methyl}benzamide;
N-{[6-(methoxymethyl)-1-methyl-1H-benzimidazol-7-yl]methyl}-4-(trifluoromethyl)-benzamide;
6-(difluoromethoxy)-5-fluoro-N-{[6-(methoxymethyl)-1-methyl-1H-benzimidazol-7-yl]methyl}pyridine-3-carboxamide;
N-{[6-(methoxymethyl)-1-methyl-1H-benzimidazol-7-yl]methyl}-5-(trifluoromethyl)-thiophene-3-carboxamide;
3-chloro-4-(difluoromethoxy)-N-{[6-(methoxymethyl)-1-methyl-1H-benzimidazol-7-yl]methyl}benzamide;
3-fluoro-N-{[6-(methoxymethyl)-1-methyl-1H-benzimidazol-7-yl]methyl}-4-(trifluoromethoxy)-benzamide,
and salts thereof.

2. The method of claim 1, wherein the compound is 3,5-difluoro-4-methoxy-N-((6-methoxy-1-methyl-1H-benzimidazol-7-yl)methyl)benzamide or a salt thereof.

3. The method of claim 1, wherein the compound is 6-(difluoromethoxy)-N-((1,6-dimethyl-1H-benzimidazol-7-yl)methyl)-5-fluoronicotinamide or a salt thereof.

4. The method of claim 1, wherein the compound is N-((1,6-dimethyl-1H-benzimidazol-7-yl)methyl)-4-(trifluoromethoxy)benzamide or a salt thereof.

5. A method for treating major depression, bipolar disorder, migraine, pain or peripheral symptoms of dementia in a mammal, comprising administering to the mammal an effective amount of a compound chosen from:
N-((2,5-dimethyl-2H-indazol-4-yl)methyl)-4-(trifluoromethoxy)benzamide;
N-((5-methyl-1H-indazol-4-yl)methyl)-4-(trifluoromethoxy)benzamide;
N-((5-methyl-1H-benzimidazol-4-yl)methyl)-4-(trifluoromethoxy)benzamide;
N-((5-iodo-1H-indazol-4-yl)methyl)-4-(trifluoromethoxy)benzamide;
4-(trifluoromethoxy)-N-((5-(trifluoromethyl)-1H-indazol-4-yl)methyl)benzamide;
N-((5-methoxy-1H-indazol-4-yl)methyl)-4-(trifluoromethoxy)benzamide;
N-(1H-indazol-4-ylmethyl)-4-(trifluoromethoxy)benzamide;
3,5-difluoro-4-methoxy-N-((6-methoxy-1-methyl-1H-benzimidazol-7-yl)methyl)benzamide;
3,5-difluoro-N-((6-methoxy-1-methyl-1H-benzimidazol-7-yl)methyl)-4-methylbenzamide;
5-fluoro-6-methoxy-N-((6-methoxy-1-methyl-1H-benzimidazol-7-yl)methyl)nicotinamide;
3-fluoro-4-methoxy-N-((6-methoxy-1-methyl-1H-benzimidazol-7-yl)methyl)benzamide;
N-((6-methoxy-1-methyl-1H-benzimidazol-7-yl)methyl)-4-(trifluoromethoxy)benzamide;
3-fluoro-N-((6-methoxy-1-methyl-1H-benzimidazol-7-yl)methyl)-4-(trifluoromethyl)benzamide;
3-fluoro-N-((6-methoxy-1-methyl-1H-benzimidazol-7-yl)methyl)-4-methylbenzamide;
4-chloro-3,5-difluoro-N-((6-methoxy-1-methyl-1H-benzimidazol-7-yl)methyl)benzamide;
N-((5-ethyl-1H-indazol-4-yl)methyl)-3,5-difluoro-4-methoxybenzamide;
N-((5-cyclopropyl-1H-indazol-4-yl)methyl)-3,5-difluoro-4-methoxybenzamide;
3-chloro-4,5-difluoro-N-((6-methoxy-1-methyl-1H-benzimidazol-7-yl)methyl)benzamide;
N-((1,6-dimethyl-1H-benzimidazol-7-yl)methyl)-5-fluoro-6-methoxynicotinamide;
N-((6-cyclopropyl-1-methyl-1H-benzimidazol-7-yl)methyl)-5-fluoro-6-methoxynicotinamide;
N-((6-cyclopropyl-1-methyl-1H-benzimidazol-7-yl)methyl)-3,5-difluoro-4-methoxybenzamide;
N-((6-ethyl-1-methyl-1H-benzimidazol-7-yl)methyl)-5-fluoro-6-methoxynicotinamide;
N-((6-ethyl-1-methyl-1H-benzimidazol-7-yl)methyl)-3,5-difluoro-4-methoxybenzamide;
3,5-difluoro-N-((6-methoxy-1-methyl-1H-benzimidazol-7-yl)methyl)-4-(trifluoromethyl)benzamide;

N-((1,6-dimethyl-1H-benzimidazol-7-yl)methyl)-3,5-difluoro-4-methoxybenzamide;
N-((1,6-dimethyl-1H-benzimidazol-7-yl)methyl)-3,5-difluoro-4-(trifluoromethyl)benzamide;
N-((6-methoxy-1-methyl-1H-benzimidazol-7-yl)methyl)-5-methylthiophene-3-carboxamide;
5-chloro-N-((6-methoxy-1-methyl-1H-benzimidazol-7-yl)methyl)thiophene-3-carboxamide;
5-ethyl-N-((6-methoxy-1-methyl-1H-benzimidazol-7-yl)methyl)thiophene-3-carboxamide;
N-((1,6-dimethyl-1H-benzimidazol-7-yl)methyl)-3-fluoro-4-(trifluoromethoxy)benzamide;
3-chloro-4-(difluoromethoxy)-N-((1,6-dimethyl-1H-benzimidazol-7-yl)methyl)benzamide;
N-((6-methoxy-1-methyl-1H-benzimidazol-7-yl)methyl)-5-methylthiophene-2-carboxamide;
N-((6-methoxy-1-methyl-1H-benzimidazol-7-yl)methyl)-2-(2-thienyl)acetamide;
3-chloro-4-methoxy-N-((6-methoxy-1-methyl-1H-benzimidazol-7-yl)methyl)benzamide;
4-methoxy-N-((6-methoxy-1-methyl-1H-benzimidazol-7-yl)methyl)-3,5-dimethylbenzamide;
5-chloro-N-((6-methoxy-1-methyl-1H-benzimidazol-7-yl)methyl)thiophene-2-carboxamide;
3-chloro-4-fluoro-N-((6-methoxy-1-methyl-1H-benzimidazol-7-yl)methyl)benzamide;
3-chloro-N-((6-methoxy-1-methyl-1H-benzimidazol-7-yl)methyl)-4-methylbenzamide;
4-chloro-N-((6-methoxy-1-methyl-1H-benzimidazol-7-yl)methyl)-3-methylbenzamide;
4-fluoro-N-((6-methoxy-1-methyl-1H-benzimidazol-7-yl)methyl)-3-(trifluoromethyl)benzamide;
3,4,5-trifluoro-N-((6-methoxy-1-methyl-1H-benzimidazol-7-yl)methyl)benzamide;
4-chloro-N-((6-methoxy-1-methyl-1H-benzimidazol-7-yl)methyl)thiophene-2-carboxamide;
N-((6-methoxy-1-methyl-1H-benzimidazol-7-yl)methyl)-4-methylthiophene-2-carboxamide;
4-chloro-3-fluoro-N-((6-methoxy-1-methyl-1H-benzimidazol-7-yl)methyl)benzamide;
4-chloro-3-methoxy-N-((6-methoxy-1-methyl-1H-benzimidazol-7-yl)methyl)benzamide;
4-fluoro-3-methoxy-N-((6-methoxy-1-methyl-1H-benzimidazol-7-yl)methyl)benzamide;
N-((6-methoxy-1-methyl-1H-benzimidazol-7-yl)methyl)-4-methyl-3-(trifluoromethyl)benzamide;
5-methoxy-N-((6-methoxy-1-methyl-1H-benzimidazol-7-yl)methyl)thiophene-2-carboxamide;
3,5-dichloro-4-fluoro-N-((6-methoxy-1-methyl-1H-benzimidazol-7-yl)methyl)benzamide;
N-((6-methoxy-1-methyl-1H-benzimidazol-7-yl)methyl)-5-(trifluoromethyl)thiophene-2-carboxamide;
3-chloro-N-((6-methoxy-1-methyl-1H-benzimidazol-7-yl)methyl)-4-(trifluoromethyl)benzamide;
3-fluoro-N-((6-methoxy-1-methyl-1H-benzimidazol-7-yl)methyl)-4-(trifluoromethoxy)benzamide;
4,5-dichloro-N-((6-methoxy-1-methyl-1H-benzimidazol-7-yl)methyl)thiophene-2-carboxamide;
3,4-difluoro-N-((6-methoxy-1-methyl-1H-benzimidazol-7-yl)methyl)-5-methylbenzamide;
3,4-dichloro-5-fluoro-N-((6-methoxy-1-methyl-1H-benzimidazol-7-yl)methyl)benzamide;
N-((6-methoxy-1-methyl-1H-benzimidazol-7-yl)methyl)-6-(trifluoromethoxy)-nicotinamide;
5-chloro-6-methoxy-N-((6-methoxy-1-methyl-1H-benzimidazol-7-yl)methyl)nicotinamide;
5-chloro-6-ethoxy-N-((6-methoxy-1-methyl-1H-benzimidazol-7-yl)methyl)nicotinamide;
6-(difluoromethoxy)-5-fluoro-N-((6-methoxy-1-methyl-1H-benzimidazol-7-yl)methyl)nicotinamide;
3-chloro-N-((1,6-dimethyl-1H-benzimidazol-7-yl)methyl)-4-(trifluoromethoxy)-benzamide;
N-((5-cyclopropyl-1H-indazol-4-yl)methyl)-4-(trifluoromethyl)benzamide;
N-((5-cyclopropyl-1H-indazol-4-yl)methyl)-4-(trifluoromethoxy)benzamide;
N-((5-cyclopropyl-1H-indazol-4-yl)methyl)-4-methylthiophene-2-carboxamide;
N-((5-cyclopropyl-1H-indazol-4-yl)methyl)-5-methylthiophene-2-carboxamide;
N-((5-cyclopropyl-1H-indazol-4-yl)methyl)-2-(2-thienyl)acetamide;
N-((5-cyclopropyl-1H-indazol-4-yl)methyl)-5-methylthiophene-3-carboxamide;
N-((5-cyclopropyl-1H-indazol-4-yl)methyl)-5-methoxythiophene-2-carboxamide;
N-((5-cyclopropyl-1H-indazol-4-yl)methyl)-4-methoxythiophene-2-carboxamide;
5-chloro-N-((5-cyclopropyl-1H-indazol-4-yl)methyl)thiophene-3-carboxamide;
4-chloro-N-((5-cyclopropyl-1H-indazol-4-yl)methyl)thiophene-2-carboxamide;
5-chloro-N-((5-cyclopropyl-1H-indazol-4-yl)methyl)thiophene-2-carboxamide;
N-((5-cyclopropyl-1H-indazol-4-yl)methyl)-4-fluoro-3-methoxybenzamide;
4-chloro-N-((5-cyclopropyl-1H-indazol-4-yl)methyl)-3-methylbenzamide;
3-chloro-N-((5-cyclopropyl-1H-indazol-4-yl)methyl)-4-methylbenzamide;
N-((5-cyclopropyl-1H-indazol-4-yl)methyl)-4-fluoro-3-methylbenzamide;
N-((5-cyclopropyl-1H-indazol-4-yl)methyl)-3,4-difluoro-5-methylbenzamide;
3-chloro-N-((5-cyclopropyl-1H-indazol-4-yl)methyl)-4-fluorobenzamide;
4-chloro-N-((5-cyclopropyl-1H-indazol-4-yl)methyl)-3-fluorobenzamide;
N-((5-cyclopropyl-1H-indazol-4-yl)methyl)-3,4,5-trifluorobenzamide;
3-chloro-N-((5-cyclopropyl-1H-indazol-4-yl)methyl)-4-methoxybenzamide;
4-chloro-N-((5-cyclopropyl-1H-indazol-4-yl)methyl)-3-methoxybenzamide;
N-((5-cyclopropyl-1H-indazol-4-yl)methyl)-5-(trifluoromethyl)thiophene-2-carboxamide;
4,5-dichloro-N-((5-cyclopropyl-1H-indazol-4-yl)methyl)thiophene-2-carboxamide;
N-((5-cyclopropyl-1H-indazol-4-yl)methyl)-4-methyl-3-(trifluoromethyl)benzamide;
N-((5-cyclopropyl-1H-indazol-4-yl)methyl)-4-fluoro-3-(trifluoromethyl)benzamide;
3,5-dichloro-N-((5-cyclopropyl-1H-indazol-4-yl)methyl)-4-fluorobenzamide;
3,4-dichloro-N-((5-cyclopropyl-1H-indazol-4-yl)methyl)-5-fluorobenzamide;
N-((5-cyclopropyl-1H-indazol-4-yl)methyl)-3-fluoro-4-(trifluoromethoxy)benzamide;
3-chloro-N-((5-cyclopropyl-1H-indazol-4-yl)methyl)-4-(trifluoromethyl)benzamide;
4-chloro-N-((5-cyclopropyl-1H-indazol-4-yl)methyl)-3,5-difluorobenzamide;

N-((5-cyclopropyl-1H-indazol-4-yl)methyl)-3,5-difluoro-4-(trifluoromethyl)benzamide;
N-((5-cyclopropyl-1H-indazol-4-yl)methyl)-3-fluoro-4-(trifluoromethyl)benzamide;
N-((5-cyclopropyl-1H-indazol-4-yl)methyl)-3-fluoro-4-methylbenzamide;
N-((5-cyclopropyl-1H-indazol-4-yl)methyl)-3-fluoro-4-methoxybenzamide;
3-chloro-N-((5-cyclopropyl-1H-indazol-4-yl)methyl)-4,5-difluorobenzamide;
N-((5-cyclopropyl-1H-indazol-4-yl)methyl)-5-fluoro-6-methoxynicotinamide;
N-((5-cyclopropyl-1H-indazol-4-yl)methyl)-3,5-difluoro-4-methylbenzamide;
N-((5-cyclopropyl-1H-indazol-4-yl)methyl)-4-(difluoromethyl)benzamide;
N-((5-cyclopropyl-1H-indazol-4-yl)methyl)-4-methylbenzamide;
N-((5-cyclopropyl-1H-indazol-4-yl)methyl)-4-(difluoromethoxy)benzamide;
N-((5-cyclopropyl-1H-indazol-4-yl)methyl)-4-methoxybenzamide;
4-chloro-N-((5-cyclopropyl-1H-indazol-4-yl)methyl)benzamide;
5-chloro-N-((5-cyclopropyl-1H-indazol-4-yl)methyl)-6-methoxynicotinamide;
5-chloro-N-((5-cyclopropyl-1H-indazol-4-yl)methyl)-6-ethoxynicotinamide;
N-((5-cyclopropyl-1H-indazol-4-yl)methyl)-6-(difluoromethoxy)-5-fluoronicotinamide;
N-((5-cyclopropyl-1H-indazol-4-yl)methyl)-6-(trifluoromethoxy)-nicotinamide;
3-chloro-N-((5-cyclopropyl-1H-indazol-4-yl)methyl)-4-(difluoromethoxy)-benzamide;
N-((5-cyclopropyl-1H-indazol-4-yl)methyl)-4-(difluoromethyl)-3,5-difluorobenzamide;
4-(difluoromethoxy)-N-((1,6-dimethyl-1H-benzimidazol-7-yl)methyl)-3-fluorobenzamide;
5-(difluoromethyl)-N-((6-methoxy-1-methyl-1H-benzimidazol-7-yl)methyl)thiophene-3-carboxamide;
3-chloro-5-fluoro-4-methoxy-N-((6-methoxy-1-methyl-1H-benzimidazol-7-yl)methyl)benzamide;
3-chloro-4-(difluoromethyl)-N-((6-methoxy-1-methyl-1H-benzimidazol-7-yl)methyl)benzamide;
5-chloro-N-((6-methoxy-1-methyl-1H-benzimidazol-7-yl)methyl)-6-(trifluoromethyl)-nicotinamide;
N-((6-methoxy-1-methyl-1H-benzimidazol-7-yl)methyl)-4-methylbenzamide;
5-cyclopropyl-N-((6-methoxy-1-methyl-1H-benzimidazol-7-yl)methyl)thiophene-3-carboxamide;
4-chloro-N-((6-methoxy-1-methyl-1H-benzimidazol-7-yl)methyl)benzamide;
N-((6-methoxy-1-methyl-1H-benzimidazol-7-yl)methyl)-4-(trifluoromethyl)benzamide;
N-((5-cyclopropyl-1H-indazol-4-yl)methyl)-4-(difluoromethyl)-3-fluorobenzamide;
N-((5-cyclopropyl-1H-indazol-4-yl)methyl)-6-ethoxy-5-fluoronicotinamide;
N-((5-cyclopropyl-1H-indazol-4-yl)methyl)-4-(difluoromethoxy)-3-fluorobenzamide;
5-chloro-N-((5-cyclopropyl-1H-indazol-4-yl)methyl)-6-(difluoromethoxy)-nicotinamide;
5-ethyl-N-((6-methoxy-1-methyl-1H-benzimidazol-7-yl)methyl)thiophene-2-carboxamide;
4-(difluoromethyl)-N-((6-methoxy-1-methyl-1H-benzimidazol-7-yl)methyl)benzamide;
4-(difluoromethyl)-3-fluoro-N-((6-methoxy-1-methyl-1H-benzimidazol-7-yl)methyl)benzamide;
5-(difluoromethyl)-N-((6-ethoxy-1-methyl-1H-benzimidazol-7-yl)methyl)thiophene-3-carboxamide;
5-(difluoromethyl)-N-((6-ethoxy-1-methyl-1H-benzimidazol-7-yl)methyl)thiophene-2-carboxamide;
N-((6-ethoxy-1-methyl-1H-benzimidazol-7-yl)methyl)-3,5-difluoro-4-methoxybenzamide;
N-((6-ethoxy-1-methyl-1H-benzimidazol-7-yl)methyl)-4-(trifluoromethyl)-benzamide;
N-((1,6-dimethyl-1H-benzimidazol-7-yl)methyl)-3-fluoro-4-methoxybenzamide;
N-((6-ethyl-1-methyl-1H-benzimidazol-7-yl)methyl)-3-fluoro-4-methoxybenzamide;
4-(difluoromethoxy)-N-((6-ethyl-1-methyl-1H-benzimidazol-7-yl)methyl)-3,5-difluorobenzamide;
5-(difluoromethyl)-N-((6-ethyl-1-methyl-1H-benzimidazol-7-yl)methyl)thiophene-3-carboxamide;
4-(difluoromethyl)-N-((6-ethyl-1-methyl-1H-benzimidazol-7-yl)methyl)benzamide;
6-(difluoromethoxy)-N-((1,6-dimethyl-1H-benzimidazol-7-yl)methyl)-5-fluoronicotinamide;
4-(difluoromethoxy)-N-((1,6-dimethyl-1H-benzimidazol-7-yl)methyl)benzamide;
4-(difluoromethyl)-N-((1,6-dimethyl-1H-benzimidazol-7-yl)methyl)-3-fluorobenzamide;
5-(difluoromethyl)-N-((1,6-dimethyl-1H-benzimidazol-7-yl)methyl)thiophene-2-carboxamide;
N-((1,6-dimethyl-1H-benzimidazol-7-yl)methyl)-6-(trifluoromethoxy)-nicotinamide;
N-((6-methoxy-1-methyl-1H-benzimidazol-7-yl)methyl)-5-(trifluoromethyl)-thiophene-3-carboxamide;
4-(difluoromethyl)-N-((6-ethoxy-1-methyl-1H-benzimidazol-7-yl)methyl)benzamide;
4-(difluoromethyl)-N-((6-ethoxy-1-methyl-1H-benzimidazol-7-yl)methyl)-3-fluorobenzamide;
5-(difluoromethyl)-N-((1,6-dimethyl-1H-benzimidazol-7-yl)methyl)thiophene-3-carboxamide;
6-(difluoromethoxy)-N-((6-ethyl-1-methyl-1H-benzimidazol-7-yl)methyl)-5-fluoronicotinamide;
5-cyclopropyl-N-((1,6-dimethyl-1H-benzimidazol-7-yl)methyl)thiophene-3-carboxamide;
N-((6-ethyl-1-methyl-1H-benzimidazol-7-yl)methyl)-4-methoxybenzamide;
4-(difluoromethyl)-N-((6-ethyl-1-methyl-1H-benzimidazol-7-yl)methyl)-3-fluorobenzamide;
5-chloro-N-((6-ethyl-1-methyl-1H-benzimidazol-7-yl)methyl)thiophene-3-carboxamide;
4-(difluoromethoxy)-N-((6-ethyl-1-methyl-1H-benzimidazol-7-yl)methyl)benzamide;
N-((6-ethyl-1-methyl-1H-benzimidazol-7-yl)methyl)-6-(trifluoromethoxy)-nicotinamide;
N-((1-ethyl-6-methoxy-1H-benzimidazol-7-yl)methyl)-5-fluoro-6-methoxynicotinamide;
N-((1-ethyl-6-methoxy-1H-benzimidazol-7-yl)methyl)-3,5-difluoro-4-methoxybenzamide;
N-((1,6-dimethyl-1H-benzimidazol-7-yl)methyl)-4-(trifluoromethoxy)-benzamide;
N-((5-cyclopropyl-1H-indazol-4-yl)methyl)-4-(difluoromethoxy)-3,5-difluorobenzamide;
N-((5-cyclopropyl-1H-indazol-4-yl)methyl)-5-(difluoromethyl)-thiophene-3-carboxamide;
N-((5-cyclopropyl-1H-indazol-4-yl)methyl)-5-(difluoromethyl)-thiophene-2-carboxamide;
5-chloro-N-((1,6-dimethyl-1H-benzimidazol-7-yl)methyl)thiophene-3-carboxamide;

4-(difluoromethyl)-N-((1,6-dimethyl-1H-benzimidazol-7-yl)methyl)benzamide;
4-(difluoromethoxy)-N-((1,6-dimethyl-1H-benzimidazol-7-yl)methyl)-3,5-difluorobenzamide;
6-(difluoromethoxy)-N-((1,6-dimethyl-1H-benzimidazol-7-yl)methyl)nicotinamide;
3,5-difluoro-4-methoxy-N-((1-methyl-1H-benzimidazol-7-yl)methyl)benzamide;
4-(difluoromethoxy)-3,5-difluoro-N-((6-methoxy-1-methyl-1H-benzimidazol-7-yl)methyl)benzamide;
N-((6-methoxy-1-methyl-1H-benzimidazol-7-yl)methyl)-5-(trifluoromethyl)-thiophene-2-carboxamide hydrochloride;
N-((1,6-dimethyl-1H-benzimidazol-7-yl)methyl)-5-(trifluoromethyl)-thiophene-3-carboxamide;
6-(difluoromethoxy)-N-((6-ethyl-1-methyl-1H-benzimidazol-7-yl)methyl)nicotinamide;
N-((5-cyclopropyl-1H-benzotriazol-4-yl)methyl)-5-fluoro-6-methoxynicotinamide;
5-chloro-N-(1H-indazol-4-ylmethyl)thiophene-3-carboxamide;
N-(1H-indazol-4-ylmethyl)-5-(trifluoromethyl)-thiophene-2-carboxamide;
4,5-dichloro-N-(1H-indazol-4-ylmethyl)thiophene-2-carboxamide;
5-chloro-N-(1H-indazol-4-ylmethyl)-6-methoxynicotinamide;
N-(1H-indazol-4-ylmethyl)-6-(trifluoromethoxy)-nicotinamide;
6-ethoxy-5-fluoro-N-(1H-indazol-4-ylmethyl)nicotinamide;
5-fluoro-N-(1H-indazol-4-ylmethyl)-6-methoxynicotinamide;
3,5-difluoro-N-(1H-indazol-4-ylmethyl)-4-(trifluoromethyl)-benzamide;
3-fluoro-N-(1H-indazol-4-ylmethyl)-4-(trifluoromethyl)-benzamide;
N-(1H-indazol-4-ylmethyl)-4-(trifluoromethyl)-benzamide;
3-fluoro-N-(1H-indazol-4-ylmethyl)-4-methylbenzamide;
4-(difluoromethyl)-N-(1H-indazol-4-ylmethyl)benzamide;
4-(difluoromethyl)-3-fluoro-N-(1H-indazol-4-ylmethyl)benzamide;
3-fluoro-N-(1H-indazol-4-ylmethyl)-4-(trifluoromethoxy)-benzamide;
3,5-difluoro-N-(1H-indazol-4-ylmethyl)-4-methoxybenzamide;
3-fluoro-N-(1H-indazol-4-ylmethyl)-4-methoxybenzamide;
3-chloro-4-(difluoromethoxy)-N-(1H-indazol-4-ylmethyl)benzamide;
4-(difluoromethoxy)-N-(1H-indazol-4-ylmethyl)benzamide;
4-(difluoromethoxy)-3,5-difluoro-N-(1H-indazol-4-ylmethyl)benzamide;
3-chloro-N-(1H-indazol-4-ylmethyl)-4-methylbenzamide;
3-chloro-4-fluoro-N-(1H-indazol-4-ylmethyl)benzamide;
4-chloro-3-fluoro-N-(1H-indazol-4-ylmethyl)benzamide;
3-chloro-4,5-difluoro-N-(1H-indazol-4-ylmethyl)benzamide;
4-chloro-3,5-difluoro-N-(1H-indazol-4-ylmethyl)benzamide;
3-chloro-4-(difluoromethyl)-N-(1H-indazol-4-ylmethyl)benzamide;
6-(difluoromethoxy)-5-fluoro-N-(1H-indazol-4-ylmethyl)nicotinamide;
4-(difluoromethoxy)-3-fluoro-N-(1H-indazol-4-ylmethyl)benzamide;
5-fluoro-6-methoxy-N-((5-methyl-1H-benzotriazol-4-yl)methyl)nicotinamide;
N-((5-methyl-1H-benzotriazol-4-yl)methyl)-4-(trifluoromethoxy)-benzamide;
3,5-difluoro-N-((5-methyl-1H-benzotriazol-4-yl)methyl)-4-(trifluoromethyl)-benzamide;
3,5-difluoro-4-methyl-N-((5-methyl-1H-benzotriazol-4-yl)methyl)benzamide;
3,5-difluoro-4-methoxy-N-((5-methyl-1H-benzotriazol-4-yl)methyl)benzamide;
4-chloro-3,5-difluoro-N-((5-methyl-1H-benzotriazol-4-yl)methyl)benzamide;
3-fluoro-N-((5-methyl-1H-benzotriazol-4-yl)methyl)-4-(trifluoromethyl)-benzamide;
3-fluoro-4-methyl-N-((5-methyl-1H-benzotriazol-4-yl)methyl)benzamide;
3-fluoro-4-methoxy-N-((5-methyl-1H-benzotriazol-4-yl)methyl)benzamide;
3-chloro-4,5-difluoro-N-((5-methyl-1H-benzotriazol-4-yl)methyl)benzamide;
N-((5-cyclopropyl-1H-benzotriazol-4-yl)methyl)-4-(trifluoromethoxy)-benzamide;
N-((5-cyclopropyl-1H-benzotriazol-4-yl)methyl)-3,5-difluoro-4-methoxybenzamide;
N-((5-ethyl-1H-benzotriazol-4-yl)methyl)-3,5-difluoro-4-(trifluoromethyl)-benzamide;
N-((5-ethyl-1H-benzotriazol-4-yl)methyl)-3,5-difluoro-4-methoxybenzamide;
3,5-difluoro-4-methoxy-N-((5-methoxy-1H-benzotriazol-4-yl)methyl)benzamide;
N-((5-ethyl-1H-benzotriazol-4-yl)methyl)-5-fluoro-6-methoxynicotinamide;
N-((5-ethyl-1H-benzotriazol-4-yl)methyl)-4-(trifluoromethoxy)-benzamide;
3,5-difluoro-N-((6-fluoro-1-methyl-1H-benzimidazol-7-yl)methyl)-4-methoxybenzamide;
N-(1H-benzotriazol-4-yl methyl)-3,5-difluoro-4-methoxybenzamide;
N-((5-cyclopropyl-1H-benzotriazol-4-yl)methyl)-4-(difluoromethoxy)-3-fluorobenzamide;
N-((5-methoxy-1H-benzotriazol-4-yl)methyl)-4-(trifluoromethoxy)-benzamide;
3,5-difluoro-4-methoxy-N-((6-methoxy-1,2-dimethyl-1H-benzimidazol-7-yl)methyl)benzamide;
1-((6-methoxy-1-methyl-1H-benzimidazol-7-yl)methyl)-3-(3-methylphenyl)urea;
1-(3-fluorophenyl)-3-((6-methoxy-1-methyl-1H-benzimidazol-7-yl)methyl)urea;
1-(4-fluoro-3-methylphenyl)-3-((6-methoxy-1-methyl-1H-benzimidazol-7-yl)methyl)urea;
1-(3-fluoro-4-methylphenyl)-3-((6-methoxy-1-methyl-1H-benzimidazol-7-yl)methyl)urea;
1-(3-chlorophenyl)-3-((6-methoxy-1-methyl-1H-benzimidazol-7-yl)methyl)urea;
1-((6-methoxy-1-methyl-1H-benzimidazol-7-yl)methyl)-3-(3,4,5-trifluorophenyl)urea;
1-(4-(difluoromethoxy)-phenyl)-3-((6-methoxy-1-methyl-1H-benzimidazol-7-yl)methyl)urea;
1-((6-methoxy-1-methyl-1H-benzimidazol-7-yl)methyl)-3-(3-(trifluoromethyl)-phenyl)urea;
1-((6-methoxy-1-methyl-1H-benzimidazol-7-yl)methyl)-3-(4-(trifluoromethoxy)-phenyl)urea;

1-(4-fluorophenyl)-3-((6-methoxy-1-methyl-1H-benzimidazol-7-yl)methyl)urea;
1-(3-fluoro-4-methoxyphenyl)-3-((6-methoxy-1-methyl-1H-benzimidazol-7-yl)methyl)urea;
N-((5-cyclopropyl-1H-benzotriazol-4-yl)methyl)-6-(difluoromethoxy)-5-fluoronicotinamide;
3-fluoro-N-((5-methoxy-1H-benzotriazol-4-yl)methyl)-4-(trifluoromethoxy)-benzamide;
5-chloro-N-((6-methoxy-1,2-dimethyl-1H-benzimidazol-7-yl)methyl)thiophene-3-carboxamide;
5-chloro-N-((6-methoxy-1,2-dimethyl-1H-benzimidazol-7-yl)methyl)thiophene-2-carboxamide;
N-((6-methoxy-1,2-dimethyl-1H-benzimidazol-7-yl)methyl)-5-(trifluoromethyl)-thiophene-3-carboxamide;
N-((6-methoxy-1,2-dimethyl-1H-benzimidazol-7-yl)methyl)-5-(trifluoromethyl)-thiophene-2-carboxamide;
5-(difluoromethyl)-N-((6-methoxy-1,2-dimethyl-1H-benzimidazol-7-yl)methyl)thiophene-3-carboxamide;
N-((6-methoxy-1,2-dimethyl-1H-benzimidazol-7-yl)methyl)-6-(trifluoromethoxy)-nicotinamide;
6-ethoxy-5-fluoro-N-((6-methoxy-1,2-dimethyl-1H-benzimidazol-7-yl)methyl)nicotinamide;
5-fluoro-6-methoxy-N-((6-methoxy-1,2-dimethyl-1H-benzimidazol-7-yl)methyl)nicotinamide;
3-fluoro-N-((6-methoxy-1,2-dimethyl-1H-benzimidazol-7-yl)methyl)-4-(trifluoromethyl)-benzamide;
N-((6-methoxy-1,2-dimethyl-1H-benzimidazol-7-yl)methyl)-4-(trifluoromethyl)-benzamide;
3-fluoro-N-((6-methoxy-1,2-dimethyl-1H-benzimidazol-7-yl)methyl)-4-methylbenzamide;
3,5-difluoro-N-((6-methoxy-1,2-dimethyl-1H-benzimidazol-7-yl)methyl)-4-methylbenzamide;
4-(difluoromethyl)-3,5-difluoro-N-((6-methoxy-1,2-dimethyl-1H-benzimidazol-7-yl)methyl)benzamide;
4-(difluoromethyl)-N-((6-methoxy-1,2-dimethyl-1H-benzimidazol-7-yl)methyl)benzamide;
4-(difluoromethyl)-3-fluoro-N-((6-methoxy-1,2-dimethyl-1H-benzimidazol-7-yl)methyl)benzamide;
3-fluoro-4-methoxy-N-((6-methoxy-1,2-dimethyl-1H-benzimidazol-7-yl)methyl)benzamide;
3-chloro-4-(difluoromethoxy)-N-((6-methoxy-1,2-dimethyl-1H-benzimidazol-7-yl)methyl)benzamide;
4-(difluoromethoxy)-N-((6-methoxy-1,2-dimethyl-1H-benzimidazol-7-yl)methyl)benzamide;
4-(difluoromethoxy)-3,5-difluoro-N-((6-methoxy-1,2-dimethyl-1H-benzimidazol-7-yl)methyl)benzamide;
3-chloro-4-fluoro-N-((6-methoxy-1,2-dimethyl-1H-benzimidazol-7-yl)methyl)benzamide;
4-chloro-3-fluoro-N-((6-methoxy-1,2-dimethyl-1H-benzimidazol-7-yl)methyl)benzamide;
4-chloro-N-((6-methoxy-1,2-dimethyl-1H-benzimidazol-7-yl)methyl)benzamide;
3-chloro-4-(difluoromethyl)-N-((6-methoxy-1,2-dimethyl-1H-benzimidazol-7-yl)methyl)benzamide;
6-(difluoromethoxy)-5-fluoro-N-((6-methoxy-1,2-dimethyl-1H-benzimidazol-7-yl)methyl)nicotinamide;
N-((6-methoxy-1,2-dimethyl-1H-benzimidazol-7-yl)methyl)-4-(trifluoromethoxy)-benzamide;
4-(difluoromethoxy)-3-fluoro-N-((6-methoxy-1,2-dimethyl-1H-benzimidazol-7-yl)methyl)benzamide;
6-(difluoromethoxy)-N-((6-methoxy-1,2-dimethyl-1H-benzimidazol-7-yl)methyl)nicotinamide;
1-((6-methoxy-1-methyl-1H-benzimidazol-7-yl)methyl)-3-phenylurea;
1-((6-methoxy-1-methyl-1H-benzimidazol-7-yl)methyl)-3-(4-methylphenyl)urea;
1-(4-chlorophenyl)-3-((6-methoxy-1-methyl-1H-benzimidazol-7-yl)methyl)urea;
1-(3,4-difluorophenyl)-3-((6-methoxy-1-methyl-1H-benzimidazol-7-yl)methyl)urea;
1-(2,3-difluoro-4-methoxyphenyl)-3-((6-methoxy-1-methyl-1H-benzimidazol-7-yl)methyl)urea;
1-(2-fluoro-4-(trifluoromethyl)-phenyl)-3-((6-methoxy-1-methyl-1H-benzimidazol-7-yl)methyl)urea;
1-(3-fluoro-4-(trifluoromethyl)-phenyl)-3-((6-methoxy-1-methyl-1H-benzimidazol-7-yl)methyl)urea;
1-((6-methoxy-1-methyl-1H-benzimidazol-7-yl)methyl)-3-(4-(trifluoromethyl)-phenyl)urea;
4-(difluoromethoxy)-3-fluoro-N-((5-methyl-1H-benzotriazol-4-yl)methyl)benzamide;
4-methoxy-N-((5-methyl-1H-benzotriazol-4-yl)methyl)benzamide;
4-(difluoromethoxy)-N-((5-methyl-1H-benzotriazol-4-yl)methyl)benzamide;
1-((6-methoxy-1-methyl-1H-benzimidazol-7-yl)methyl)-3-(4-methoxyphenyl)urea;
1-(4-fluoro-3-(trifluoromethyl)-phenyl)-3-((6-methoxy-1-methyl-1H-benzimidazol-7-yl)methyl)urea;
6-(difluoromethoxy)-5-fluoro-N-((5-methyl-1H-benzotriazol-4-yl)methyl)nicotinamide;
3-fluoro-N-((3-methyl-1H-indazol-4-yl)methyl)-4-(trifluoromethoxy)-benzamide;
3,5-difluoro-4-methoxy-N-((3-methyl-1H-indazol-4-yl)methyl)benzamide;
6-(difluoromethoxy)-5-fluoro-N-((3-methyl-1H-indazol-4-yl)methyl)nicotinamide;
N-[(3-bromo-1H-indazol-4-yl)methyl]-3-fluoro-4-(trifluoromethoxy)-benzamide;
N-[(5-fluoro-1H-indazol-4-yl)methyl]-4-(trifluoromethoxy)-benzamide;
3-fluoro-N-[(1-methyl-1H-benzotriazol-7-yl)methyl]-4-(trifluoromethoxy)-benzamide;
6-(difluoromethoxy)-5-fluoro-N-[(1-methyl-1H-benzotriazol-7-yl)methyl]pyridine-3-carboxamide;
6-(difluoromethoxy)-N-[(6-methoxy-1-methyl-1H-benzimidazol-7-yl)methyl]pyridine-3-carboxamide;
4-(difluoromethoxy)-2-fluoro-N-[(6-methoxy-1-methyl-1H-benzimidazol-7-yl)methyl]benzamide;
N-[(6-methoxy-1-methyl-1H-benzimidazol-7-yl)methyl]-4-(2,2,2-trifluoroethyl)-benzamide;
3,5-difluoro-4-methoxy-N-{[6-(methoxymethyl)-1-methyl-1H-benzimidazol-7-yl]methyl}benzamide;
N-{[6-(methoxymethyl)-1-methyl-1H-benzimidazol-7-yl]methyl}-4-(trifluoromethyl)-benzamide;
6-(difluoromethoxy)-5-fluoro-N-{[6-(methoxymethyl)-1-methyl-1H-benzimidazol-7-yl]methyl}pyridine-3-carboxamide;
N-{[6-(methoxymethyl)-1-methyl-1H-benzimidazol-7-yl]methyl}-5-(trifluoromethyl)-thiophene-3-carboxamide;
3-chloro-4-(difluoromethoxy)-N-{[6-(methoxymethyl)-1-methyl-1H-benzimidazol-7-yl]methyl}benzamide;
3-fluoro-N-{[6-(methoxymethyl)-1-methyl-1H-benzimidazol-7-yl]methyl}-4-(trifluoromethoxy)-benzamide,
and salts thereof.

6. The method of claim 5, wherein the compound is 3,5-difluoro-4-methoxy-N-((6-methoxy-1-methyl-1H-benzimidazol-7-yl)methyl)benzamide or a salt thereof.

7. The method of claim 5, wherein the compound is 6-(difluoromethoxy)-N-((1,6-dimethyl-1H-benzimidazol-7-yl)methyl)-5-fluoronicotinamide or a salt thereof.

8. The method of claim 5, wherein the compound is N-((1,6-dimethyl-1H-benzimidazol-7-yl)methyl)-4-(trifluoromethoxy)benzamide or a salt thereof.

\* \* \* \* \*

UNITED STATES PATENT AND TRADEMARK OFFICE
CERTIFICATE OF CORRECTION

| | | |
|---|---|---|
| PATENT NO. | : 11,713,311 B2 | Page 1 of 1 |
| APPLICATION NO. | : 17/550173 | |
| DATED | : August 1, 2023 | |
| INVENTOR(S) | : Eiji Kimura et al. | |

It is certified that error appears in the above-identified patent and that said Letters Patent is hereby corrected as shown below:

In the Claims

Claim 1, Column 187, Lines 42-43:
"6-(difluoromethoxy)-5-fluoro-N4(3-methyl-1H-indazol-4-yl)methyl)nicotinamide;"
Should read:
--6-(difluoromethoxy)-5-fluoro-N-((3-methyl-1H-indazol-4-yl)methyl)nicotinamide;--.

Signed and Sealed this
Twenty-first Day of November, 2023

Katherine Kelly Vidal
*Director of the United States Patent and Trademark Office*